United States Patent
Sizemore et al.

(10) Patent No.: US 11,254,652 B2
(45) Date of Patent: Feb. 22, 2022

(54) CRYSTALLINE FORMS OF N-(4-(4-(CYCLOPROPYMETHYL) PIPERAZINE-1-CARBONYL)PHENYL) QUINOLINE-8-SULFONAMIDE

(71) Applicant: Agios Pharmaceuticals, Inc., Cambridge, MA (US)

(72) Inventors: Jacob P. Sizemore, Cambridge, MA (US); Liting Guo, Suzhou (CN); Mahmoud Mirmehrabi, Halifax (CA); Yeqing Su, Halifax (CA)

(73) Assignee: Agios Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 16/765,456

(22) PCT Filed: Nov. 21, 2018

(86) PCT No.: PCT/US2018/062197
§ 371 (c)(1),
(2) Date: May 19, 2020

(87) PCT Pub. No.: WO2019/104134
PCT Pub. Date: May 31, 2019

(65) Prior Publication Data
US 2020/0277279 A1 Sep. 3, 2020

Related U.S. Application Data

(60) Provisional application No. 62/691,709, filed on Jun. 29, 2018, provisional application No. 62/589,822, filed on Nov. 22, 2017.

(51) Int. Cl.
*C07D 401/12* (2006.01)

(52) U.S. Cl.
CPC ........ *C07D 401/12* (2013.01); *C07B 2200/13* (2013.01)

(58) Field of Classification Search
CPC combination set(s) only.
See application file for complete search history.

(56) References Cited

U.S. PATENT DOCUMENTS

| 8,785,450 B2 | 7/2014 | Salituro et al. |
| 2010/0331307 A1 | 12/2010 | Salituro et al. |

FOREIGN PATENT DOCUMENTS

| WO | 2016/201227 A1 | 12/2016 |

OTHER PUBLICATIONS

U.S. Appl. No. 16/900,610, filed Jun. 12, 2020.
Barbier et al., American Society of Hematology—57th Annual Meeting. Drive PK: A Phase 2 trial of AG-348 in patients with pyruvate kinase deficiency. Congress Presentation, Dec. 3, 2015, 1 page. (abstract only).
Barbier et al., ENERCA (2015) 6th European Symposium on Rare Anaemias. Activator treatment for pyruvate kinase deficiency—results from phase 1 and overview of phase 2 trial. Congress Presentation, Nov. 21, 2015, 1 page. (abstract only).
Barbier et al., ESH/ENERCA Training Course on Diagnosis and Management of Very Rare Red Cell and Iron Disorders. New treatments of pyruvate kinase deficiency: A Phase 1 multiple ascending dose study of the safety, tolerability, and pharmacokinetics/pharmacodynamics of AG-348, a first-in-class allosteric activator of pyruvate kinase-R, in healthy subjects. Congress Presentation, Jan. 29, 2016, 20 pages.
Barbier, European Hematology Association—20th Congress. Pyruvate kinase deficiency—clinical development update. Congress Presentation, Jun. 11, 2015, 3 pages.
Chen et al., European Hematology Association—20th Congress. Preclinical pharmacokinetic/pharmacodynamic relationships for AG-348, an investigational small-molecule activator of pyruvate kinase. Congress Presentation Poster, Jun. 13, 2015, 1 page.
Chen et al., European Hematology Association—20th Congress. Preclinical pharmacokinetic/pharmacodynamic relationships for AG-348, an investigational small-molecule activator of pyruvate kinase. Congress Presentation, Jun. 11, 2015, 2 pages. (abstract only).
Chubukov et al., American Society of Hematology—58th Annual Meeting. Characterization of metabolic response to AG-348, an allosteric activator of red cell pyruvate kinase, in healthy volunteers and pyruvate kinase deficiency patients. Congress Presentation Poster, Dec. 5, 2016, 1 page.
Chubukov et al., American Society of Hematology—58th Annual Meeting. Characterization of metabolic response to AG-348, an allosteric activator of red cell pyruvate kinase, in healthy volunteers and pyruvate kinase deficiency patients. Congress Presentation, Nov. 3, 2016, 3 pages. (abstract only).
Clinical & Pharmaceutical Solutions through Analysis—17th Annual Symposium. Metabolic consequences of pyruvate kinase deficiency (PKD), & their correction with AG-348. Congress Presentation, Oct. 2, 2014, 2014, 22 pages.
Clinical & Pharmaceutical Solutions through Analysis—3rd Annual Metabolomics Symposium. Using metabolism to support drug discovery: from target identification to biomarker validation. Congress Presentation, Feb. 27, 2017, 22 pages.

(Continued)

*Primary Examiner* — Heidi Reese
(74) *Attorney, Agent, or Firm* — McCarter & English, LLP

(57) ABSTRACT

Provided herein are amorphous and crystalline hemisulfate salt forms of the formula (I). Also provided are pharmaceutical compositions comprising the amorphous and crystalline hemisulfate salt forms, methods for their manufacture, and uses thereof for treating conditions associated with pyruvate kinase such as e.g., pyruvate kinase deficiency.

(I)

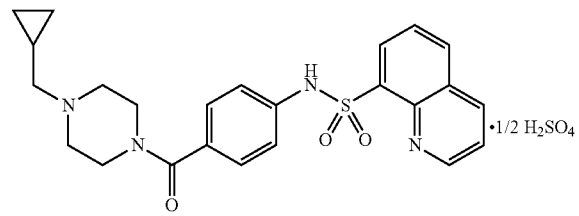

8 Claims, 26 Drawing Sheets

(56) References Cited

OTHER PUBLICATIONS

Glenthoj et al., European Hematology Association Scientific Working Group—2019 Scientific Meeting on Red Cell and Iron Metabolism Defects. Activate: An ongoing, phase 3, randomized, double-blind, placebo-controlled study with mitapivat (AG-348) in adults with pyruvate kinase deficiency who are not regularly transfused. Congress Presentation Poster, Nov. 7, 2019, 1 page.
Grace et al., American Society of Hematology—58th Annual Meeting. Effects of AG-348, a pyruvate kinase activator, on anemia and hemolysis in patients with pyruvate kinase (PK) deficiency: data from the Drive PK study. Congress Presentation, Dec. 4, 2016, 14 pages.
Grace et al., American Society of Hematology—58th Annual Meeting. Effects of AG-348, a pyruvate kinase activator, on anemia and hemolysis in patients with pyruvate kinase deficiency: data from the Drive PK study. Congress Presentation, Dec. 3, 2016, 1 page. (abstract only).
Grace et al., American Society of Hematology—59th Annual Meeting. Effects of AG-348, a pyruvate kinase activator, in patients with pyruvate kinase deficiency: Updated results from the Drive PK study. Congress Presentation Poster, Dec. 10, 2017, 1 page.
Grace et al., American Society of Hematology—59th Annual Meeting. Results update from the Drive PK study: Effects of AG-348, a pyruvate kinase activator, in patients with pyruvate kinase deficiency. Congress Presentation, Dec. 9, 2017, 2 pages. (abstract only).
Grace et al., American Society of Hematology—61st Annual Meeting. Long-term safety and efficacy of mitapivat (AG-348), a pyruvate kinase activator, in patients with pyruvate kinase deficiency: The Drive PK study. Congress Presentation Poster, Dec. 9, 2019, 1 page.
Grace et al., American Society of Hematology—61st Annual Meeting. Long-term safety and efficacy of mitapivat (AG-348), a pyruvate kinase activator, in patients with pyruvate kinase deficiency: The Drive PK study. Congress Presentation, Dec. 3, 2019, 5 pages. (abstract only).
Grace et al., British Blood Transfusion Society—Red Cell Special Interest Group Meeting in 2017. Effects of AG-348, a first in class pyruvate kinase activator, in patients with pyruvate kinase deficiency: Updated results from the Drive PK study. Congress Presentation, Sep. 13, 2017, 19 pages.
Grace et al., European Hematology Association—21st Congress. Effects of AG-348, a pyruvate kinase activator, on anemia and hemolysis in patients with pyruvate kinase deficiency. Congress Presentation, Jun. 9, 2016, 1 page. (abstract only).
Grace et al., European Hematology Association—21st Congress. Effects of AG-348, a pyruvate kinase activator, on anemia and hemolysis in patients with pyruvate kinase deficiency: early data from the Drive-PK study. Congress Presentation, Jun. 11, 2016, 17 pages.
Grace et al., European Hematology Association—22nd Congress. Effects of AG-348, a pyruvate kinase activator, in patients with pyruvate kinase deficiency: updated results from the Drive PK study. Congress Presentation, Jun. 22, 2017, 1 page. (abstract only).
Grace et al., European Hematology Association—22nd Congress. Effects of AG-348, a pyruvate kinase activator, in patients with pyruvate kinase deficiency: updated results from the Drive PK study. Congress Presentation, Jun. 22, 2017, 17 pages.
Grace et al., European Hematology Association—25th Congress. Mitapivat (AG-348) long-term safety and efficacy in pyruvate kinase deficiency: 3-year results of the Drive PK study. Congress Presentation Poster, Jun. 12, 2020, 1 page.
Grace et al., European Hematology Association—25th Congress. Mitapivat (AG-348) long-term safety and efficacy in pyruvate kinase deficiency: 3-year results of the Drive PK study. Congress Presentation, Jun. 11, 2020, 1 page. (abstract only).
Grace et al., Safety and efficacy of mitapivat in pyruvate kinase deficiency. N Eng J Med. Sep. 5, 2019;381(10):933-44.
Grace, American Society of Pediatric Hematology/Oncology—32nd Annual Meeting. Clinical research progress in pyruvate kinase deficiency. Congress Presentation, May 1, 2019, 22 pages.
Grace, Boston Children's Hospital—2016 Grand Rounds. Clinical research progress in a rare anemia: New developments in pyruvate kinase deficiency. Congress Presentation, Apr. 5, 2016, 48 pages.
Grace, Brigham & Women's Hematology—2017 Grand Rounds. Clinical research progress in a rare anemia: New developments in pyruvate kinase deficiency. Congress Presentation, Apr. 25, 2017, 50 pages.
Gross, Gordon Research Conference—Enzymes, Coenzymes and Metabolic Pathways 2017. Treatment of rare genetic diseases by small molecule allosteric activators. Congress Presentation, Jul. 19, 2017, 45 pages.
Gross, University of Massachusetts Amherst Graduate School—Presentation in 2018. Treatment of rare genetic diseases by small molecule allosteric activators. Congress Presentation, Apr. 19, 2018, 49 pages.
Jia et al., American Society for Clinical Pharmacology and Therapeutics—119th Annual Meeting. Population pharmacokinetics of AG-348 in healthy volunteers and adult patients with pyruvate kinase deficiency. Congress Presentation Poster, Mar. 21, 2018, 1 page.
Jia et al., American Society for Clinical Pharmacology and Therapeutics—119th Annual Meeting. Population pharmacokinetics of AG-348 in healthy volunteers and adult patients with pyruvate kinase deficiency. Congress Presentation, Mar. 21, 2018, 1 page. (abstract only).
Jones et al., Rare Diseases and Orphan Products Breakthrough Summit 2018. Clinical development of a novel oral activator of red cell pyruvate kinase for the treatment of pyruvate kinase deficiency. Congress Presentation Poster, Oct. 15, 2018, 1 page.
Jones et al., Rare Diseases and Orphan Products Breakthrough Summit 2018. Clinical development of a novel oral activator of red cell pyruvate kinase for the treatment of pyruvate kinase deficiency. Congress Presentation, Oct. 15, 2018, 2 pages. (abstract only).
Jouvin et al., European Hematology Association—23rd Congress. Activate-T: A phase 3, open-label study to evaluate the efficacy and safety of AG-348 in regularly transfused adults with pyruvate kinase deficiency. Congress Presentation Poster, Jun. 15, 2018, 1 page.
Jouvin et al., European Hematology Association—23rd Congress. Activate-T: A phase 3, open-label study to evaluate the efficacy and safety of AG-348 in regularly transfused adults with pyruvate kinase deficiency. Congress Presentation, Jun. 14, 2018, 1 page. (abstract only).
Jouvin et al., European Hematology Association—23rd Congress. Activate: A phase 3, randomized, multicenter, double-blind, placebo-controlled study of AG-348 in adults with pyruvate kinase deficiency who are not regularly transfused. Congress Presentation Poster, Jun. 15, 2018, 1 page.
Jouvin et al., European Hematology Association—23rd Congress. Activate: A phase 3, randomized, multicenter, double-blind, placebo-controlled study of AG-348 in adults with pyruvate kinase deficiency who are not regularly transfused. Congress Presentation, Jun. 14, 2018, 2 pages. (abstract only).
Kanno et al., Japanese Society of Hematology—79th Annual Meeting. AG-348, a pyruvate kinase activator, for pyruvate kinase deficiency: Results from the Drive PK study. Congress Presentation, Oct. 20, 2017, 2 pages. (abstract only).
Kanno et al., Japanese Society of Hematology—79th Annual Meeting. AG-348, a pyruvate kinase activator, for pyruvate kinase deficiency: Results from the Drive PK study. Congress Presentation, Oct. 22, 2017, 15 pages.
Kung et al., AG-348 enhances pyruvate kinase activity in red blood cells from patients with pyruvate kinase deficiency. Blood. Sep. 14, 2017;130(11):1347-56.
Kung et al., American Society of Hematology—56th Annual Meeting. AG-348 activation of pyruvate kinase in vivo enhances red cell glycolysis in mice. Congress Presentation, Dec. 6, 2014, 2 pages. (abstract only).
Kung et al., American Society of Hematology—60th Annual Meeting. Genotype-response correlation in Drive PK, a phase 2 study of

(56) References Cited

OTHER PUBLICATIONS

AG-348 in patients with pyruvate kinase deficiency. Congress Presentation Poster, Dec. 3, 2018, 1 page.

Kung et al., American Society of Hematology—60th Annual Meeting. Genotype-response correlation in Drive PK, a phase 2 study of AG-348 in patients with pyruvate kinase deficiency. Congress Presentation, Dec. 1, 2018, 2 pages. (abstract only).

Kung et al., European Hematology Association—24th Congress. Genotype-response correlation in Drive PK, a phase 2 study of mitapivat (AG-348) in patients with pyruvate kinase deficiency. Congress Presentation Poster, Jun. 14, 2019, 1 page.

Kung et al., European Hematology Association—24th Congress. Genotype-response correlation in Drive PK, a phase 2 study of mitapivat (AG-348) in patients with pyruvate kinase deficiency. Congress Presentation, Jun. 13, 2019, 2 pages. (abstract only).

Kung, Gordon Research Conference—Red Cells. Mechanism of action of the pyruvate kinase activator mitapivat (AG-348) in hematological disease. Congress Presentation, Jul. 17, 2019, 32 pages.

Kuo et al., American Society of Hematology—61st Annual Meeting. Mitapivat (AG-348), an oral PK-R activator, in adults with non-transfusion dependent thalassemia: a phase 2, open-label, multicenter study in progress. Congress Presentation, Dec. 3, 2019, 2 pages. (abstract only).

Kuo et al., American Society of Hematology—61st Annual Meeting. Mitapivat (AG-348), an oral PK-R activator, in adults with non-transfusion-dependent thalassemia: a phase 2, open-label, multicenter study in progress. Congress Presentation Poster, Dec. 8, 2019, 1 page.

Kuo et al., European Hematology Association—25th Congress. Proof of concept for the oral pyruvate kinase activator mitapivat in adults with non-transfusion-dependent thalassemia: Interim results from an ongoing, phase 2, open-label, multicenter study. Congress Presentation, Jun. 11, 2020, 2 pages. (abstract only).

Kuo et al., European Hematology Association—25th Congress. Proof of concept for the oral pyruvate kinase activator mitapivat in adults with non-transfusion-dependent thalassemia: Interim results from an ongoing, phase 2, open-label, multicenter study. Congress Presentation, Jun. 13, 2020, 14 pages.

Kuo et al., European Hematology Association—25th Congress. Summary of Proof of concept for the oral pyruvate kinase activator mitapivat in adults with non-transfusion-dependent thalassemia: Interim results from an ongoing, phase 2, open-label, multicenter study. Congress Presentation, Jun. 17, 2020, 1 page.

Kuo et al., European Hematology Association Scientific Working Group—2019 Scientific Meeting on Red Cell and Iron Metabolism Defects. An ongoing, open-label, multicenter study with the oral pyruvate kinase activator mitapivat (AG-348) in adults with non-transfusion-dependent thalassemia. Congress Presentation, Nov. 7, 2019, 2 pages. (abstract only).

Kuo et al., European Hematology Association Scientific Working Group—2019 Scientific Meeting on Red Cell and Iron Metabolism Defects. An ongoing, open-label, multicenter study with the oral pyruvate kinase activator mitapivat (AG-348) in adults with non-transfusion-dependent thalassemia. Congress Presentation, Nov. 8, 2019, 11 pages.

Layton et al., British Blood Transfusion Society—2018 Annual Conference. Results update from the Drive PK study: Effects of AG-348, a pyruvate kinase activator, in patients with pyruvate kinase deficiency. Congress Presentation Poster, Oct. 4, 2018, 1 page.

Layton et al., British Blood Transfusion Society—2018 Annual Conference. Results update from the Drive PK study: Effects of AG-348, a pyruvate kinase activator, in patients with pyruvate kinase deficiency. Congress Presentation, Oct. 4, 2018, 3 pages. (abstract only).

Layton, European Hematology Association Scientific Working Group—2017 Scientific Meeting on Anemias. New drugs for enzymatic defects. Congress Presentation, Feb. 4, 2017, 23 pages.

Le et al., American Society of Hematology—57th Annual Meeting. Population pharmacokinetics and pharmacodynamics of AG-348 in healthy human volunteers guide dose selection for the treatment of pyruvate kinase deficiency. Congress Presentation Poster, Dec. 5, 2015, 1 page.

Le et al., American Society of Hematology—57th Annual Meeting. Population pharmacokinetics and pharmacodynamics of AG-348 in healthy human volunteers guide dose selection for the treatment of pyruvate kinase deficiency. Congress Presentation, Dec. 5, 2015, 2 pages. (abstract only).

Lynch et al., American Society of Hematology—61st Annual Meeting. Mitapivat (AG-348) in adults with pyruvate kinase deficiency who are regularly transfused: a phase 3, open-label, multicenter study (Activate-T) in progress. Congress Presentation Poster, Dec. 9, 2019, 1 page.

Lynch et al., American Society of Hematology—61st Annual Meeting. Mitapivat (AG-348) in adults with pyruvate kinase deficiency who are regularly transfused: a phase 3, open-label, multicenter, study (Activate-T) in progress. Congress Presentation, Dec. 3, 2019, 2 pages. (abstract only).

Matte et al., European Hematology Association—21st Congress. The pyruvate kinase activator AG-348 improves murine beta-thalassemic anemia and corrects ineffective erythropoiesis. Congress Presentation, Jun. 10, 2016, 17 pages.

Matte et al., European Hematology Association—21st Congress. The pyruvate kinase activator AG-348 improves murine beta-thalassemic anemia and corrects ineffective erythropoiesis. Congress Presentation, Jun. 9, 2016, 2 pages. (abstract only).

Pladson et al., Gordon Research Conference—Red Cells. Clinical development of a novel oral activator of red cell pyruvate kinase for the treatment of pyruvate kinase deficiency. Congress Presentation Poster, Jul. 17, 2019, 1 page.

Pladson et al., Gordon Research Conference—Red Cells. Clinical development of a novel oral activator of red cell pyruvate kinase for the treatment of pyruvate kinase deficiency. Congress Presentation, Jul. 17, 2019, 2 pages. (abstract only).

Rab et al., AG-348 (Mitapivat), an allosteric activator of red blood cell pyruvate kinase, increases enzymatic activity, protein stability, and ATP levels over a broad range of PKLR genotypes. Haematologica. 2021;106(1):238-49.

Rab et al., American Society of Hematology—61st Annual Meeting. Decreased activity and stability of pyruvate kinase in hereditary hemolytic anemia: a potential target for therapy by AG-348 (mitapivat), an allosteric activator of red blood cell pyruvate kinase. Congress Presentation Poster, Dec. 7, 2019, 1 page.

Rab et al., American Society of Hematology—61st Annual Meeting. Decreased activity and stability of pyruvate kinase in hereditary hemolytic anemia: a potential target for therapy by AG-348 (mitapivat), an allosteric activator of red blood cell pyruvate kinase. Congress Presentation, Dec. 3, 2019, 3 pages. (abstract only).

Rab et al., European Hematology Association—24th Congress. Decreased activity and stability of pyruvake kinase in sickle cell disease and thalassemia: A potential target for therapy. Congress Presentation Poster, Jun. 15, 2019, 1 page.

Rab et al., European Hematology Association—24th Congress. Decreased activity and stability of pyruvake kinase in sickle cell disease and thalassemia: A potential target for therapy. Congress Presentation, Jun. 13, 2019, 2 pages. (abstract only).

Rose et al., Club du Globule Rouge et du Fer—2017 Annual Meeting. Allosteric activator of pyruvate kinase first results: Drive PK study Congress Presentation, Sep. 28, 2017, 46 pages.

Rose et al., Societe Francaise d'Hematologie—2017 Annual Congress. Efficacité d'un activateur de la pyruvate kinase (AG -348) sur l'anémie et les paramètres d'hémolyse au cours du déficit en pyruvate kinase : résultats de l'étude Drive PK. Congress Presentation, Mar. 15, 2017, 2 pages. (abstract only).

Rose et al., Societe Francaise d'Hematologie—2017 Annual Congress. Efficacité d'un activateur de la pyruvate kinase (AG-348) sur l'anémie et les paramètres d'hémolyse au cours du déficit en pyruvate kinase : résultats de l'étude Drive PK. Congress Presentation, Mar. 15, 2017, 32 pages.

Uhlig et al., European Hematology Association—24th Congress. Design of a phase 2, open-label, multicenter study of mitapivat

(56) References Cited

OTHER PUBLICATIONS (AG-348) in adults with non-transfusion-dependent thalassemia. Congress Presentation, Jun. 13, 2019, 1 page. (abstract only).

Van Beers et al., American Society of Hematology—61st Annual Meeting. Mitapivat (AG-348) in adults with pyruvate kinase deficiency who are not regularly transfused: a phase 3, randomized, multicenter, double-blind, placebo-controlled study (Activate) in progress. Congress Presentation, Dec. 3, 2019, 3 pages. (abstract only).

Van Beers et al., European Hematology Association Scientific Working Group—2019 Scientific Meeting on Red Cell and Iron Metabolism Defects. Activate: an ongoing phase 3 randomised, double-blind, placebo-controlled study with mitapivat (AG-348) in adults with pyruvate kinase deficiency who are not regularly transfused. Congress Presentation, Nov. 7, 2019, 2 pages. (abstract only).

Van Oirschot et al., European Hematology Association—22nd Congress. Ex vivo treatment of red blood cells from 15 pyruvate kinase (PK)-deficient patients with AG-348, an allosteric activator of PK-R, increases ezymatic activity, protein stability and ATP levels. Congress Presentation Poster, Jun. 22, 2017, 1 page.

Van Oirschot et al., European Hematology Association—22nd Congress. Ex vivo treatment of red blood cells from 15 pyruvate kinase (PK)-deficient patients with AG-348, an allosteric activator of PK-R, increases ezymatic activity, protein stability and ATP levels. Congress Presentation, Jun. 22, 2017, 2 pages. (abstract only).

Yang et al., American Society of Hematology—56th Annual Meeting. Phase 1 single (SAD) and multiple (MAD) ascending dose studies of the safety, tolerability, and pharmacokinetics/pharmacodynamics (PK/PD) of AG-348, a first-in-class allosteric activator of pyruvate kinase-R, in healthy subjects. Congress Presentation Poster, Dec. 6, 2014, 1 page.

Yang et al., ENERCA (2015) 6th European Symposium on Rare Anaemias. Phase 1 multiple ascending dose study of the safety, tolerability and pharmacokinetics/pharmacodynamics of AG-348, a first-in-class allosteric activator pf pyruvate kinase R, in healthy subjects. Congress Presentation, Nov. 21, 2015, 22 pages.

Yang et al., ESH/ENERCA Training Course on Diagnosis and Management of Very Rare Red Cell and Iron Disorders. New treatments of pyruvate kinase deficiency: A Phase 1 multiple ascending dose study of the safety, tolerability, and pharmacokinetics/pharmacodynamics of AG-348, a first-in-class allosteric activator of pyruvate kinase-R, in healthy subjects. Congress Presentation, Jan. 29, 2016, 2 pages. (abstract only).

Yang et al., European Hematology Association—20th Congress. Phase 1 multiple ascending dose study of the safety, tolerability, and pharmacokinetics/pharmacodynamics of AG-348, a first-in-class allosteric activator of pyruvate kinase-R, in healthy subjects. Congress Presentation, Jun. 12, 2015, 19 pages.

Yang et al., European Hematology Association—20th Congress. Phase 1 multiple ascending dose study of the safety, tolerability, and pharmacokinetics/pharmacodynamics of AG-348, a first-in-class allosteric activator of pyruvate kinase-R, in healthy subjects. Congress Presentation, Jun. 13, 2015, 2 pages. (abstract only).

Yang et al., International Drug Discovery Science and Technology—17th Annual Congress. Phase 1 single- and multiple-ascending-dose randomized studies of the safety, pharmacokinetics, and pharmacodynamics of mitapivat (AG-348), a first-in-class allosteric activator of pyruvate kinase R, in healthy volunteers. Congress Presentation, Jul. 25, 2019, 1 page. (abstract only).

Yang et al., International Drug Discovery Science and Technology—17th Annual Congress. Phase 1 single- and multiple-ascending-dose randomized studies of the safety, pharmacokinetics, and pharmacodynamics of mitapivat (AG-348), a first-in-class allosteric activator of pyruvate kinase R, in healthy volunteers. Congress Presentation, Jul. 26, 2019, 19 pages.

Yang et al., Phase 1 single- and multiple-ascending dose randomized studies of the safety, pharmacokinetics, and pharmacodynamics of AG-348, a first-in-class allosteric activator of pyruvate kinase R, in healthy volunteers. Clin Pharmacol Drug Dev. Aug. 9, 2018;8:246-59.

Academic Press, Tools for Purifying the Product: Column Chromatography, Crystallization and Reslurrying. Practical Process Research & Development. Chapter 11, pp. 223-224, Jan. 2000.

Berge et al., Pharmaceutical salts. J Pharm Sci. Jan. 1977;66(1):1-19.

Byrn et al., Pharmaceutical solids: a strategic approach to regulatory considerations. Pharm Res. Jul. 1995;12(7):945-54.

Caira. Crystalline polymorphism of organic compounds. Topics in Current Chemistry. Jan. 1998;198:163-208.

CAS Registry No. 2151847-10-6. 8-Quinolinesulfonamide, N-[4-[[4-(cyclopropylmethyl)-1-piperazinyl]carbonyl]phenyl]-, sulfate, hydrate (2:1:3). 1 page, Dec. 5, 2017.

Hancock et al., Characteristics and significance of the amorphous state in pharmaceutical systems. J Pharma Sci. Jan. 1997;86(1):1-12.

Harwood et al., Organic Reactions/Purification. Experimental Organic Chemistry, Principles and Practice. Blackwell Science. pp. 127-132, Jan. 1989.

STN Accession No. 2014:8. A16A Other Alimentary Tract and Metabolism Products; B3X Other Anti-anaemic Products. 5 pages, Feb. 21, 2020.

Stahl et al., Pharmaceutical salts: properties, selection, and use. Handbook of Pharmaceutical Salts. Jan. 2002;212-14,254,305-6.

International Search Report and Written Opinion for Application No. PCT/US2018/062197, dated Feb. 20, 2019, 24 pages.

International Nonproprietary Names for Pharmaceutical Substances (INN). WHO Drug Information. 2016;30 (4):605-710. Retrieved online at: https://www.who.int/medicines/publications/druginformation/innlists/PL116.pdf.

KEGG Drug: Mitapivat sulfate. Entry No. D11408. Oct. 1, 2008, 1 page. Retrieved online at: https://www.genome.ip/entry/D11408.

Mitapivat sulfate, compound summary. PubChem CID 134693700. Created Aug. 12, 2018, 13 pages. Retrieved online at: https://pubchem.ncbi.nlm.nih.gov/compound/Mitapivat-sulfate.

CRYSTALLINE FORMS OF N-(4-(4-(CYCLOPROPYMETHYL) PIPERAZINE-1-CARBONYL)PHENYL) QUINOLINE-8-SULFONAMIDE

RELATED APPLICATIONS

This application is a 35 U.S.C. § 371 national stage filing of International Application No. PCT/US2018/062197, filed on Nov. 21, 2018 which in turn claims priority to U.S. Provisional Application No. 62/589,822, filed Nov. 22, 2017 and U.S. Provisional Application No. 62/691,709, filed Jun. 29, 2018. The entire contents of each of the aforementioned priority applications are hereby incorporated by reference.

BACKGROUND

Pyruvate kinase deficiency (PKD) is a disease of the red blood cells caused by a deficiency of the pyruvate kinase R (PKR) enzyme due to recessive mutations of PKLR gene (Wijk et al. *Human Mutation*, 2008, 30 (3) 446-453). PKR activators can be beneficial to treat PKD, thalassemia (e.g., beta-thalessemia), abetalipoproteinemia or Bassen-Kornzweig syndrome, sickle cell disease, paroxysmal nocturnal hemoglobinuria, anemia (e.g., congenital anemias (e.g., enzymopathies), hemolytic anemia (e.g. hereditary and/or congenital hemolytic anemia, acquired hemolytic anemia, chronic hemolytic anemia caused by phosphoglycerate kinase deficiency, anemia of chronic diseases, non-spherocytic hemolytic anemia or hereditary spherocytosis). Treatment of PKD is supportive, including blood transfusions, splenectomy, chelation therapy to address iron overload, and/or interventions for other disease-related morbidity. Currently, however, there is no approved medicine that treats the underlying cause of PKD, and thus the etiology of life-long hemolytic anemia.

N-(4-(4-(cyclopropylmethyl)piperazine-1-carbonyl)phenyl)quinoline-8-sulfonamide, herein referred to as Compound 1, is an allosteric activator of red cell isoform of pyruvate kinase (PKR). See e.g., WO 2011/002817 and WO 2016/201227, the contents of which are incorporated herein by reference.

(Compound 1)

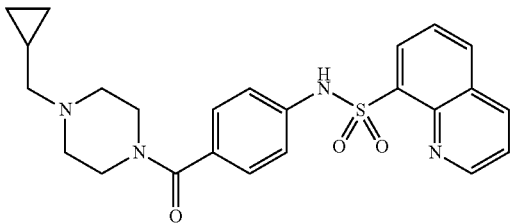

Compound 1 was developed to treat PKD and is currently being investigated in phase 2 clinical trials. See e.g., U.S. clinical trials identifier NCT02476916. Given its therapeutic benefits, there is a need to develop alternative forms of Compound 1 in an effort to facilitate isolation, manufacturing, and formulation development, as well as to enhance storage stability.

SUMMARY

Provided herein are amorphous and crystalline hemisulfate salt forms of a compound having the formula.

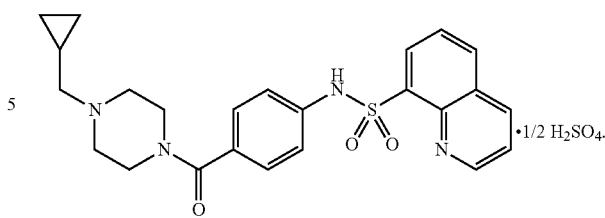

Also provided herein are pharmaceutical compositions comprising the amorphous and crystalline hemisulfate salt forms, methods for their manufacture, and uses thereof for treating conditions associated with pyruvate kinase such as e.g., PKD.

BRIEF DESCRIPTION OF THE FIGURES

FIG. 5 (*ii*) depicts XRPD overlay for crystalline hemisulfate salt Form A and after exposure to phosphorus pentoxide ($P_2O_5$) granules at room temperature and 50° C. for one week, as well as ambient temperature in a vial for 24 hrs. It was observed that there was no change in XRPD pattern at room temperature after one week, but some peaks were slightly shifted at 50° C. However, these peaks shifted back to original positions after exposure to ambient for 24 hrs, indicating these changes were reversible.

FIG. 7(*ii*) depicts the XRPD for crystalline hemisulfate salt Form B before and after dynamic vapor sorption (DVS). After DVS, Form B was converted to a different Form K.

DETAILED DESCRIPTION

Definitions

Figure 1:
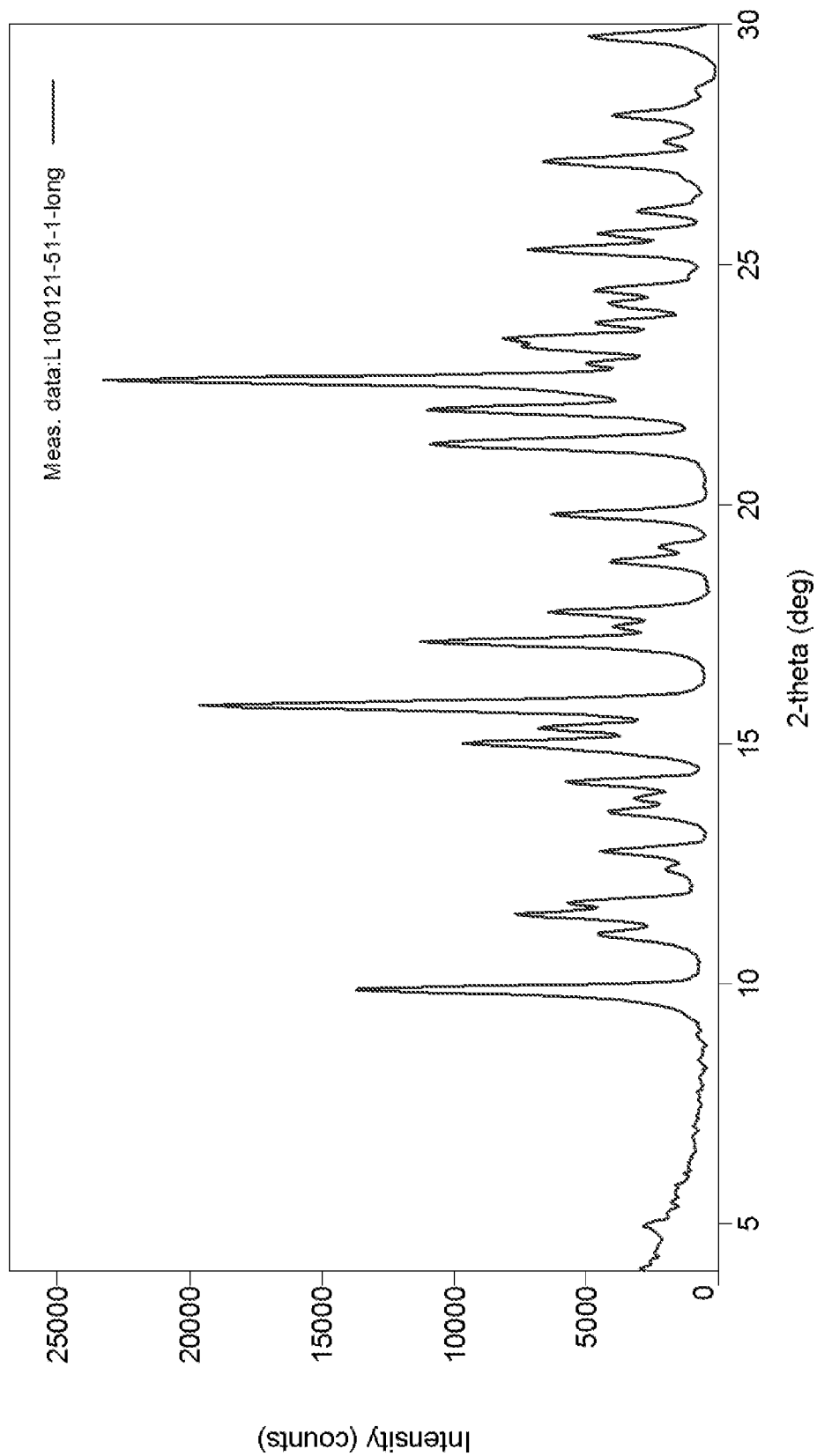
FIG. 1 depicts an X-ray powder diffraction pattern (XRPD) for crystalline hemisulfate salt Form A.

When used alone, the terms "Form A", "Form B", "Form C", "Form D", "Form E", "Form F", "Form G", "Form H", "Form I", and "Form J" refer to the crystalline hemisulfate salt forms A, B, C, D, E, F, G, H, I, and J of Compound 1, respectively. The terms "Form A", "crystalline Form A", and "crystalline hemisulfate salt Form A of Compound 1" are used interchangeably. Similarly, "Form B", "crystalline Form B", and "crystalline hemisulfate salt Form B of Compound 1" are used interchangeably. Similarly, "Form C", "crystalline Form C", and "crystalline hemisulfate salt Form C of Compound 1" are used interchangeably. Similarly, "Form D", "crystalline Form D", and "crystalline hemisulfate salt Form D of Compound 1" are used interchangeably. Similarly, "Form E", "crystalline Form E", and "crystalline hemisulfate salt Form E of Compound 1" are used interchangeably. Similarly, "Form F", "crystalline Form F", and "crystalline hemisulfate salt Form F of Compound 1" are used interchangeably. Similarly, "Form G", "crystalline Form G", and "crystalline hemisulfate salt Form G of Compound 1" are used interchangeably. Similarly, "Form H", "crystalline Form H", and "crystalline hemisulfate salt Form H of Compound 1" are used interchangeably. Similarly, "Form I", "crystalline Form I", and "crystalline hemisulfate salt Form I of Compound 1" are used interchangeably. Similarly, "Form J", and "crystalline Form J", "crystalline hemisulfate salt Form J of Compound 1" are used interchangeably.

"Pattern A", "Pattern B", "Pattern C", "Pattern D", "Pattern E", "Pattern F", "Pattern G", "Pattern H", "Pattern I", and "Pattern J" refer to the X-ray powder diffraction pattern (XRPD) for crystalline hemisulfate salt Form A, B, C, D, E, F, G, H, I and J respectively.

The term "crystalline free base," "free-base crystalline form of Compound 1," "crystalline free base form of Compound 1," and "crystalline free base of Compound 1" are used interchangeably and mean the free base or non-salt form of Compound 1, which is present in a crystalline form.

As used herein, "anhydrous" means that the referenced crystalline form has substantially no water in the crystal lattice e.g., less than 0.1% by weight as determined by Karl Fisher analysis.

The term "amorphous" means a solid that is present in a non-crystalline state or form. Amorphous solids are disordered arrangements of molecules and therefore possess no distinguishable crystal lattice or unit cell and consequently have no definable long range ordering. Solid state ordering of solids may be determined by standard techniques known in the art, e.g., by X-ray powder diffraction (XRPD) or differential scanning calorimetry (DSC). Amorphous solids can also be differentiated from crystalline solids e.g., by birefringence using polarized light microscopy.

As used herein, chemical purity refers to extent by which the disclosed form is free from materials having different chemical structures. Chemical purity of the compound in the disclosed crystal forms means the weight of the compound divided by the sum of the weight of the compound plus materials/impurities having different chemical structures multiplied by 100%, i.e., percent by weight. In one embodiment, the compound in the disclosed crystalline forms has a chemical purity of at least 60%, at least 70%, at least 80%, at least 90%, at least 95%, or at least 99% by weight.

As used herein, "crystalline" refers to a solid form of a compound wherein there exists long-range atomic order in the positions of the atoms. The crystalline nature of a solid can be confirmed, for example, by examination of the X-ray powder diffraction pattern. If the XRPD shows sharp intensity peaks in the XRPD then the compound is crystalline.

The term "solvate" refers to a crystalline compound wherein a stoichiometric or non-stoichiometric amount of solvent, or mixture of solvents, is incorporated into the crystal structure.

The term "hydrate" refers to a crystalline compound where a stoichiometric or non-stoichiometric amount of water is incorporated into the crystal structure. A hydrate is a solvate wherein the solvent incorporated into the crystal structure is water. The term "anhydrous" when used with respect to a compound means substantially no solvent incorporated into the crystal structure.

A single crystalline form of the disclosed crystalline hemisulfate salt means that N-(4-(4-(cyclopropylmethyl) piperazine-1-carbonyl)phenyl)quinoline-8-sulfonamide hemisulfate salt is present as a single crystal or a plurality of crystals in which each crystal has the same crystal form (i.e., Form A, B, C, D, E, F, G, H, I, or J). When the crystal form is defined as a specified percentage of one particular single crystalline form of the compound, the remainder is made up of amorphous form and/or crystalline forms other than the one or more particular forms that are specified. In one embodiment, the crystalline form is at least 60% a single crystalline form, at least 70% a single crystalline form, at least 80% a single crystalline form, at least 90% a single crystalline form, at least 95% a single crystalline form, or at least 99% a single crystalline form by weight. Percent by weight of a particular crystal form is determined by the weight of the particular crystal form divided by the sum weight of the particular crystal, plus the weight of the other crystal forms present plus the weight of amorphous form present multiplied by 100%.

As used herein, "N-(4-(4-(cyclopropylmethyl)piperazine-1-carbonyl)phenyl)quinoline-8-sulfonamide" is used interchangeably with "Compound 1", "free base of Compound 1" with the following structure:

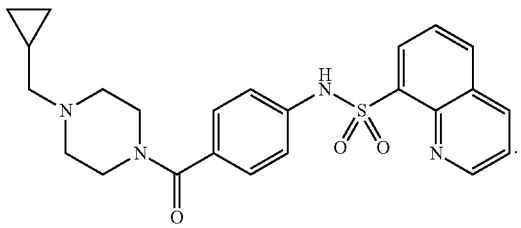 [SMILES: O=C(c1ccc(NS(=O)(=O)c2cccc3cccnc23)cc1)N1CCN(CC2CC2)CC1]

The 2-theta values of the X-ray powder diffraction patterns for the crystalline forms described herein may vary slightly from one instrument to another and also depending on variations in sample preparation and batch to batch variation. Therefore, unless otherwise defined, the XRPD patterns/assignments recited herein are not to be construed as absolute and can vary ±0.2 degrees. The 2-theta values provided herein were obtained using Cu Kα1 radiation.

Temperature values, e.g., for DSC peaks herein may vary slightly from one instrument to another and also depending on variations in sample preparation, batch to batch variation, and environmental factors. Therefore, unless otherwise defined, temperature values recited herein are not to be construed as absolute and can vary ±5 degrees or ±2 degrees.

"Substantially the same XRPD pattern" or "an X-ray powder diffraction pattern substantially similar to" a defined figure means that for comparison purposes, at least 90% of the peaks shown are present. It is to be further understood that for comparison purposes some variability in peak intensities from those shown are allowed, such as ±0.2 degrees.

A "therapeutically effective amount" of a compound described herein is an amount sufficient to provide a therapeutic benefit in the treatment of a condition or to delay or minimize one or more symptoms associated with the condition. The term "therapeutically effective amount" and "effective amount" are used interchangeably. In one aspect, a therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In certain embodiments, a therapeutically effective amount is an amount sufficient for eliciting measurable activation of wild-type or mutant PKR. In certain embodiments, a therapeutically effective amount is an amount sufficient for regulating 2,3-diphosphoglycerate levels in blood in need thereof or for treating pyruvate kinase deficiency (PKD), hemolytic anemia (e.g., chronic hemolytic anemia, hereditary non-spherocytic anemia), sickle cell disease, thalassemia (e.g., alfa thalassemia, beta-thalassemia or non-transfusion-dependent thalassemia), hereditary spherocytosis, hereditary elliptocytosis, abetalipoproteinemia (or Bassen-Kornzweig syndrome), paroxysmal nocturnal hemoglobinuria, acquired hemolytic anemia (e.g., congenital anemias (e.g., enzymopathies)), anemia of chronic diseases or treating diseases or conditions that are associated with increased 2,3-diphosphoglycerate levels (e.g., liver diseases). In certain embodiments, a therapeutically effective amount is an amount sufficient for eliciting measurable activation of wild-type or mutant PKR and for regulating 2,3-diphosphoglycerate levels in blood in need thereof or for treating pyruvate kinase deficiency (PKD), hemolytic anemia (e.g., chronic hemolytic anemia, hereditary non-spherocytic anemia), sickle cell disease, thalassemia (e.g., alfa thalassemia, beta-thalassemia or non-transfusion-dependent thalassemia), hereditary spherocytosis, hereditary elliptocytosis, abetalipoproteinemia (or Bassen-Kornzweig syndrome), paroxysmal nocturnal hemoglobinuria, acquired hemolytic anemia (e.g., congenital anemias (e.g., enzymopathies)), anemia of chronic diseases or treating diseases or conditions that are associated with increased 2,3-diphosphoglycerate levels (e.g., liver diseases). In one aspect, the therapeutically effective amount is the amount required to generate a subject's hemoglobin response of ≥1.0 g/dL (such as ≥1.5 g/dL or ≥2.0 g/dL) increase in Hb concentration from baseline. In one aspect, the subject's baseline Hb concentration is the average of all available Hb concentrations before treatment with a compound described herein. In certain aspects, the therapeutically effective amount is the amount required to reduce the patient's transfusion burden. In one aspect, the therapeutically effective amount is between 0.01-100 mg/kg body weight/day of the provided compound, such as e.g., 0.1-100 mg/kg body weight/day.

As used herein, reduction in transfusion burden means at least 20% reduction in the number of RBC units transfused within at least 5 weeks of treatment. In certain embodiments, the reduction in transfusion burden is ≥33% reduction in the number of RBC units transfused within at least 5 weeks of treatment. In certain embodiments, reduction of transfusion burden is ≥33% reduction in the number of RBC units transfused within at least 10 weeks (e.g., at least 20 weeks or at least 24 weeks) of treatment.

As used herein, sickle cell disease (SCD), Hemoglobin SS disease, and sickle cell anemia are used interchangeably. Sickle cell disease (SCD) is an inherited blood disorder caused by the presence of sickle hemoglobin (HbS). In certain embodiments, subjects with SCD have abnormal hemoglobin, called hemoglobin S or sickle hemoglobin, in their red blood cells. In certain embodiments, people having SCD have at least one abnormal genes causing the body to make hemoglobin S. In certain embodiments, people having SCD have two hemoglobin S genes, Hemoglobin SS.

Thalassemia is an inherited blood disorder in which the normal ratio of α- to β-globin production is disrupted due to a disease-causing variant in 1 or more of the globin genes. In certain embodiments, Alpha-globin aggregates (as found in β-thalassemia) readily precipitate, which disrupts the red blood cell (RBC) membrane and results in oxidative stress. In certain embodiments, Beta-globin tetramers (Hb H, found in α-thalassemia) are generally more soluble, but are still unstable and can form precipitates. The imbalance of the globin chain synthesis can lead to a net reduction in Hb concentrations and has dramatic effects on the survival of RBC precursors, ultimately resulting in their premature destruction in the bone marrow and in extramedullary sites (Cappellini et al, 2014). In certain embodiments, the disorder results in large numbers of red blood cells being destroyed, which leads to anemia. In certain embodiments, the thalassemia is alpha thalassemia. In certain embodiments, the thalassemia is beta thalassemia. In other embodiments, the thalassemia is non-transfusion-dependent thalassemia. In other embodiments, the thalassemia is beta thalassemia intermedia. In other embodiments, the thalassemia is Hb E beta thalassemia. In other embodiments, the thalassemia is beta thalassemia with mutations of 1 or more alfa genes.

The term "activating" as used herein means an agent that (measurably) increases the activity of wild type pyruvate kinase R (wt PKR) or causes wild type pyruvate kinase R (wt PKR) activity to increase to a level that is greater than wt PKR's basal levels of activity or an agent that (measurably) increases the activity of a mutant pyruvate kinase R (mPKR) or causes mutant pyruvate kinase R (mPKR) activity to increase to a level that is greater than that mutant PKR's basal levels of activity, for examples, to a level that is 20%, 40%, 50%, 60%, 70%, 80%, 90% or 100% of the activity of wild type PKR.

The term "packed red blood cells" or PRBCs as used herein refer to red blood cells made from a unit of whole blood by centrifugation and removal of most of the plasma. In certain embodiments, a PRBC unit has a hematocrit of at least about 95%. In certain embodiments, a PRBC unit has a hematocrit of at least about 90%. In certain embodiments, a PRBC unit has a hematocrit of at least about 80%. In certain embodiments, a PRBC unit has a hematocrit of at least about 70%. In certain embodiments, a PRBC unit has a hematocrit of at least about 60%. In certain embodiments, a PRBC unit has a hematocrit of at least about 50%. In certain embodiments, a PRBC unit has a hematocrit of at least about 40%. In certain embodiments, a PRBC unit has a hematocrit of at least about 30%. In certain embodiments, a PRBC unit has a hematocrit of at least about 20%. In certain embodiments, a PRBC unit has a hematocrit of at least about 10%.

The terms "treatment," "treat," and "treating" refer to reversing, alleviating, reducing the likelihood of developing, or inhibiting the progress of a disease or disorder, or one or more symptoms thereof, as described herein. In some embodiments, treatment may be administered after one or more symptoms have developed, i.e., therapeutic treatment. In other embodiments, treatment may be administered in the absence of symptoms. For example, treatment may be administered to a susceptible individual prior to the onset of symptoms (e.g., in light of a history of symptoms and/or in light of genetic or other susceptibility factors), i.e., prophylactic treatment. Treatment may also be continued after symptoms have resolved, for example to reduce the likelihood of or delay their recurrence.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment. In certain embodiments, the term "subject" refers to a human subject in need of treatment of a disease. In certain embodiments, the term "subject" refers to a human subject in need of treatment of PKD. In certain embodiments, the term "subject" refers to a human subject in need of treatment of thalassemia. In certain embodiments, the term "subject" refers to a human subject in need of treatment of sickle cell disease. In certain embodiments, the term "subject" refers to a human adult over 18 years old in need of treatment of a disease. In certain embodiments, the term "subject" refers to a human child no more than 18 years old in need of treatment of a disease. In certain embodiments, the subject is a patient in need of regular blood transfusion.

As used here, the regular blood transfusion refers to at least 4 transfusion episodes in a 52-week period prior to the treatment. In certain embodiments, the regular blood transfusion refers to at least 5 transfusion episodes in a 52-week period prior to the treatment. In certain embodiments, the regular blood transfusion refers to at least 6 transfusion episodes in a 52-week period prior to the treatment. In certain embodiments, the regular blood transfusion refers to at least 7 transfusion episodes in a 52-week period prior to the treatment. In certain embodiments, the subject with a least one of the indications selected from the sickle cell disease, thalassemia, PKD under regular transfusion, and non-transfusion dependent PKD, has not been exposed to sotatercept (ACE-011), luspatercept (ACE-536), ruxolitinib, or gene therapy. In certain embodiments, such subject is not taking inhibitors of cytochrome P450 (CYP)3A4, strong inducers of CYP3A4, strong inhibitors of P-glycoprotein (P-gp), or digoxin. In certain embodiments, such subject is not receiving chronic anticoagulant therapy, anabolic steroids, hematopoietic stimulating agents (eg, erythropoietins, granulocyte colony stimulating factors, thrombopoietins), or allergic to sulfonamides.

The term "pharmaceutically acceptable carrier" refers to a non-toxic carrier, adjuvant, or vehicle that does not adversely affect the pharmacological activity of the compound with which it is formulated, and which is also safe for human use.

As used herein, the terms "about" and "approximately" when used in combination with a numeric value or range of values used to characterize a particular crystal form, amorphous form, or mixture thereof of a compound mean the value or range of values may deviate to an extent deemed reasonable to one of ordinary skill in the art while describing the particular crystal form, amorphous form, or mixture thereof.

Compounds

Provided herein is a crystalline Form A of a hemisulfate salt of a compound having the formula (I):

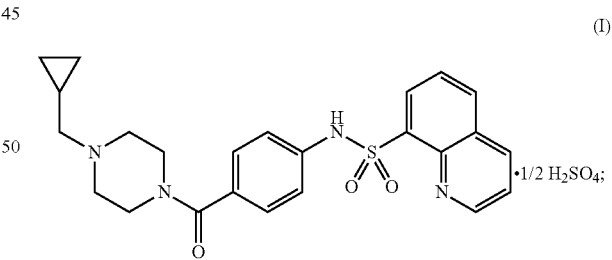

(I)

wherein the hemisulfate salt of the compound in crystalline Form A is a sesquihydrate.

As used herein, crystalline Form A is a hemisulfate sesquihydrate of compound 1, N-(4-(4-(cyclopropylmethyl)piperazine-1-carbonyl)phenyl)quinoline-8-sulfonamide. It is to be understood that crystalline Form A can be named "1-(cyclopropylmethyl)-4-(4-(quinoline-8-sulfonamido)benzoyl)piperazin-1-ium hemisulfate sesquihydrate" having Formula A, or alternatively "1-(cyclopropylmethyl)-4-(4-(quinoline-8-sulfonamido)benzoyl)piperazin-1-ium sulfate trihydrate" having Formula B as shown below:

Formula A

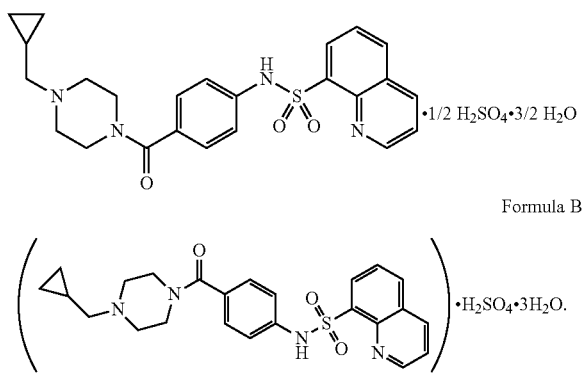

Formula B

It is to be understood that crystalline Form A can be referred to either Formula A or Formula B interchangeably.

As used herein, "hemisulfate" means the stoichiometric ratio of compound 1 to $H_2SO_4$ is 2:1 in a crystalline form (i.e. a crystalline form contains two molecules of compound 1 per one molecule of $H_2SO_4$).

As used herein, "sesquihyrate" or "trihydrate" means the stoichiometric ratio of compound 1 to $H_2O$ is 2:3 in crystalline Form A (i.e. crystalline Form A contains two molecules of compound 1 per three molecules of water).

Figure 2:
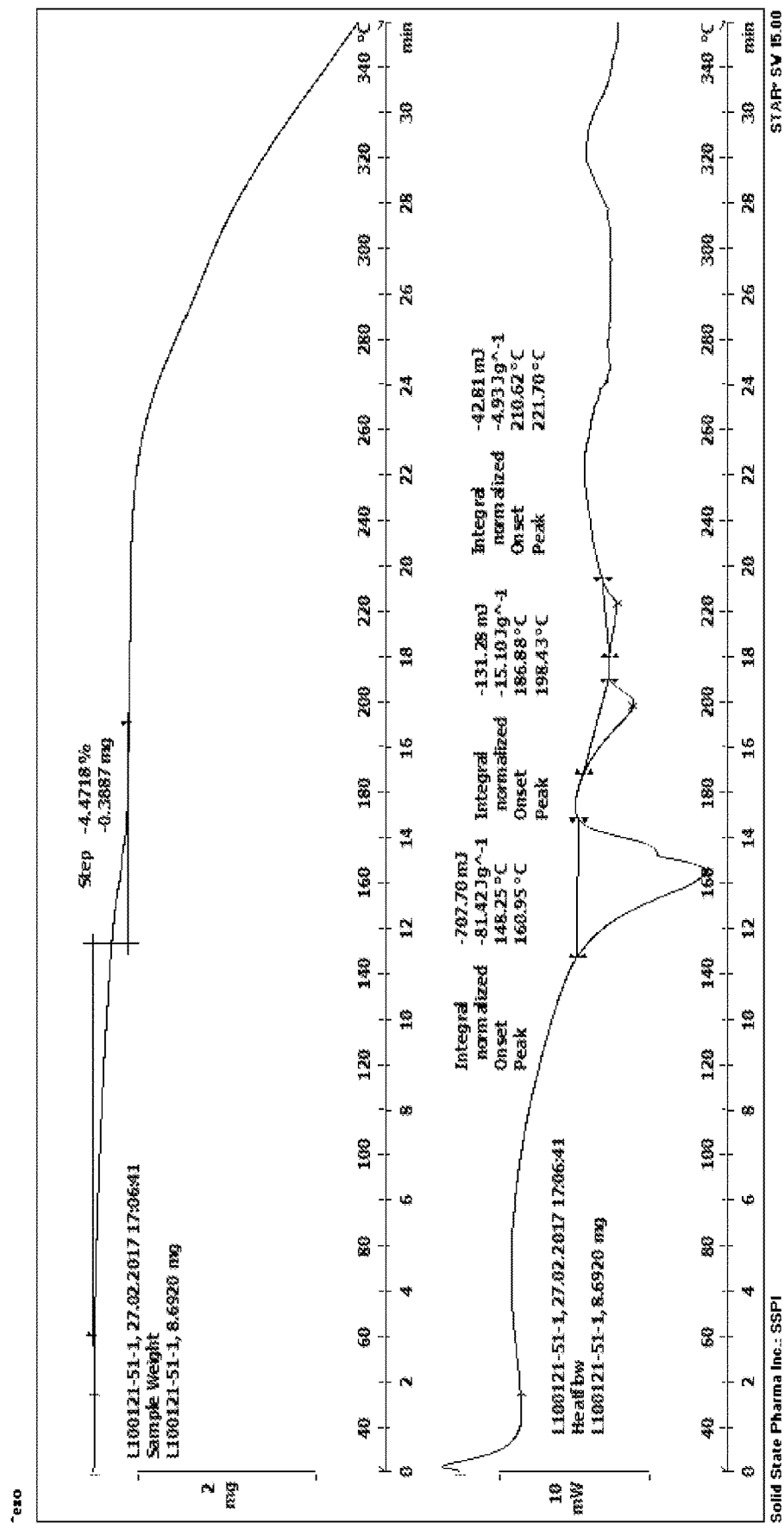
FIG. 2 depicts the combined thermogravimetric analysis (TGA) thermogram and differential scanning calorimetry (DSC) thermogram for crystalline hemisulfate salt Form A.
Figure 3:
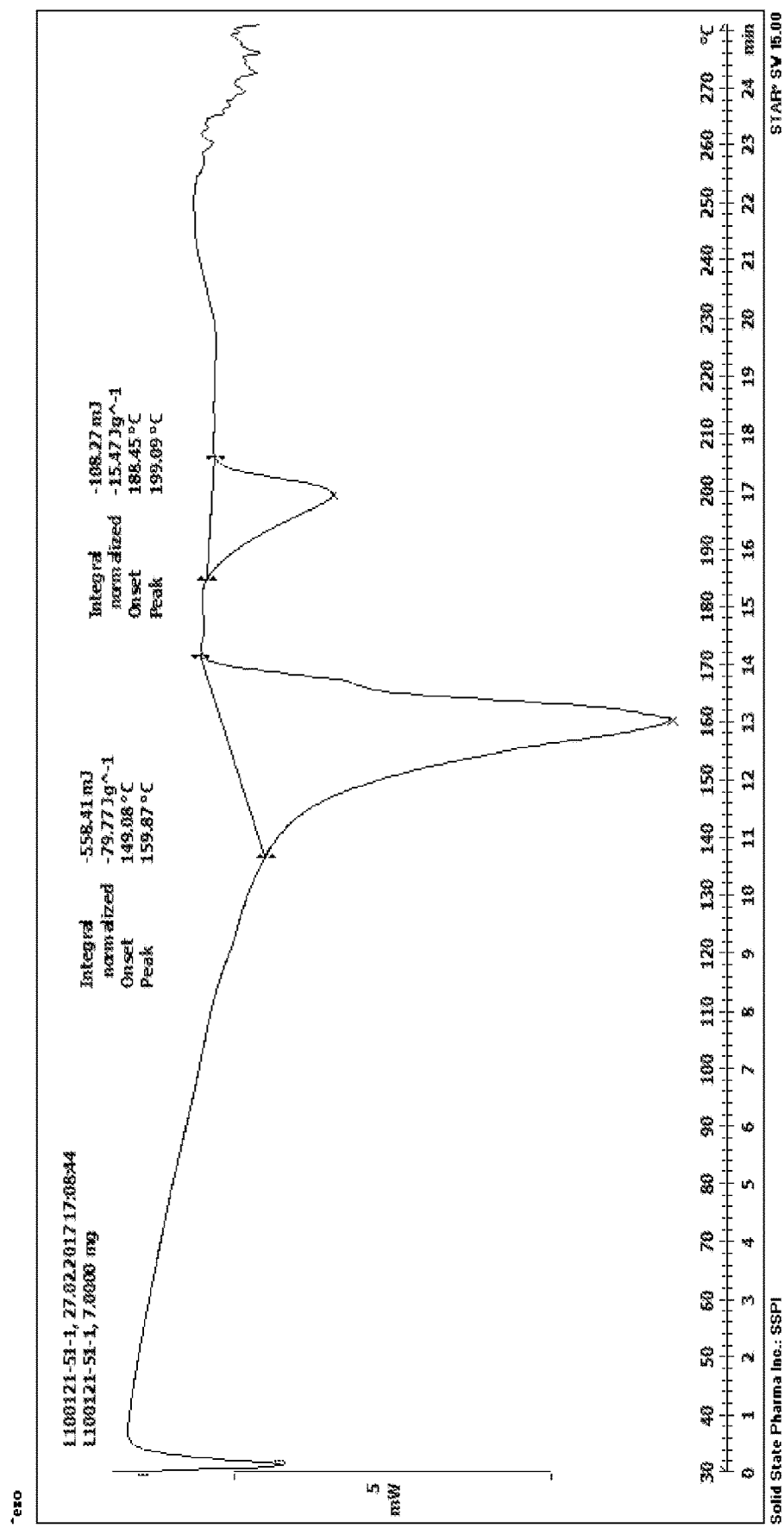
FIG. 3 depicts the differential scanning calorimetry (DSC) thermogram for crystalline hemisulfate salt Form A

In one aspect, crystalline Form A is characterized by x-ray powder diffraction peaks at 2Θ angles (±0.2°) 9.9°, 15.8°, and 22.6°. In certain embodiments, crystalline Form A is characterized by x-ray powder diffraction peaks at 2Θ angles (±0.2°) 9.9°, 15.8°, and 22.6° and at least one additional x-ray powder diffraction peak at 2Θ angles (±0.2°) selected from 15.0°, 17.1°, 21.3°, and 21.9°. In certain embodiments, crystalline Form A is characterized by x-ray powder diffraction peaks at 2Θ angles (±0.2°) 9.9°, 15.8°, and 22.6°; and at least two additional x-ray powder diffraction peaks at 2Θ angles (±0.2°) selected from 15.0°, 17.1°, 21.3°, and 21.9°. In yet another alternative, crystalline Form A is characterized by x-ray powder diffraction peaks at 2Θ angles (±0.2°) 9.9°, 15.8°, and 22.6°; and at least three additional x-ray powder diffraction peaks at 2Θ angles (±0.2°) selected from 15.0°, 17.1°, 21.3°, and 21.9°. In certain embodiments, crystalline Form A is characterized by x-ray powder diffraction peaks at 2Θ angles (±0.2°) 9.9°, 15.0°, 15.8°, 17.1°, 21.3°, 21.9°, and 22.6°. In certain embodiments, crystalline Form A is characterized by x-ray powder diffraction peaks at 2Θ angles (±0.2°) 9.9°, 11.4°, 15.0°, 15.3°, 15.8°, 17.1°, 17.7°, 21.3°, 21.9°, 22.6°, and 23.5°. In certain embodiments, crystalline Form A is characterized by x-ray powder diffraction peaks at 2Θ angles (±0.2°) 4.9°, 9.9°, 11.0°, 11.4°, 11.7°, 12.3°, 12.8°, 13.6°, 13.9°, 14.2°, 15.0°, 15.3°, 15.8°, 17.1°, 17.4°, 17.7°, 18.8°, 19.1°, 19.8°, 21.3°, 21.9°, 22.6°, 23.0°, 23.2°, 23.5°, 23.8°, 24.1°, 24.5°, 25.3°, 25.6°, 26.1°, 27.1°, 28.1°, and 29.8°. In certain embodiments, crystalline Form A is characterized by an X-ray powder diffraction pattern substantially similar to FIG. 1. In yet another alternative, crystalline Form A is characterized by a differential scanning calorimetry (DSC) thermograph comprising endotherm peaks at about 159° C.±5° C. and 199° C.±5° C. In yet another alternative, crystalline Form A is characterized by a differential scanning calorimetry (DSC) thermogram substantially similar to the one depicted in FIG. 2. In yet another alternative, crystalline Form A is characterized by a thermogravimetric analysis (TGA) thermogram comprising a weight loss of about 4.5±0.5% up to 180° C.±2° C. In yet another alternative, crystalline Form A is characterized by a thermogravimetric analysis (TGA) thermogram substantially similar to the one depicted in FIG. 2. In yet another alternative, crystalline Form A is characterized by a DSC substantially similar to the one depicted in FIG. 3.

As discussed in greater detail in the Examples, crystalline Form A of a hemisulfate salt of a compound having the formula (I) was found to have a variety of favorable physicochemical properties, including high crystallinity, stability in multiple solvent systems (e.g. especially containing water), relatively small particle size (e.g. below 20 µm under microscope so as to potentially avoid the subsequent micronization), and stability in humidity (e.g. at least 20% RH or at least a water activity of 0.2), and demonstrate favorable plasma concentration-time profiles and pharmacokinetic parameters.

Also provided herein is a crystalline Form B of a hemisulfate salt of a compound having the formula:

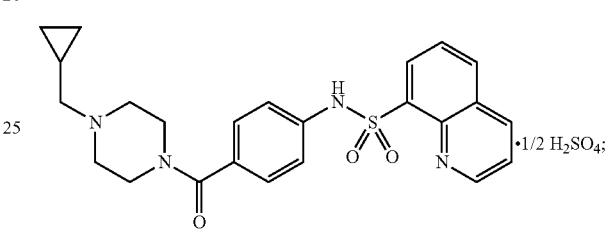

wherein the hemisulfate salt of the compound in crystalline Form B is an ethanol solvate.

In one aspect, crystalline Form B is characterized by at least three x-ray powder diffraction peaks at 2Θ angles (±0.2°) selected from 9.9°, 10.6°, 12.7°, 15.7°, 16.9°, 22.0°, and 22.5°. Alternatively, crystalline Form B is characterized by at least four x-ray powder diffraction peaks at 2Θ angles (±0.2°) selected from 9.9°, 10.6°, 12.7°, 15.7°, 16.9°, 22.0°, and 22.5°. In another alternative, crystalline Form B is characterized by at five three x-ray powder diffraction peaks at 2Θ angles (±0.2°) selected from 9.9°, 10.6°, 12.7°, 15.7°, 16.9°, 22.0°, and 22.5°. In yet another alternative, crystalline Form B is characterized by at least six x-ray powder diffraction peaks at 2Θ angles (±0.2°) selected from 9.9°, 10.6°, 12.7°, 15.7°, 16.9°, 22.0°, and 22.5°. In yet another alternative, crystalline Form B is characterized by x-ray powder diffraction peaks at 2Θ angles (±0.2°) 9.9°, 10.6°, 12.7°, 15.7°, 16.9°, 22.0°, and 22.5°. In yet another alternative, crystalline Form B is characterized by x-ray powder diffraction peaks at 2Θ angles (±0.2°) 9.9°, 10.6°, 12.7°, 13.9°, 14.6°, 15.7°, 16.9°, 22.0°, 22.5°, and 27.6°. In yet another alternative, crystalline Form B is characterized by x-ray powder diffraction peaks at 2Θ angles (±0.2°) 7.0°, 7.8°, 9.9°, 10.6°, 11.7°, 12.7°, 13.1°, 13.5°, 13.9°, 14.6°, 14.9°, 15.3°, 15.7°, 16.1°, 16.9°, 17.6°, 19.3°, 19.7°, 20.7°, 21.2°, 22.0°, 22.5°, 23.3°, 24.0°, 24.7°, 25.1°, 25.7°, 26.1°, 27.2°, 27.6°, 28.4°, 29.3°, and 29.8°. In yet another alternative, crystalline Form B is characterized by an X-ray powder diffraction pattern substantially similar to FIG. 6. In yet another alternative, crystalline Form B is characterized by a TGA or DSC pattern substantially similar to FIG. 7. In yet another alternative, crystalline Form B is characterized by a differential scanning calorimetry (DSC) thermograph comprising endotherm peaks at about 154±5° C. In yet another alternative, crystalline Form B is characterized by a TGA comprising a weight loss of about 4.3±0.5% up to 200° C.±2° C.

Also provided herein is a crystalline Form C of a hemisulfate salt of a compound having the formula:

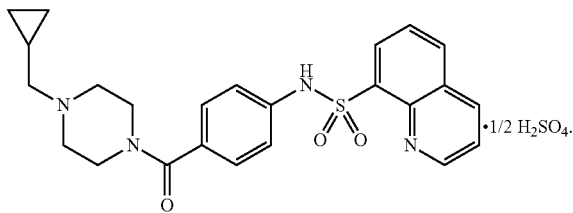 [SMILES: O=C(c1ccc(NS(=O)(=O)c2cccc3cccnc23)cc1)N1CCN(CC2CC2)CC1]

In one aspect, crystalline Form C is characterized by x-ray powder diffraction peaks at 2Θ angles (±0.2°) 6.9°, 10.4°, and 12.0°.

Also provided herein is a crystalline Form D of a hemisulfate salt of a compound having the formula:

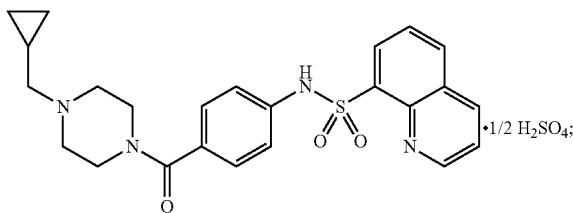 [SMILES: O=C(c1ccc(NS(=O)(=O)c2cccc3cccnc23)cc1)N1CCN(CC2CC2)CC1]

wherein the hemisulfate salt of the compound in Form D is anhydrous.

Figure 8:
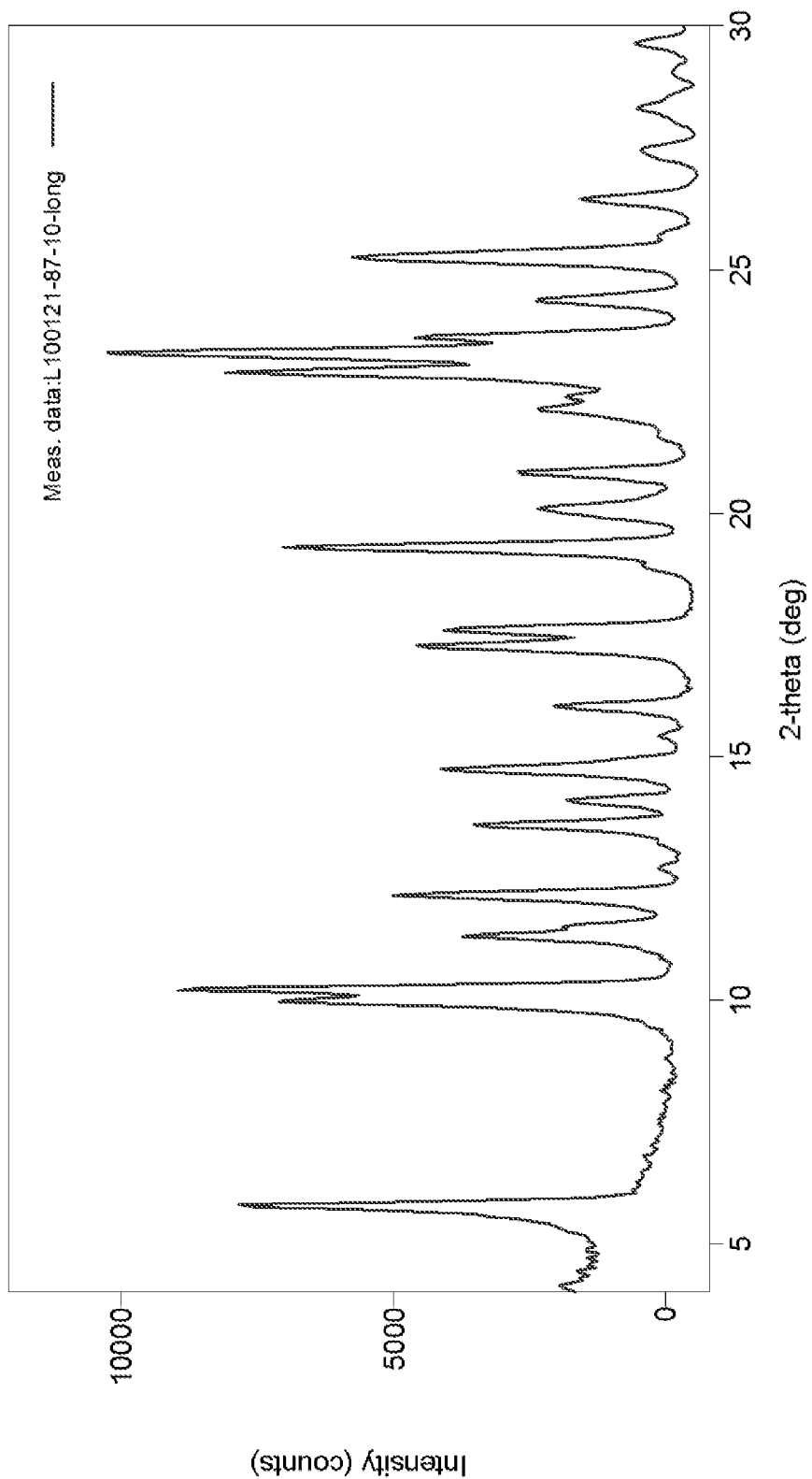
FIG. 8 depicts an X-ray powder diffraction pattern (XRPD) for crystalline hemisulfate salt Form D.

In one aspect, crystalline Form D is characterized by at least three x-ray powder diffraction peaks at 2Θ angles (±0.2°) selected from 5.8°, 10.0°, 10.2°, 19.3°, 22.9°, 23.3°, and 25.2°. Alternatively, crystalline Form D is characterized by at least four x-ray powder diffraction peaks at 2Θ angles (±0.2°) selected from 5.8°, 10.0°, 10.2°, 19.3°, 22.9°, 23.3°, and 25.2°. In another alternative, crystalline Form D is characterized by at least five x-ray powder diffraction peaks at 2Θ angles (±0.2°) selected from 5.8°, 10.0°, 10.2°, 19.3°, 22.9°, 23.3°, and 25.2°. In yet another alternative, crystalline Form D is characterized by at least six x-ray powder diffraction peaks at 2Θ angles (±0.2°) selected from 5.8°, 10.0°, 10.2°, 19.3°, 22.9°, 23.3°, and 25.2°. In yet another alternative, crystalline Form D is characterized by x-ray powder diffraction peaks at 2Θ angles (±0.2°) 5.8°, 10.0°, 10.2°, 19.3°, 22.9°, 23.3°, and 25.2°. In yet another alternative, crystalline Form D is characterized by x-ray powder diffraction peaks at 2Θ angles (±0.2°) 5.8°, 10.0°, 10.2°, 12.2°, 17.3°, 17.6°, 19.3°, 22.9°, 23.3°, 23.6°, and 25.2°. In yet another alternative, crystalline Form D is characterized by x-ray powder diffraction peaks at 2Θ angles (±0.2°) 5.8°, 10.0°, 10.2°, 11.3°, 11.5°, 12.2°, 13.6°, 14.1°, 14.7°, 15.4°, 16.0°, 17.3°, 17.6°, 19.3°, 20.0°, 20.8°, 22.1°, 22.9°, 23.3°, 23.6°, 24.4°, 25.2°, 26.4°, 27.4°, 28.3°, and 29.6°. In yet another alternative, crystalline Form D is characterized by an X-ray powder diffraction pattern substantially similar to FIG. 8. In yet another alternative, crystalline Form D is characterized by a differential scanning calorimetry (DSC) pattern having a peak at 239.0° C.±2° C. In yet another alternative, crystalline Form D is characterized by a DSC substantially similar to FIG. 9. In yet another alternative, crystalline Form D, is characterized by a TGA comprising a weight loss of about 0.62±0.5% up to 220° C.±2° C. In yet another alternative, crystalline Form D is characterized by a TGA substantially similar to FIG. 9.

Also provided is a crystalline Form E of a hemisulfate salt of a compound having the formula:

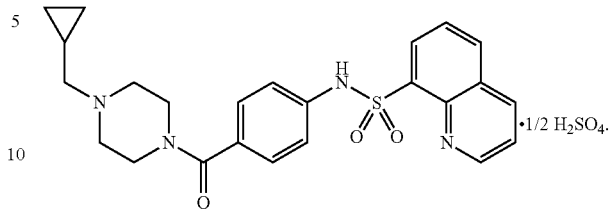

In one aspect, crystalline Form E is characterized by x-ray powder diffraction peaks at 2Θ angles (±0.2°) selected from 4.6°, 9.0°, 13.5°, and 22.5°. In another aspect, crystalline Form E is characterized by x-ray powder diffraction peaks at 2Θ angles (±0.2°) 4.6°, 9.0°, 13.5°, 15.1°, 18.5°, 21.7°, and 22.5°. In another alternative, crystalline Form E is characterized by x-ray powder diffraction peaks at 2Θ angles (±0.2°) 4.6°, 9.0°, 9.9°, 11.0°, 13.5°, 15.1°, 15.8°, 18.5°, 19.8°, 20.4°, 21.7°, 22.5°, and 28.1°. In yet another alternative, crystalline Form E is characterized by an X-ray powder diffraction pattern substantially similar to FIG. 11.

Also provided herein is a crystalline Form F of a hemisulfate salt of a compound having the formula:

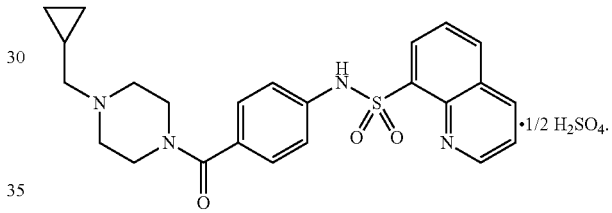

In one aspect, crystalline Form F is characterized by x-ray powder diffraction peaks at 2Θ angles (±0.2°) selected from 5.0°, 9.9°, and 14.7°. Alternatively, crystalline Form F is characterized by x-ray powder diffraction peaks at 2Θ angles (±0.2°) selected from 5.0°, 9.9°, 14.7°, 16.5°, 19.6°, 21.6°, and 24.4°. In another alternative, crystalline Form F is characterized by x-ray powder diffraction peaks at 2Θ angles (±0.2°) 5.0°, 9.9°, 11.1°, 14.7°, 16.5°, 19.6°, 21.6°, 22.8°, and 24.4°. In yet another alternative, crystalline Form F is characterized by an X-ray powder diffraction pattern substantially similar to FIG. 12. In yet another alternative, crystalline Form F, is characterized by a DSC pattern having a peak at 101.0° C.±2° C. In yet another alternative, crystalline Form F, is characterized by a TGA comprising a weight loss of about 8.8±0.5% up to 182° C.±2° C. In yet another alternative, crystalline Form F is characterized by a TGA or DSC substantially similar to FIG. 13.

Also provided is crystalline Form G of a hemisulfate salt of a compound having the formula:

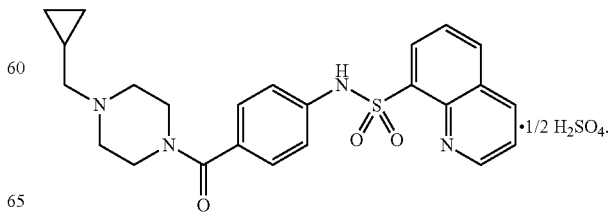

In one aspect, crystalline Form G is characterized by x-ray powder diffraction peaks at 2Θ angles (±0.2°) selected from 4.7°, 9.4°, and 14.1°. Alternatively, crystalline Form G is characterized by x-ray powder diffraction peaks at 2Θ angles (±0.2°) selected from 4.7°, 9.4°, 11.0°, 14.1°, 18.9°, 21.2°, and 23.8°. In another alternative, crystalline Form G is characterized by x-ray powder diffraction peaks at 2Θ angles (±0.2°) 4.7°, 9.4°, 11.0°, 13.3°, 14.1°, 15.9°, 16.2°, 18.9°, 21.2°, 22.8°, 23.8°, 26.7°, and 28.5°. In yet another alternative, crystalline Form G is characterized by an X-ray powder diffraction pattern substantially similar to FIG. 14. In yet another alternative, crystalline Form G, is characterized by a DSC pattern having a peak at 156.7° C.±2° C. In yet another alternative, crystalline Form G, is characterized by a TGA comprising a weight loss of about 2.6±0.5% up to 176° C.±2° C. In yet another alternative, crystalline Form G is characterized by a TGA or DSC substantially similar to FIG. 15.

Also provided is a crystalline Form H of a hemisulfate salt of a compound having the formula:

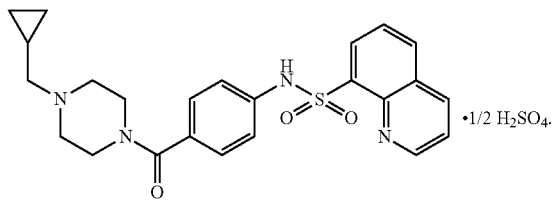 [SMILES: O=C(c1ccc(NS(=O)(=O)c2cccc3cccnc23)cc1)N1CCN(CC2CC2)CC1]

In one aspect, crystalline Form H is characterized by at least three x-ray powder diffraction peaks at 2Θ angles (±0.2°) selected from 4.6°, 7.4°, 9.2°, 11.1°, 13.5°, 14.9°, and 22.3°. Alternatively, crystalline Form H is characterized by at least four x-ray powder diffraction peaks at 2Θ angles (±0.2°) selected from 4.6°, 7.4°, 9.2°, 11.1°, 13.5°, 14.9°, and 22.3°. In another alternative, crystalline Form H is characterized by at least five x-ray powder diffraction peaks at 2Θ angles (±0.2°) selected from 4.6°, 7.4°, 9.2°, 11.1°, 13.5°, 14.9°, and 22.3°. In yet another alternative, crystalline Form H is characterized by at least six x-ray powder diffraction peaks at 2Θ angles (±0.2°) selected from 4.6°, 7.4°, 9.2°, 11.1°, 13.5°, 14.9°, and 22.3°. In yet another alternative, crystalline Form H is characterized by x-ray powder diffraction peaks at 2Θ angles (±0.2°) 4.6°, 7.4°, 9.2°, 11.1°, 13.5°, 14.9°, and 22.3°. In yet another alternative, crystalline Form H is characterized by x-ray powder diffraction peaks at 2Θ angles (±0.2°) 4.6°, 5.4°, 7.4°, 9.2°, 10.3°, 11.1°, 13.5°, 13.8°, 14.9°, 16.9°, 17.6°, 18.4°, 19.5°, 20.7°, 22.3°, 22.9°, 23.4°, 24.1°, 24.8°, 26.5°, 27.2°, and 29.5°. In yet another alternative, crystalline Form H is characterized by an X-ray powder diffraction pattern substantially similar to FIG. 16.

Also provided is a crystalline Form I of a hemisulfate salt of a compound having the formula:

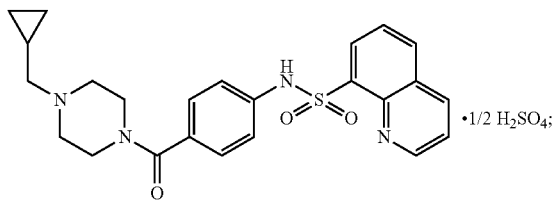 [SMILES: O=C(c1ccc(NS(=O)(=O)c2cccc3cccnc23)cc1)N1CCN(CC2CC2)CC1]

wherein the hemisulfate salt of the compound in crystalline Form I is an ethanol solvate.

In one aspect, crystalline Form I is characterized by x-ray powder diffraction peaks at 2Θ angles (±0.2°) 6.7°, 9.5°, and 19.7°. Alternatively, crystalline Form I is characterized by x-ray powder diffraction peaks at 2Θ angles (±0.2°) 6.7°, 9.5°, and 19.7°; and at least one additional x-ray powder diffraction peak at 2Θ angles (±0.2°) selected from 9.9°, 12.6°, 15.8°, 21.9°, and 22.3°. In another alternative, crystalline Form I is characterized by x-ray powder diffraction peaks at 2Θ angles (±0.2°) 6.7°, 9.5°, and 19.7°; and at least two additional x-ray powder diffraction peaks at 2Θ angles (±0.2°) selected from 9.9°, 12.6°, 15.8°, 21.9°, and 22.3°. In yet another alternative, crystalline Form I is characterized by x-ray powder diffraction peaks at 2Θ angles (±0.2°) 6.7°, 9.5°, and 19.7°; and at least three additional x-ray powder diffraction peak at 2Θ angles (±0.2°) selected from 9.9°, 12.6°, 15.8°, 21.9°, and 22.3°. In yet another alternative, crystalline Form I is characterized by x-ray powder diffraction peaks at 2Θ angles (±0.2°) 6.7°, 9.5°, 9.9°, 12.6°, 15.8°, 19.7°, 21.9°, and 22.3°. In yet another alternative, crystalline Form I is characterized by x-ray powder diffraction peaks at 2Θ angles (±0.2°) 6.7°, 7.7°, 9.5°, 9.9°, 10.5°, 11.6°, 12.6°, 13.4°, 13.8°, 14.3°, 15.2°, 15.8°, 16.8°, 17.2°, 19.0°, 19.7°, 20.5°, 20.9°, 21.9°, 22.3°, 23.9°, 24.6°, 25.5°, 26.0°, 27.5°, 28.3°, and 29.3°. In yet another alternative, crystalline Form I is characterized by an X-ray powder diffraction pattern substantially similar to FIG. 17. In yet another alternative, crystalline Form I, is characterized by a DSC pattern having a peak at 134.7° C.±2° C. In yet another alternative, crystalline Form I, is characterized by a TGA comprising a weight loss of about 6.9±0.5% up to 180° C.±2° C. In yet another alternative, crystalline Form I is characterized by a TGA or DSC substantially similar to FIG. 18.

Also provided is a crystalline Form J of a hemisulfate salt of a compound having the formula:

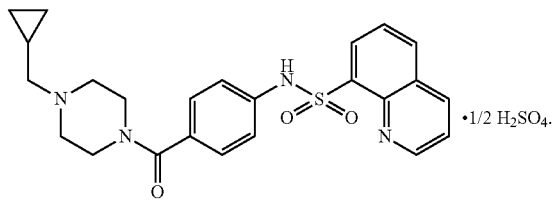 [SMILES: O=C(c1ccc(NS(=O)(=O)c2cccc3cccnc23)cc1)N1CCN(CC2CC2)CC1]

In one aspect, crystalline Form J is characterized by x-ray powder diffraction peaks at 2Θ angles (±0.2°) selected from 12.4°, 13.2°, 14.6°, 20.4°, and 23.7°. Alternatively, crystalline Form J is characterized by x-ray powder diffraction peaks at 2Θ angles (±0.2°) selected from 12.4°, 13.2°, 14.6°, 15.7°, 20.4°, 23.3°, and 23.7°. In another alternative, crystalline Form J is characterized by x-ray powder diffraction peaks at 2Θ angles (±0.2°) 12.4°, 13.2°, 14.6°, 15.7°, 20.4°, 22.0°, 23.3°, 23.7°, and 28.0°. In another alternative, crystalline Form J is characterized by an X-ray powder diffraction pattern substantially similar to FIG. 19.

Also provided herein is a free-base crystalline form of Compound 1 having the formula:

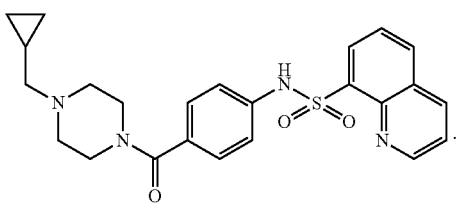 [SMILES: O=C(c1ccc(NS(=O)(=O)c2cccc3cccnc23)cc1)N1CCN(CC2CC2)CC1]

In one aspect, the free-base crystalline form of Compound 1 is characterized by x-ray powder diffraction peaks at 2Θ angles (±0.2°) selected from 6.9°, 13.5°, 19.8°, and 20.3°. Alternatively, the free-base crystalline form of Compound 1 is characterized by x-ray powder diffraction peaks at 2Θ angles (±0.2°) selected from 6.9°, 13.5°, 19.8°, 20.3°, and 25.7°. In another alternative the free-base crystalline form of Compound 1 is characterized by x-ray powder diffraction peaks at 2Θ angles (±0.2°) 6.9°, 13.5°, 15.7°, 15.9°, 19.8°, 20.3°, 23.6°, and 25.7°. In yet another alternative, the free-base crystalline form of Compound 1 is characterized by an X-ray powder diffraction pattern substantially similar to FIG. 25.

Also provided herein is an amorphous Form of a hemisulfate salt of a compound having the formula:

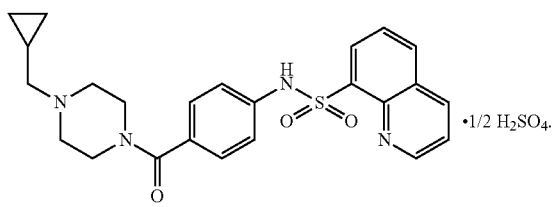 [SMILES: O=C(c1ccc(NS(=O)(=O)c2cccc3cccnc23)cc1)N1CCN(CC2CC2)CC1]

In one aspect, the compounds described herein are at least 60% a single crystalline form, at least 70% a single crystalline form, at least 80% a single crystalline form, at least 90% a single crystalline form, at least 95% a single crystalline form, or at least 99% a single crystalline form by weight.

In one aspect, the compounds described herein have a chemical purity of at least 60%, at least 70%, at least 80%, at least 90%, at least 95%, or at least 99% by weight.

In one aspect, the compounds described herein are substantially free of amorphous forms, i.e., less than 10% of the amorphous form is present e.g., less than 5%, less than 3%, less than 2%, or less than 1% of the amorphous form is present.

Also provided are processes for making the disclosed crystalline and amorphous forms.

In one aspect, provided herein is a method of forming crystalline Form A, the method comprising reacting Compound 1:

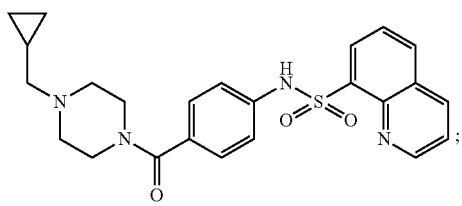

with $H_2SO_4$ in an alcoholic solution. In one aspect, the molar ratio of the compound of Formula 1 to $H_2SO_4$ is about 2:1. In another aspect, the alcoholic solution further comprises water. In one aspect, the method of forming crystalline Form A described above further comprises the step of, after the reaction with $H_2SO_4$, adding a sufficient amount of water to precipitate the crystalline form. In one aspect, the alcohol is methanol or ethanol. In another aspect, the solution further comprises an aromatic solvent. In another aspect, the aromatic solvent is toluene.

In one alternative, crystalline Form A is prepared by reacting Compound 1 with $H_2SO_4$ in a solution comprising acetone and water. In one aspect, the solution is acetone: water (9:1/v:v).

Also provided is a method of forming a hemisulfate salt of a compound having the formula:

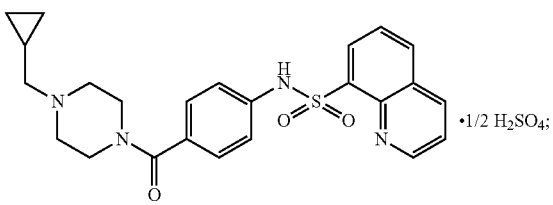 [SMILES: O=C(c1ccc(NS(=O)(=O)c2cccc3cccnc23)cc1)N1CCN(CC2CC2)CC1]

the method comprising reacting the non-crystalline freebase of compound 1 with a solution of sulfuric acid in EtOAc. In one aspect, the concentration of sulfuric acid in EtOAc is about 15 wt % to about 30 wt %. In certain embodiments, the concentration of sulfuric acid in EtOAc is about 24 wt %.

In one alternative, the hemisulfate salt is prepared by reacting Compound 1 with $H_2SO_4$ in a solution comprising water and an alcohol such as MeOH or EtOH.

Also provided is a method of forming an amorphous form of a hemisulfate salt of a compound of the formula:

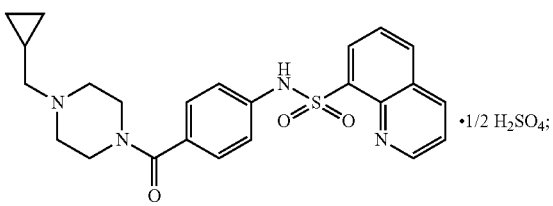 [SMILES: O=C(c1ccc(NS(=O)(=O)c2cccc3cccnc23)cc1)N1CCN(CC2CC2)CC1]

the method comprising crystallizing Form A of a hemisulfate salt of a compound having the formula:

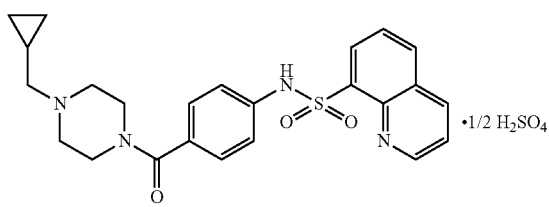 [SMILES: O=C(c1ccc(NS(=O)(=O)c2cccc3cccnc23)cc1)N1CCN(CC2CC2)CC1]

via evaporation from MeOH. Alternatively, the amorphous form of the hemisulfate salt can be prepared by crystallizing the crystalline Form A of a hemisulfate salt from THF. In one aspect, the evaporative crystallization is performed in methanol or THF at about 50° C.

Compositions and Administration

Provided herein are pharmaceutical compositions comprising one or more of the disclosed crystalline forms (e.g. crystalline Form A), or the disclosed amorphous form, together with a pharmaceutically acceptable carrier. The amount of crystalline or amorphous form in a provided composition is such that is effective to measurably modulate PKR in a subject.

Pharmaceutical compositions described herein can be prepared by any method known in the art of pharmacology. In general, such preparatory methods include the steps of bringing one or more of the disclosed crystalline forms (e.g. crystalline Form A) into association with a carrier and/or one or more other accessory ingredients, and then, if necessary and/or desirable, shaping and/or packaging the product into a desired single- or multi-dose unit.

Pharmaceutically acceptable carriers used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Carriers such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite (aluminum silicate) and Veegum (magnesium aluminum silicate)), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g. polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g. Cremophor™), polyoxyethylene ethers, (e.g. polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer-188, cetrimonium bromide, cetylpyridinium chloride, benzalkonium chloride, docusate sodium, and/or mixtures thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, sodium stearyl fumarate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Compositions described herein may be administered orally, parenterally, by inhalation spray, topically, rectally, nasally, buccally, transmucosally, or in an ophthalmic preparation. The term "parenteral" as used herein includes subcutaneous, intravenous, intramuscular, intra-articular, intrasynovial, intrasternal, intrathecal, intrahepatic, intralesional and intracranial injection or infusion techniques. In one aspect, the pharmaceutical compositions provided herewith are orally administered in an orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The amount of provided crystalline or amorphous form that may be combined with carrier materials to produce a composition in a single dosage form will vary depending upon the subject to be treated and the particular mode of administration. For example, a specific dosage and treatment regimen for any particular subject will depend upon a variety of factors, including age, body weight, general health, sex, diet, time of administration, rate of excretion, drug combination, the judgment of the treating physician, and the severity of the particular disease being treated. The amount of a provided crystalline form in the composition will also depend upon the particular form (e.g., Form A, B, C, D, E, F, G, H, I, or J) in the composition. In one aspect, a provided composition may be formulated such that a dosage equivalent to about 0.001 to about 100 mg/kg body weight/day of compound 1 (e.g., about 0.5 to about 100 mg/kg of compound 1) can be administered to a subject receiving these compositions. Alternatively, dosages equivalent to 1 mg/kg and 1000 mg/kg of compound 1 every 4 to 120 hours is also acceptable. As used herein, the dose refers to the amount of compound 1 in the particular crystalline form. The amount of the particular crystalline form will be calculated based on the equivalence to the free-base form of compound 1.

In one aspect, a disclosed crystalline (e.g. crystalline Form A) or amorphous form is formulated for administration at a dose of equivalent to about 2 mg to about 3000 mg of compound 1. In certain embodiments, the dose is oral dose. In certain embodiments, a disclosed crystalline (e.g. crystalline Form A) or amorphous form is formulated equivalent to about 2 mg to about 3000 mg of compound 1. In certain embodiments, a disclosed crystalline (e.g. crystalline Form A) or amorphous form is formulated equivalent to about 5 mg to about 350 mg of compound 1. In certain embodiments, a disclosed crystalline (e.g. crystalline Form A) or amorphous form is formulated equivalent to about 5 mg to about 200 mg of compound 1. In certain embodiments, a disclosed crystalline (e.g. crystalline Form A) or amorphous form is formulated equivalent to about 5 mg to about 100 mg of compound 1. In certain embodiments, a disclosed crystalline (e.g. crystalline Form A) or amorphous form is formulated equivalent to about 5 mg of compound 1. In certain embodiments, a disclosed crystalline (e.g. crystalline Form A) or amorphous form is formulated equivalent to about 10 mg of compound 1. In certain embodiments, a disclosed crystalline (e.g. crystalline Form A) or amorphous form is formulated equivalent to about 15 mg of compound 1. In certain embodiments, a disclosed crystalline (e.g. crystalline Form A) or amorphous form is formulated equivalent to about 20 mg of compound 1. In certain 25 mg. In certain embodiments, a disclosed crystalline (e.g. crystalline Form A) or amorphous form is formulated equivalent to about 30 mg of compound 1. In certain embodiments, a disclosed crystalline (e.g. crystalline Form A) or amorphous form is formulated equivalent to about 40 mg of compound 1. In certain embodiments, a disclosed crystalline (e.g. crystalline Form A) or amorphous form is formulated equivalent to about 45 mg of compound 1. In certain embodiments, a disclosed crystalline (e.g. crystalline Form A) or amorphous form is formulated equivalent to about 50 mg of compound 1. In certain embodiments, a disclosed crystalline (e.g. crystalline Form A) or amorphous form is formulated equivalent to about 60 mg of compound 1. In certain embodiments, a disclosed crystalline (e.g. crystalline Form A) or amorphous form is formulated equivalent to about 70 mg of compound 1. In certain embodiments, a disclosed crystalline (e.g. crystalline Form A) or amorphous form is formulated equivalent to about 80 mg of compound 1. In certain embodiments, a disclosed crystalline (e.g. crystalline Form A) or amorphous form is formulated equivalent to about 90 mg of compound 1. In certain embodiments, a disclosed crystalline (e.g. crystalline Form A) or amorphous form is formulated equivalent to about 100 mg of compound 1. In certain embodiments, a disclosed crystalline (e.g. crystalline Form A) or amorphous form is formulated equivalent to about 110 mg of compound 1. In certain embodiments, a disclosed crystalline (e.g. crystalline Form A) or amorphous form is formulated equivalent to about 120 mg of compound 1.

In certain embodiments, a disclosed crystalline (e.g. crystalline Form A) or amorphous form is formulated for administration at a dose equivalent to about 2 mg to about 3000 mg of compound 1 per day. In certain embodiments, a disclosed crystalline (e.g. crystalline Form A) or amorphous form is formulated for administration at a dose equivalent to about 5 mg to about 500 mg of compound 1 per day. In certain embodiments, a disclosed crystalline (e.g. crystalline Form A) or amorphous form is formulated for administration at a dose equivalent to about 5 mg to about 200 mg of compound 1 per day. In certain embodiments, a disclosed crystalline (e.g. crystalline Form A) or amorphous form is formulated for administration at a dose equivalent to about 5 mg of compound 1 per day. In certain embodiments, a disclosed crystalline (e.g. crystalline Form A) or amorphous form is formulated for administration at a dose equivalent to about 5 mg to about 10 mg of compound 1 per day. In certain embodiments, a disclosed crystalline (e.g. crystalline Form A) or amorphous form is formulated for administration at a dose of about 15 mg equivalent to compound 1 per day. In certain embodiments, a disclosed crystalline (e.g. crystalline Form A) or amorphous form is formulated for administration at a dose equivalent to about 20 mg of compound 1 per day. In certain embodiments, a disclosed crystalline (e.g. crystalline Form A) or amorphous form is formulated for administration at a dose equivalent to about 25 mg of compound 1 per day. In certain embodiments, a disclosed crystalline (e.g. crystalline Form A) or amorphous form is formulated for administration at a dose equivalent to about 30 mg of compound 1 per day. In certain embodiments, a disclosed crystalline (e.g. crystalline Form A) or amorphous form is formulated for administration at a dose equivalent to about 35 mg of compound 1 per day. In certain embodiments, a disclosed crystalline (e.g. crystalline Form A) or amorphous form is formulated for administration at a dose equivalent to about 40 mg of compound 1 per day. In certain embodiments, a disclosed crystalline (e.g. crystalline Form A) or amorphous form is formulated for administration at a dose equivalent to about 45 mg of compound 1 per day. In certain embodiments, a disclosed crystalline (e.g. crystalline Form A) or amorphous form is formulated for administration at a dose equivalent to about 50 mg of compound 1 per day. In certain embodiments, a disclosed crystalline (e.g. crystalline Form A) or amorphous form is formulated for administration at a dose equivalent to about 60 mg of compound 1 per day. In certain embodiments, a disclosed crystalline (e.g. crystalline Form A) or amorphous form is formulated for administration at a dose equivalent to about 70 mg of compound 1 per day. In certain embodiments, a disclosed crystalline (e.g. crystalline Form A) or amorphous form is formulated for administration at a dose equivalent to about 80 mg of compound 1 per day. In certain embodiments, a disclosed crystalline (e.g. crystalline Form A) or amorphous form is formulated for administration at a dose equivalent to about 90 mg of compound 1 per day. In certain embodiments, a disclosed crystalline (e.g. crystalline Form A) or amorphous form is formulated for administration at a dose equivalent to about 100 mg of compound 1 per day. In certain embodiments, a disclosed crystalline (e.g. crystalline Form A) or amorphous form is formulated for administration at a dose equivalent to about 110 mg of compound 1 per day. In certain embodiments, a disclosed crystalline (e.g. crystalline Form A) or amorphous form is formulated for administration at a dose equivalent to about 120 mg of compound 1 per day. In certain embodiments, a disclosed crystalline (e.g. crystalline Form A) or amorphous form is formulated for administration at a dose equivalent to about 130 mg of compound 1 per day. In certain embodiments, a disclosed crystalline (e.g. crystalline Form A) or amorphous form is formulated for administration at a dose equivalent to about 140 mg of compound 1 per day. In certain embodiments, a disclosed crystalline (e.g. crystalline Form A) or amorphous form is formulated for administration at a dose equivalent to about 150 mg of compound 1 per day. Dosing can be once, twice, or three times daily. In one aspect, e.g., a disclosed crystalline (e.g. crystalline Form A) or amorphous form is formulated for administration at a dose equivalent to about 5 mg of compound 1 twice per day. In one aspect, e.g., a disclosed crystalline (e.g. crystalline Form A) or amorphous form is formulated for administration at a dose equivalent to about 20 mg of compound 1 twice per day. In one aspect, e.g., a disclosed crystalline (e.g. crystalline Form A) or amorphous form is formulated for administration at a dose equivalent to about 50 mg of compound 1 twice per day. In one aspect, e.g., a disclosed crystalline (e.g. crystalline Form A) or amorphous form is formulated for administration at a dose equivalent to about 100 mg of compound 1 twice per day. In one aspect, e.g., a disclosed crystalline (e.g. crystalline Form A) or amorphous form is formulated for administration at a dose equivalent to about 5 mg of compound 1 once every other day. In one aspect, e.g., a disclosed crystalline (e.g. crystalline Form A) or amorphous form is formulated for administration at a dose equivalent to about 20 mg of compound 1 once every other day. In one aspect, e.g., a disclosed crystalline (e.g. crystalline Form A) or amorphous form is formulated for administration at a dose equivalent to about 50 mg of compound 1 once every other day. In one aspect, e.g., a disclosed crystalline (e.g. crystalline Form A) or amorphous form is formulated for administration at a dose equivalent to about 100 mg of compound 1 once every other day.

In one aspect, a disclosed form (crystalline Form A, B, C, D, E, F, G, H, I, J, the crystalline free-base, or the amorphous form) is formulated as a tablet composition together with a pharmaceutically acceptable carrier. In one aspect, the carrier is selected from one or more of microcrystalline cellulose, mannitol, Croscarmellose Sodium, and Sodium Stearyl Fumarate. In one aspect, the carrier is microcrystalline cellulose e.g., present in an amount of 50% w/w to 70% w/w (±2%), 55% w/w to 65% w/w (±2%), 58% w/w to 62% w/w (±2%), 59% w/w (±2%), 60% w/w (±2%), 61% w/w (±2%), 62% w/w (±2%), 61% w/w, or 62% w/w. In another aspect, the carrier is mannitol e.g., present in an amount of 15% w/w (±2%) to 35% w/w (±2%), 20% w/w (±2%) to 30% w/w (±2%), 22% w/w (±2%) to 26% w/w (±2%), 22% w/w (±2%), 23% w/w (±2%), 24% w/w (±2%), or 23% w/w. In another aspect, the carrier is croscarmellose sodium e.g., present in an amount of 1% w/w to 5% w/w (±2%), 2% w/w to 4% w/w (±2%), 2% w/w (±2%), 3% w/w (±2%), 4% w/w (±2%) or 3% w/w. In another aspect, the carrier is stearyl fumarate e.g., present in an amount of 1% w/w to 5% w/w (±2%), 2% w/w to 4% w/w (±2%), 1% w/w (±2%), 2% w/w (±2%), 3% w/w (±2%) or 2% w/w. In some embodiments, crystalline form A is present in the tablet composition in an amount equivalent to about 1 to about 200 mg of compound 1. In some embodiments, crystalline form A is present in the tablet composition in an amount equivalent to about 1 to about 150 mg of compound 1. In some embodiments, crystalline form A is present in the tablet composition in an amount equivalent to about 1 to about 100 mg of compound 1. In some embodiments, crystalline form A is present in the tablet composition in an amount equivalent to about 5 mg of compound 1. In some embodiments, crystalline form A is present in the tablet composition in an amount equivalent to about 20 mg of compound 1. In some embodiments, crystalline form A is present in the tablet composition in an amount equivalent to about 50 mg of compound 1. In some embodiments, crystalline form A is present in the tablet composition in an amount equivalent to about 75 mg of compound 1. In some embodiments, crystalline form A is present in a tablet composition in an amount equivalent to about 100 mg of compound 1.

As used herein, the dose amount of crystalline Form A, B, C, D, E, F, G, H, I, J, or the amorphous form is based on the equivalence to the free-base form of compound 1. For example, "crystalline form A present in the composition in an amount equivalent to about 1.0 mg of compound 1" means about 1.18 mg of crystalline Form A is present in the composition and is equivalent to about 1.0 mg of free base compound 1.

In one aspect, the tablet composition comprises 10% w/w ((±1%) of the crystalline free-base; 62% w/w (±2%) microcrystalline cellulose; 23% w/w (±2%) mannitol, 3% w/w (±2%) croscarmellose sodium, and 2% w/w (±2%) stearyl fumarate.

In one aspect, the tablet composition comprises 11.78% w/w (±1%) of crystalline Form A; 62% w/w (±2%) microcrystalline cellulose; 23% w/w (±2%) mannitol; 3% w/w (±2%) croscarmellose sodium; and 2% w/w (±2%) stearyl fumarate.

In certain embodiments, provided is a pharmaceutical composition comprising crystalline Form A and a pharmaceutically acceptable carrier. In certain embodiments, provided is a pharmaceutical composition comprising the crystalline Form A is substantially free of Compound IM-1 and/or Compound IM-2 (see Exemplification). In certain embodiments, the pharmaceutical composition comprising Form A is substantially free of other crystal forms of the hemisulfate salt of compound 1. In certain embodiments, the one or more carriers are processed to generate particles of a consistent size. In certain embodiments, processing the powder (i.e., crystalline Form A) comprises milling the powder for an amount of time suitable to bring about a desired particle size ("milled powder"). In some embodiments, the particle size of the milled powder is less than about 400 µm. In some embodiments, the particle size of the milled powder is less than about 300 µm. In some embodiments, the particle size of the milled powder is less than about 200 µm. In some embodiments, the particle size of the milled powder is less than about 100 µm. In some embodiments, the particle size of the milled powder is less than about 90 µm. In some embodiments, the particle size of the milled powder is less than about 80 µm. In some embodiments, the particle size of the milled powder is less than about 70 µm. In some embodiments, the particle size of the milled powder is less than about 60 µm. In some embodiments, the particle size of the milled powder is less than about 50 µm. In some embodiments, the particle size of the milled powder is less than about 40 µm. In some embodiments, the particle size of the milled powder is less than about 30 µm. In some embodiments, the particle size of the milled powder is less than about 20 µm. In some embodiments, the particle size of the milled powder ranges from about 10 µm to about 400 µm. In some embodiments, the particle size of the milled powder ranges from about 10 µm to about 300 µm. In some embodiments, the particle size of the milled powder ranges from about 10 µm to about 200 µm. In some embodiments, the particle size of the milled powder ranges from about 10 µm to about 100 µm. In some embodiments, the particle size of the milled powder ranges from about 10 µm to about 80 µm. In some embodiments, the particle size of the milled powder ranges from about 10 µm to about 70 µm. In some embodiments, the particle size of the milled powder ranges from about 10 µm to about 60 µm. In some embodiments, the particle size of the milled powder ranges from about 20 µm to about 60 µm. The term "about," as used herein with respect to particle size, means+/−5 µm.

In some embodiments, at least 90% of a representative sample of the milled powder has a particle size of less than about 100, about 80, about 70, about 60, about 50, about 40, about 30, about 20, or about 10 µm. In some embodiments, at least about 90% of a representative sample of the milled powder has a particle size of less than about 60 µm.

Methods of Treatment and Uses of Compounds and Compositions

In one aspect, the crystalline and amorphous forms described herein and compositions thereof are allosteric activators of PKR, and are generally useful for treating the underlying condition of PKD.

Thus, provided herein are methods of treating Pyruvate Kinase Deficiency (PKD) in a subject in need thereof, comprising administering to the subject an effective amount of crystalline Form A, B, C, D, E, F, G, H, I, or J or the amorphous Form of the compound of formula (I), or a pharmaceutical composition thereof. Also provided is crystalline Form A, B, C, D, E, F, G, H, I, or J or the amorphous Form of the compound of formula (I); or a pharmaceutical composition thereof for use in treating Pyruvate Kinase Deficiency (PKD) in a subject in need thereof. Further provided is the use of crystalline Form A, B, C, D, E, F, G, H, I, or J, or the amorphous Form of the compound of formula (I), or a pharmaceutical composition thereof in the manufacture of a medicament for treating Pyruvate Kinase Deficiency (PKD). Exemplified conditions related to PKD include, but are not limited to, anemias, cholecystolithiasis, gallstones, tachycardia, hemochromatosis, icteric sclera, splenomegaly, leg ulcers, jaundice, fatigue, and shortness of breath. As described herein, PKD is a deficiency of PKR. In certain embodiments, the deficiency of PKR is associated with a PKR mutation.

Pyruvate kinase deficiency (PKD) is a glycolytic enzymopathy that results in life-long hemolytic anemia. In certain embodiments, the subject having PKD is a patient having at least 2 mutant alleles in PKLR gene. In certain embodiments, the subject having PKD is a patient having at least 2 mutant alleles in PKLR gene and at least one is a missense mutation. See Canu. et. al, Blood Cells, Molecules and Diseases 2016, 57, pp. 100-109. In certain embodiments, a subject having PKD has an Hb concentration less than or equal to 10.0 g/dL. In certain embodiments, the subject having PKD is an adult not under regular transfusion (e.g. having had no more than 4 transfusion episodes in the 12-month period up to the treatment). In certain embodiments, the subject having PKD is an adult transfusion independent (e.g. having no more than 3 units of RBCs transfused in the 12-month period prior to the treatment). In certain embodiments, the subject having PKD is an adult under regular transfusion (e.g. having had at least 4 transfusion episodes (e.g., at least 6 transfusion episodes) in the 12-month period prior to the treatment). In certain embodiments, the subject having PKD has a total number of at least 5 transfusion episodes during the subject's lifetime. In certain embodiments, the subject having PKD has a total number of at least 10 transfusion episodes during the subject's lifetime. In certain embodiments, the subject having PKD has a total number of at least 15 transfusion episodes during the subject's lifetime. In certain embodiments, the subject having PKD has a total number of at least 20 transfusion episodes during the subject's lifetime. In certain embodiments, the subject having PKD has a total number of at least 25 transfusion episodes during the subject's lifetime. In certain embodiments, the subject having PKD has a total number of at least 30 transfusion episodes during the subject's lifetime. In certain embodiments, the subject having PKD has a total number of at least 40 transfusion episodes during the subject's lifetime. In certain embodiments, the subject having PKD has a total number of at least 50 transfusion episodes during the subject's lifetime. In certain embodiments, the subject having PKD has a total number of at least 60 transfusion episodes during the subject's lifetime. In certain embodiments, the subject having PKD has a total number of at least 70 transfusion episodes during the subject's lifetime. In certain embodiments, the subject having PKD is not homozygous for the R479H mutation or does not have 2 non-missense mutations in the PKLR gene. In certain embodiments, the subject having PKD, under regular transfusion, has hemoglobin (Hb)≤12.0 g/dL (if male) or ≤11.0 g/dL (if female), prior to the treatment. In certain embodiments, the subject having PKD, under regular transfusion, has transfusion occurring on average less than or equal to once every three weeks. In certain embodiments, the subject having PKD has received at least 0.8 mg (e.g. at least 1.0 mg) folic acid daily (e.g. for at least 21 days) prior to the treatment. In certain embodiments, the subject with PKD under regular transfusion achieves a reduction in transfusion burden (e.g. at least 33% reduction in the number of RBC units transfused) during the 5 weeks, 10 weeks, 15 weeks, 20 weeks, or 24 weeks, 28 weeks, or 32 weeks of treatment. In certain embodiments, the subject having PKD, not under regular transfusion (having had no more than 4 transfusion episodes in the 12-month period prior to the treatment and/or no transfusion in the 3 months prior to the treatment), has hemoglobin (Hb)≤10.0 g/dL regardless of gender prior to the treatment. In certain embodiments, the subject having PKD has undergone splenectomy.

In certain embodiments, the subject with PKD achieves a hemoglobin response of at least 1.0 g/dL increase in Hb concentration after the treatment compared to the baseline of prior to the treatment. In certain embodiments, the subject with PKD achieves a hemoglobin response of at least 1.5 g/dL increase in Hb concentration from baseline prior to the treatment. In certain embodiments, the subject with PKD achieves a hemoglobin response of at least 2.0 g/dL increase in Hb concentration from baseline prior to the treatment.

In an embodiment, the mutant PKR is selected from the group consisting of A31V, A36G, G37Q, R40W, R40Q, L73P, S80P, P82H, R86P, I90N, T93I, G95R, M107T, G111R, A115P, S120F, H121Q, S130P, S130Y, V134D, R135D, A137T, G143S, I153T, A154T, L155P, G159V, R163C, R163L, T164N, G165V, L167M, G169G, E172Q, W201R, I219T, A221Y, D221N, G222A, I224T, G232C, N253D, G263R, G263W, E266K, V269F, L272V, L272P, G275R, G275R, E277K, V280G, D281N, F287V, F287L, V288L, D293N, D293V, A295I, A295V, I310N, I314T, E315K, N316K, V320L, V320M, S330R, D331N, D331G, D331E, G332S, V335M, A336S, R337W, R337P, R337Q, D339N, D339Q, G341A, G341D, I342F, K348N, A352D, I357T, G358R, G358E, R359C, R359H, C360Y, N361D, G364D, K365M, V368F, T371I, L374P, S376I, T384M, R385W, R385K, E387G, D390N, A392T, N393D, N393S, N393K, A394S, A394D, A394V, V395L, D397V, G398A, M403I, G406R, E407K, E407G, T408P, T408A, T408I, K410E, G411S, G411A, Q421K, A423A, A423A, R426W, R426Q, E427A, E427N, A431T, R449C, I457V, G458D, A459V, V460M, A468V, A468G, A470D, T477A, R479C, R479H, S485F, R486W, R486L, R488Q, R490W, I494T, A495T, A495V, R498C, R498H, A503V, R504L, Q505E, V506I, R510Q, G511R, G511E, R518S, R531C, R532W, R532Q, E538D, G540R, D550V, V552M, G557A, R559G, R559P, N566K, M568V, R569Q, R569L, Q58X, E174X, W201X, E241X, R270X, E440X, R486X, Q501X, L508X, R510X, E538X, R559X. These mutations are described in Canu et. al., Blood Cells, Molecules and Diseases 2016, 57, pp. 100-109. In an embodiment, the mutant PKR is selected from G332S, G364D, T384M, K410E, R479H, R479K, R486W, R532W, R510Q, and R490W. In certain embodiments, the mutant PKR is selected from A468V, A495V, I90N, T408I, and Q421K, and R498H. In certain embodiments, the mutant PKR is R532W, K410E, or R510Q. In certain embodiments, the mutant PKR is R510Q, R486W, or R479H.

In other aspects, provided are methods of treating a disease selected from hemolytic anemia, sickle cell disease, thalassemia, hereditary spherocytosis, hereditary elliptocytosis, abetalipoproteinemia, Bassen-Kornzweig syndrome, and paroxysmal nocturnal hemoglobinuria in a subject in need thereof, comprising administering to the subject an effective amount of crystalline Form A, B, C, D, E, F, G, H, I, or J or the amorphous Form of the compound of formula (I), or a pharmaceutical composition thereof. Also provided is crystalline Form A, B, C, D, E, F, G, H, I, or J or the amorphous Form of the compound of formula (I), or a pharmaceutical composition thereof for use in treating disease selected from hemolytic anemia, sickle cell disease, thalassemia, hereditary spherocytosis, hereditary elliptocytosis, abetalipoproteinemia, Bassen-Kornzweig syndrome, and paroxysmal nocturnal hemoglobinuria in a subject. Further provided is the use of crystalline Form A, B, C, D, E, F, G, H, I, or J or the amorphous Form of the compound of formula (I), or a pharmaceutical composition thereof in the manufacture of a medicament for treating a disease selected from hemolytic anemia, sickle cell disease, thalassemia, hereditary spherocytosis, hereditary elliptocytosis, abetalipoproteinemia, Bassen-Kornzweig syndrome, and paroxysmal nocturnal hemoglobinuria in a subject in need thereof. In one aspect, the disease to be treated is hemolytic anemia.

In other aspects, provided herein are methods for treating thalassemia (e.g., beta-thalassemia or non-transfusion-dependent thalassemia) in a subject in need thereof, comprising administering to the subject an effective amount of crystalline Form A, B, C, D, E, F, G, H, I, or J or the amorphous Form of the compound of formula (I), or a pharmaceutical composition thereof. Also provided is crystalline Form A, B, C, D, E, F, G, H, I, or J or the amorphous Form of the compound of formula (I), or a pharmaceutical composition thereof for use in treating thalassemia (e.g., beta-thalassemia or non-transfusion-dependent thalassemia). Further provided is the use of crystalline Form A, B, C, D, E, F, G, H, I, or J or the amorphous Form of the compound of formula (I), or a pharmaceutical composition thereof in the manufacture of a medicament for treating thalassemia (e.g., beta-thalassemia or non-transfusion-dependent thalassemia).

In other aspects, provided herein are methods for treating thalassemia (e.g., beta-thalassemia or non-transfusion-dependent thalassemia) in a subject in need thereof, comprising administering to the subject an effective amount of crystalline Form A, or a pharmaceutical composition thereof. Also provided is crystalline Form A or a pharmaceutical composition thereof for use in treating thalassemia (e.g., beta-thalassemia or non-transfusion-dependent thalassemia). Further provided is the use of crystalline Form A, or a pharmaceutical composition thereof, in the manufacture of a medicament for treating thalassemia (e.g., beta-thalassemia or non-transfusion-dependent thalassemia).

In other aspects, provided herein are methods for treating thalassemia (e.g., beta-thalassemia or non-transfusion-dependent thalassemia) in a subject in need thereof, comprising administering to the subject an effective amount of crystalline Form D, or a pharmaceutical composition thereof. Also provided is crystalline Form D, or a pharmaceutical composition thereof for use in treating thalassemia (e.g., beta-thalassemia or non-transfusion-dependent thalassemia). Further provided is the use of crystalline Form D, or a pharmaceutical composition thereof, in the manufacture of a medicament for treating thalassemia (e.g., beta-thalassemia or non-transfusion-dependent thalassemia).

In certain embodiments, the subject is an adult subject with thalassemia. In certain embodiments, the subject has thalassemia such as β-thalassemia *intermedia*, Hb E β-thalassemia, α-thalassemia (Hb H disease), or β-thalassemia with mutations of 1 or more α genes. In certain embodiments, the subject has beta-thalassemia or non-transfusion-dependent thalassemia. In certain embodiments, the subject is an adult male subject with thalassemia such as beta-thalassemia or non-transfusion-dependent thalassemia. In certain embodiments, the subject is a female subject with thalassemia such as beta-thalassemia or non-transfusion-dependent thalassemia. In certain embodiments, the subject is an adult female subject with thalassemia such as beta-thalassemia or non-transfusion-dependent thalassemia. In certain embodiments, the subject has a hemoglobin concentration of less than or equal to 6.0 g/dL. In certain embodiments, the subject has a hemoglobin concentration of less than or equal to 7.0 g/dL. In certain embodiments, the subject has a hemoglobin concentration of less than or equal to 8.0 g/dL. In certain embodiments, the subject has a hemoglobin concentration of less than or equal to 9.0 g/dL. In certain aspects, the subject having non-transfusion-dependent thalassemia does not have a known history (e.g., has been diagnosed in the past) of Hb S or Hb C forms of thalassemia. In certain embodiments, the term "non-transfusion dependent" thalassemia refers to subjects with thalassemia having no more than 4 (e.g. five) units of RBCs transfused during a 24-week period up to the first day of administration of a crystalline or amorphous form described herein and/or no RBC transfusions in the 8 weeks prior to the first day of administration of a crystalline or amorphous form described herein.

In other aspects, provided herein are methods for increasing the lifetime of red blood cells (RBCs) in a subject in need thereof comprising administering to the subject an effective amount of crystalline Form A, B, C, D, E, F, G, H, I, or J or the amorphous Form of the compound of formula (I), or a pharmaceutical composition thereof. Also provided is crystalline Form A, B, C, D, E, F, G, H, I, or J or the amorphous Form of the compound of formula (I), or a pharmaceutical composition thereof for use in increasing the lifetime of red blood cells (RBCs) in a subject in need thereof. Further provided is the use of crystalline Form A, B, C, D, E, F, G, H, I, or J or the amorphous Form of the compound of formula (I), or a pharmaceutical composition thereof in the manufacture of a medicament for increasing the lifetime of red blood cells (RBCs). In one aspect, crystalline Form A, B, C, D, E, F, G, H, I, or J or the amorphous Form of the compound of formula (I), or a pharmaceutical composition thereof is added directly to whole blood or packed red blood cells extracorporeally.

In other aspects, provided herein are methods for regulating 2,3-diphosphoglycerate levels in blood in a subject in need thereof comprising contacting blood with an effective amount of crystalline Form A, B, C, D, E, F, G, H, I, or J or the amorphous Form of the compound of formula (I), or a pharmaceutical composition thereof. Also provided is crystalline Form A, B, C, D, E, F, G, H, I, or J or the amorphous Form of the compound of formula (I), or a pharmaceutical composition thereof for use in regulating 2,3-diphosphoglycerate levels in blood in a subject in need thereof. Further provided is the use of crystalline Form A, B, C, D, E, F, G, H, I, or J or the amorphous Form of the compound of formula (I), or a pharmaceutical composition thereof in the manufacture of a medicament for regulating 2,3-diphosphoglycerate levels in blood.

In other aspects, provided herein are methods for treating anemia in a subject in need thereof comprising administering to the subject an effective amount of crystalline Form A, B, C, D, E, F, G, H, I, or J or the amorphous Form of the compound of formula (I), or a pharmaceutical composition thereof. Also provided is crystalline Form A, B, C, D, E, F, G, H, I, or J or the amorphous Form of the compound of formula (I), or a pharmaceutical composition thereof for use in treating anemia in a subject in need thereof. Further provided is the use of crystalline Form A, B, C, D, E, F, G, H, I, or J or the amorphous Form of the compound of formula (I), or a pharmaceutical composition thereof in the manufacture of a medicament for treating anemia. In one aspect, the anemia to be treated is dyserythropoietic anemia.

In certain embodiments, the anemia is a dyserythropoietic anemia such as congenital dyserythropoietic anemia type I, II, III, or IV. In certain embodiments, the anemia is hemolytic anemia. In certain embodiments, the hemolytic anemia is a congenital and/or hereditary form of hemolytic anemia such as PKD, sickle cell disease, thalassemias (e.g. alpha or beta or non-transfusion-dependent thalassemia), hereditary spherocytosis, hereditary elliptocytosis), paroxysmal nocturnal hemoglobinuria, abeta-liproteinemia (Bassen-Kornzweig syndrome). In certain embodiments, the hemolytic anemia is acquired hemolytic anemia such as autoimmune hemolytic anemia, drug-induced hemolytic anemia. In certain embodiments, the hemolytic anemia is anemia as part of a multi-system disease, such as the anemia of Congenital Erythropoietic Purpura, Fanconi, Diamond-Blackfan.

As used herein, the term "anemia" refers to a deficiency of red blood cells (RBCs) and/or hemoglobin. As used herein, anemia includes all types of clinical anemia, for example (but not limited to): microcytic anemia, iron deficiency anemia, hemoglobinopathies, heme synthesis defect, globin synthesis defect, sideroblastic defect, normocytic anemia, anemia of chronic disease, aplastic anemia, hemolytic anemia, macrocytic anemia, megaloblastic anemia, pernicious anemia, dimorphic anemia, anemia of prematurity, Fanconi anemia, hereditary spherocytosis, sickle cell disease, warm autoimmune hemolytic anemia, cold agglutinin hemolytic anemia, osteopetrosis, thalassemia, and myelodysplastic syndrome.

In certain embodiments, anemia can be diagnosed on a complete blood count. In certain embodiments, anemia can be diagnosed based on the measurement of one or more markers of hemolysis (e.g. RBC count, hemoglobin, reticulocytes, schistocytes, lactate Dehydrogenase (LDH), haptoglobin, bilirubin, and ferritin) and/or hemosiderinuria mean corpuscular volume (MCV) and/or red cell distribution width (RDW). In the context of the present invention, anemia is present if an individual has a hemoglobin (Hb) less than the desired level, for example, the Hb concentration of less than 14 g/dL, more preferably of less than 13 g/dL, more preferably of less than 12 g/dL, more preferably of less than 11 g/dL, or most preferably of less than 10 g/dL.

In certain embodiments, provided herein is a method of increasing the amount of hemoglobin in a subject by administering an effective amount of crystalline Form A, B, C, D, E, F, G, H, I, or J or the amorphous Form of the compound of formula (I), or a pharmaceutical composition thereof as described herein. In certain embodiments, also provided herein is a method of increasing the amount of hemoglobin in a subject having thalassemia comprising administering to the subject an effective amount of crystalline Form A, B, C, D, E, F, G, H, I, or J, or the crystalline free base, or the amorphous Form of the compound of formula (I), or a pharmaceutical composition thereof. Further provided is a method of increasing the amount of hemoglobin in subjects having non-transfusion-dependent thalassemia comprising administering an effective amount of crystalline Form A, B, C, D, E, F, G, H, I, or J, or the crystalline free base, or the amorphous Form of the compound of formula (I), or a pharmaceutical composition thereof as described herein to the subject. In certain embodiments, the provided methods increase hemoglobin concentration in the subject. In certain embodiments, the provided methods increase Hb concentration to a desired level, for example, above 10 g/dL, more preferably above 11 g/dL, more preferably above 12 g/dL, more preferably above 13 g/dL, or most preferably above 14 g/dL. In certain embodiments, the provided methods increase Hb concentration by at least about 0.5 g/dL. In certain embodiments, the provided methods increase Hb concentration by at least about 1.0 g/dL. In certain embodiments, the provided methods increase Hb concentration by at least about 1.5 g/dL. In certain embodiments, the provided methods increase Hb concentration by at least about 2.0 g/dL. In certain embodiments, the provided methods increase Hb concentration by at least about 2.5 g/dL. In certain embodiments, the provided methods increase Hb concentration by at least about 3.0 g/dL. In certain embodiments, the provided methods increase Hb concentration by at least about 3.5 g/dL. In certain embodiments, the provided methods increase Hb concentration by at least about 4.0 g/dL. In certain embodiments, the provided methods increase Hb concentration by at least about 4.5 g/dL. In certain embodiments, the provided methods increase Hb concentration by at least about 5.0 g/dL. In certain embodiments, the provided methods increase Hb concentration by at least about 5.5 g/dL. In certain embodiments, the provided methods increase Hb concentration by at least about 6.0 g/dL. In certain embodiments, the increase in Hb concentration is determined from baseline at one or more assessment between week 1 and week 20 (e.g., between week 2 and week 15, between week 3 and week 15, and between week 4 and week 12) of treatment with an effective amount of crystalline Form A, B, C, D, E, F, G, H, I, or J, or the crystalline free base or amorphous Form of the compound of formula (I), or a pharmaceutical composition thereof as described herein. In certain embodiments, the provided methods increase Hb concentration as described above in female subjects having thalassemia (e.g., beta-thalassemia or non-transfusion-dependent thalassemia). In certain embodiments, the provided methods increase Hb concentration from baseline to about 12 g/dL in female subjects having thalassemia (e.g., beta-thalassemia or non-transfusion-dependent thalassemia). In certain embodiments, the provided methods increase Hb concentration as described above in male subjects having thalassemia (e.g., beta-thalassemia or non-transfusion-dependent thalassemia). In certain embodiments, the provided methods increase Hb concentration from baseline to about 13 g/dL in male subjects having thalassemia (e.g., beta-thalassemia or non-transfusion-dependent thalassemia).

In some aspects, provided herein are methods for treating hemolytic anemia in a subject in need thereof comprising administering to the subject an effective amount of crystalline Form A, B, C, D, E, F, G, H, I, or J or the amorphous Form of the compound of formula (I), or a pharmaceutical composition thereof. Also provided is crystalline Form A, B, C, D, E, F, G, H, I, or J or the amorphous Form of the compound of formula (I), or a pharmaceutical composition thereof for use in treating hemolytic anemia in a subject in need thereof. Further provided is the use of crystalline Form A, B, C, D, E, F, G, H, I, or J or the amorphous Form of the compound of formula (I), or a pharmaceutical composition thereof in the manufacture of a medicament for treating hemolytic anemia. In one aspect, the hemolytic anemia to be treated is hereditary and/or congenital hemolytic anemia, acquired hemolytic anemia, or anemia as part of a multisystem disease.

In some aspects, provided herein are methods for treating sickle cell disease in a subject in need thereof comprising administering to the subject an effective amount of crystalline Form A, B, C, D, E, F, G, H, I, or J or the amorphous Form of the compound of formula (I), or a pharmaceutical composition thereof. Also provided is crystalline Form A, B, C, D, E, F, G, H, I, or J or the amorphous Form of the compound of formula (I), or a pharmaceutical composition thereof for use in treating sickle cell disease in a subject in need thereof. Further provided is the use of crystalline Form A, B, C, D, E, F, G, H, I, or J or the amorphous Form of the compound of formula (I), or a pharmaceutical composition thereof in the manufacture of a medicament for treating sickle cell disease.

In some aspects, provided herein are methods for treating thalassemia, hereditary spherocytosis, hereditary elliptocytosis, abetalipoproteinemia or Bassen-Kornzweig syndrome, sickle cell disease, paroxysmal nocturnal hemoglobinuria, acquired hemolytic anemia, or anemia of chronic diseases in a subject in need thereof comprising administering to the subject an effective amount of crystalline Form A, B, C, D, E, F, G, H, I, or J or the amorphous Form of the compound of formula (I), or a pharmaceutical composition thereof. Also provided is crystalline Form A, B, C, D, E, F, G, H, I, or J or the amorphous Form of the compound of formula (I), or a pharmaceutical composition thereof for use in treating thalassemia, hereditary spherocytosis, hereditary elliptocytosis, abetalipoproteinemia or Bassen-Kornzweig syndrome, sickle cell disease, paroxysmal nocturnal hemoglobinuria, acquired hemolytic anemia, or anemia in a subject in need thereof. Further provided is the use of crystalline Form A, B, C, D, E, F, G, H, I, or J or the amorphous Form of the compound of formula (I), or a pharmaceutical composition thereof in the manufacture of a medicament for treating thalassemia, hereditary spherocytosis, hereditary elliptocytosis, abetalipoproteinemia or Bassen-Kornzweig syndrome, sickle cell disease, paroxysmal nocturnal hemoglobinuria, acquired hemolytic anemia, or anemia.

In some aspects, provided herein are methods for activating wild-type or mutant PKR in red blood cells in a subject in need thereof comprising administering to the subject an effective amount of crystalline Form A, B, C, D, E, F, G, H, I, or J or the amorphous Form of the compound of formula (I), or a pharmaceutical composition thereof. Also provided is crystalline Form A, B, C, D, E, F, G, H, I, or J or the amorphous Form of the compound of formula (I), or a pharmaceutical composition thereof for use in activating wild-type or mutant PKR in red blood cells in a subject in need thereof. Further provided is the use of crystalline Form A, B, C, D, E, F, G, H, I, or J or the amorphous Form of the compound of formula (I), or a pharmaceutical composition thereof in the manufacture of a medicament for activating wild-type or mutant PKR in red blood cells.

The provided crystalline Form A, B, C, D, E, F, G, H, I, or J or the amorphous Form of the compound of formula (I), and pharmaceutical compositions described herein are activators of PKR mutants having lower activities compared to the wild type, thus are useful for methods of the present disclosure. Such mutations in PKR can affect enzyme activity (catalytic efficiency), regulatory properties (modulation by fructose bisphosphate (FBP)/ATP), and/or thermostability of the enzyme. Examples of such mutations are described in Valentini et al, JBC 2002. Some examples of the mutants that are activated by the compounds described herein include G332S, G364D, T384M, R479H, R479K, R486W, R532W, R510Q, and R490W. Without being bound by theory, in certain embodiments, the compounds described herein affect the activities of PKR mutants by activating FBP non-responsive PKR mutants, restoring thermostability to mutants with decreased stability, or restoring catalytic efficiency to impaired mutants. The activating activity of the present compounds against PKR mutants may be tested following a method described in the Examples. Compounds described herein are also activators of wild type PKR.

In certain embodiments, the provided crystalline Form A, B, C, D, E, F, G, H, I, or J or the amorphous Form of the compound of formula (I), and pharmaceutical compositions described herein increase the affinity of PKR to phosphoenolpyruvate (PEP). In certain embodiments, the provided crystalline Form A, B, C, D, E, F, G, H, I, or J or the amorphous Form of the compound of formula (I), and pharmaceutical compositions described herein restore the ability of RBCs to cover PEP and ADP to pyruvate and ATP.

In certain embodiments, provided herein are methods of reducing transfusion frequency of a subject with PKD comprising administering to the subject crystalline Form A, B, C, D, E, F, G, H, I, or J or the amorphous Form of the compound of formula (I), and pharmaceutical compositions described herein. In certain embodiments, crystalline Form A is administered. In certain embodiments, the transfusion frequency is reduced by at least 5% in the number of RBC units transfused over at least 15 weeks. In certain embodiments, the transfusion frequency is reduced by at least 10% in the number of RBC units transfused over at least 15 weeks. In certain embodiments, the transfusion frequency is reduced by at least 15% in the number of RBC units transfused over at least 15 weeks. In certain embodiments, the transfusion frequency is reduced by at least 20% in the number of RBC units transfused over at least 15 weeks. In certain embodiments, the transfusion frequency is reduced by at least 25% in the number of RBC units transfused over at least 15 weeks. In certain embodiments, the transfusion frequency is reduced by at least 30% in the number of RBC units transfused over at least 15 weeks. In certain embodiments, the transfusion frequency is reduced by at least 35% in the number of RBC units transfused over at least 15 weeks. In certain embodiments, the transfusion frequency is reduced by at least 40% in the number of RBC units transfused over at least 20 weeks. In certain embodiments, the transfusion frequency is reduced by at least 5% in the number of RBC units transfused over at least 20 weeks. In certain embodiments, the transfusion frequency is reduced by at least 10% in the number of RBC units transfused over at least 20 weeks. In certain embodiments, the transfusion frequency is reduced by at least 15% in the number of RBC units transfused over at least 20 weeks. In certain embodiments, the transfusion frequency is reduced by at least 20% in the number of RBC units transfused over at least 20 weeks. In certain embodiments, the transfusion frequency is reduced by at least 25% in the number of RBC units transfused over at least 20 weeks. In certain embodiments, the transfusion frequency is reduced by at least 30% in the number of RBC units transfused over at least 20 weeks. In certain embodiments, the transfusion frequency is reduced by at least 35% in the number of RBC units transfused over at least 20 weeks. In certain embodiments, the transfusion frequency is reduced by at least 40% in the number of RBC units transfused over at least 20 weeks.

Is some aspects, provided herein are methods of evaluating a subject, the method comprising: administering to the subject crystalline Form A, B, C, D, E, F, G, H, I, or J or the amorphous Form of the compound of formula (I), or a pharmaceutical composition thereof; and acquiring a value for the level of the crystalline or amorphous form, the level of 2,3-diphosphoglycerate (2,3-DPG), the level of adenosine triphosphate (ATP), or the activity of PKR in the subject, to thereby evaluate the subject. In some aspects, the value for the level is acquired by analyzing the plasma concentration of crystalline or amorphous form. In some aspects, the level of 2,3-DPG is acquired by analyzing the blood concentration of 2,3-DPG. In some aspects, the level of ATP is acquired by analyzing the blood concentration of ATP. In some aspects, the activity of PKR is acquired by analyzing the blood concentration of a $^{13}$C-label in the blood. In some aspects, the analysis is performed by sample analysis of bodily fluid. In some aspects, the bodily fluid is blood. In some aspects, the analysis is performed by mass spectroscopy. In some aspects, the analysis is performed by LC-MS.

In some aspects, provided herein are methods of evaluating a subject, the method comprising acquiring, the value for the level of crystalline Form A, B, C, D, E, F, G, H, I, or J or the amorphous Form of the compound of formula (I), or a pharmaceutical composition thereof, the level of 2,3-DPG, the level of ATP, or the activity of PKR in a subject that has been treated with crystalline Form A, B, C, D, E, F, G, H, I, or J or the amorphous Form of the compound of formula (I), or a pharmaceutical composition thereof, to thereby evaluate the subject. In some aspects, acquiring comprises receiving a sample from the subject. In some aspects, acquiring comprises transmitting the value to another party. In some aspects, the other party is the party that administered crystalline Form A, B, C, D, E, F, G, H, I, or J or the amorphous Form of the compound of formula (I), or a pharmaceutical composition thereof.

In some aspects, provided herein are methods of treating a subject, the method comprising: administering to the subject a therapeutically effective amount of crystalline Form A, B, C, D, E, F, G, H, I, or J or the amorphous Form of the compound of formula (I), or a pharmaceutical composition thereof; and acquiring a value for the level of the crystalline or amorphous form, the level of 2,3-diphosphoglycerate (2,3-DPG), the level of adenosine triphosphate (ATP), or the activity of PKR in the subject, to thereby treat the subject.

In another aspect, provided herein are methods of treating Pyruvate Kinase Deficiency (PKD) in a subject in need thereof, comprising administering to the subject an effective amount of crystalline free-base form of Compound 1 or a pharmaceutical composition thereof. In certain embodiments, the deficiency of PKR is associated with a PKR mutation. Also provided is crystalline free-base form of Compound 1, or a pharmaceutical composition thereof, for use in treating Pyruvate Kinase Deficiency (PKD) in a subject in need thereof. Further provided is the use of crystalline free-base form of Compound 1, or a pharmaceutical composition thereof, in the manufacture of a medicament for treating Pyruvate Kinase Deficiency (PKD).

In other aspects, provided are methods of treating a disease selected from hemolytic anemia, sickle cell anemia, thalassemia, hereditary spherocytosis, hereditary elliptocytosis, abetalipoproteinemia, Bassen-Kornzweig syndrome, and paroxysmal nocturnal hemoglobinuria in a subject in need thereof, comprising administering to the subject an effective amount of crystalline free-base form of Compound 1, or a pharmaceutical composition thereof. In one aspect, the disease to be treated is hemolytic anemia.

In other aspects, provided herein are methods for treating hemolytic anemia, comprising administering to the subject an effective amount of crystalline free-base form of Compound 1, or a pharmaceutical composition thereof. Also provided is crystalline free-base form of Compound 1, or a pharmaceutical composition thereof, for use in treating hemolytic anemia in a subject in need thereof. Further provided is the use of crystalline free-base form of Compound 1, or a pharmaceutical composition thereof, in the manufacture of a medicament for treating hemolytic anemia.

In other aspects, provided herein are methods for treating sickle cell disease, comprising administering to the subject an effective amount of crystalline free-base form of Compound 1, or a pharmaceutical composition thereof. Also provided is crystalline free-base form of Compound 1, or a pharmaceutical composition thereof, for use in treating sickle cell disease in a subject in need thereof. Further provided is the use of crystalline free-base form of Compound 1, or a pharmaceutical composition thereof, in the manufacture of a medicament for treating sickle cell disease.

In other aspects, provided herein are methods for treating thalassemia (e.g., beta-thalassemia), comprising administering to the subject an effective amount of crystalline free-base form of Compound 1, or a pharmaceutical composition thereof. Also provided is crystalline free-base form of Compound 1, or a pharmaceutical composition thereof, for use in treating thalassemia (e.g., beta-thalassemia) in a subject in need thereof. Further provided is the use of crystalline free-base form of Compound 1, or a pharmaceutical composition thereof, in the manufacture of a medicament for treating thalassemia (e.g., beta-thalassemia).

In other aspects, provided herein are methods for increasing the lifetime of red blood cells (RBCs) in a subject in need thereof comprising administering to the subject an effective amount of crystalline free-base form of Compound 1, or a pharmaceutical composition thereof. In one aspect, crystalline free-base form of Compound 1, or a pharmaceutical composition thereof is added directly to whole blood or packed red blood cells extracorporeally. Also provided is crystalline free-base form of Compound 1, or a pharmaceutical composition thereof, for use in increasing the lifetime of red blood cells (RBCs) in a subject in need thereof. Further provided is the use of crystalline free-base form of Compound 1, or a pharmaceutical composition thereof, in the manufacture of a medicament for increasing the lifetime of red blood cells (RBCs).

In other aspects, provided herein are methods for regulating 2,3-diphosphoglycerate levels in blood in a subject in need thereof comprising contacting blood with an effective amount of crystalline free-base form of Compound 1, or a pharmaceutical composition thereof. Also provided is crystalline free-base form of Compound 1, or a pharmaceutical composition thereof, for use in regulating 2,3-diphosphoglycerate levels in blood in a subject in need thereof. Further provided is the use of crystalline free-base form of Compound 1, or a pharmaceutical composition thereof, in the manufacture of a medicament for regulating 2,3-diphosphoglycerate levels in blood.

In other aspects, provided herein are methods for treating anemia in a subject in need thereof comprising administering to the subject an effective amount of crystalline free-base form of Compound 1, or a pharmaceutical composition thereof. In one aspect, the anemia to be treated is dyserythropoietic anemia. Also provided is crystalline free-base form of Compound 1, or a pharmaceutical composition thereof, for use in treating anemia in blood in a subject in need thereof. Further provided is the use of crystalline free-base form of Compound 1, or a pharmaceutical composition thereof, in the manufacture of a medicament for treating anemia.

In certain embodiments, provided herein is a method of increasing the amount of hemoglobin in a subject by administering an effective amount of crystalline free-base form of Compound 1, or a pharmaceutical composition thereof. Also provided is crystalline free-base form of Compound 1, or a pharmaceutical composition thereof, for use in increasing the amount of hemoglobin in a subject in need thereof. Further provided is the use of crystalline free-base form of Compound 1, or a pharmaceutical composition thereof, in the manufacture of a medicament for increasing the amount of hemoglobin.

In some aspects, a therapeutically effective amount of a disclosed form (crystalline Form A, B, C, D, E, F, G, H, I, J, the crystalline free-base, or the amorphous form) can be administered to cells in culture, e.g. in vitro or ex vivo, or to a subject, e.g., in vivo, to treat, prevent, and/or diagnose a variety of disorders, including those described herein below.

In one aspect, the disclosed compositions, methods of treatment, and uses thereof, comprising a disclosed form (crystalline Form A, B, C, D, E, F, G, H, I, J, the crystalline free-base, or the amorphous form) further comprise the administration or use of folic acid. The administration or use of folic acid can be prior to, during, and/or following the administration or use of a crystalline or amorphous form described herein. In one aspect, however, the folic acid is administered or used prior to and/or concurrently with a disclosed form (crystalline Form A, B, C, D, E, F, G, H, I, J, the crystalline free-base, or the amorphous form). Thus, in one aspect, provided herein is a method for treating a condition described herein (e.g., PKD, anemia such as hemolytic anemia, acquired hemolytic anemia, and sickle cell anemia, thalassemia (e.g., beta-thalassemia, alpha-thalassemia, non-transfusion dependent thalassemia, etc.), sickle cell disease, hereditary spherocytosis, hereditary elliptocytosis, abetalipoproteinemia, Bassen-Kornzweig syndrome, and paroxysmal nocturnal hemoglobinuria); increasing the lifetime of RBCs; regulating 2,3-diphosphoglycerate levels in blood; activating wild-type or mutant PKR in red blood cells; increasing the amount of hemoglobin; evaluating the level of 2,3-diphosphoglycerate (2,3-DPG), the level of adenosine triphosphate (ATP), or the activity of PKR; evaluating the level of 2,3-diphosphoglycerate (2,3-DPG), the level of adenosine triphosphate (ATP), or the activity of PKR; in a subject in need thereof, comprising administering to the subject an effective of a disclosed form (crystalline Form A, B, C, D, E, F, G, H, I, J, the crystalline free-base, or the amorphous form) and folic acid.

In aspects where folic acid is administered or used prior to a disclosed form (crystalline Form A, B, C, D, E, F, G, H, I, J, the crystalline free-base, or the amorphous form), the folic acid may be used at least 5 days, at least 10 days, at least 15 days, at least 20 days, or at least 25 days prior to the administration or use of disclosed form. In one aspect, the folic acid is administered or used at least 20, at least 21, at least 22, at least 23, at least 24, or at least 25 days prior to the administration or use of disclosed form. In another aspect, the folic acid is administered at least 21 days prior to the administration or use of disclosed form. In another aspect, the folic acid is administered or used from 1 to 30 days prior to the administration or use of disclosed form. In another aspect, the folic acid is administered or used from 5 to 25 days prior to the administration or use of disclosed form. In another aspect, the folic acid is administered or used from 10 to 30 days prior to the administration or use of disclosed form. In another aspect, the folic acid is administered or used from 10 to 25 days prior to the administration or use of disclosed form. In another aspect, the folic acid is administered or used from 15 to 25 days prior to the administration or use of disclosed form. In another aspect, the folic acid is administered or used from 20 to 25 days prior to the administration or use of disclosed form.

Specific amounts of folic acid to be administered or used with a disclosed form will vary depending upon the subject to be treated and the particular mode of administration. In certain aspects, the effective amount of folic acid is about 0.1 mg to about 10 mg daily. In certain aspects, the effective amount of folic acid is at least 0.1, 0.2, 0.3, 0.4, 0.5, 0.6, 0.7, 0.8, 0.9 or 1.0 mg daily. In one aspect, the effective amount of folic acid is at least 0.8 mg daily or at least 1.0 mg daily.

The amount of folic acid is intended to be combined with any amount of a disclosed form described herein. Thus, in certain aspects, provided herein is a method for treating a condition described herein (e.g., PKD, anemia such as hemolytic anemia, acquired hemolytic anemia, and sickle cell anemia, thalassemia (e.g., beta-thalassemia, alpha-thalassemia, non-transfusion dependent thalassemia, etc.), sickle cell disease, hereditary spherocytosis, hereditary elliptocytosis, abetalipoproteinemia, Bassen-Kornzweig syndrome, and paroxysmal nocturnal hemoglobinuria); increasing the lifetime of RBCs; regulating 2,3-diphosphoglycerate levels in blood; activating wild-type or mutant PKR in red blood cells; increasing the amount of hemoglobin; evaluating the level of 2,3-diphosphoglycerate (2,3-DPG), the level of adenosine triphosphate (ATP), or the activity of PKR; evaluating the level of 2,3-diphosphoglycerate (2,3-DPG), the level of adenosine triphosphate (ATP), or the activity of PKR; in a subject in need thereof, comprising administering to the subject an effective amount of a disclosed form described herein (crystalline Form A, B, C, D, E, F, G, H, I, J, the crystalline free-base, or the amorphous form) and folic acid, wherein the folic acid is administered prior to and/or concurrently with the disclosed form (e.g., at least 21 days prior), the disclosed form (e.g. Form A) is administered in an amount of 5, 20, or 50 mg BID and wherein the folic acid is administered in an amount of at least 0.8 mg/day.

EXEMPLIFICATION

As depicted in the Examples below, crystalline and amorphous forms are prepared according to the following general procedures.

Typical abbreviations used are outlined below.

| Name | Abbreviation |
|---|---|
| Solvents | |
| 1-propanol | 1-PA |
| 2-propanol | IPA |
| Acetonitrile | ACN |
| Benzyl Alcohol | BA |
| Dichloromethane | DCM |
| Dimethyl Sulfoxide | DMSO |
| Ethanol | EtOH |
| Ethyl Acetate | EtOAc |
| Isopropyl Acetate | IPAc |
| Methanol | MeOH |
| Methyl Acetate | MeOAc |
| Methyl Butyl Ketone | MBK |
| Methyl Ethyl Ketone | MEK |
| Methyl Isobutyl Ketone | MIBK |
| N,N-Dimethylacetamide | DMAc |
| N,N-Dimethylformamide | DMF |
| N-Methyl Pyrrolidone | NMP |
| tert-Butyl Methyl Ether | MtBE |
| Tetrahydrofuran | THF |
| Trifluoroacetic Acid | TFA |
| Trifluoroethanol | TFE |
| Units | |
| Celsius | C. |
| Degrees | ° |
| Equivalents | eq. |
| Gram | g |
| Hour | hr |
| Kelvin | K |
| Liters | L |
| Milligrams | mg |
| Milliliters | mL |
| Minute | min |
| Second | sec |
| volume | vol. |
| Watt | W |
| weight | wt. |

Powder X-ray diffraction was done using a Rigaku MiniFlex 600. Samples were prepared on Si zero-return wafers. A typical scan is from 2θ of 4 to 30 degrees, with step size 0.05 degrees over five minutes with 40 kV and 15 mA. A high-resolution scan is from 2θ of 4 to 40 degrees, with step size 0.05 degrees over thirty minutes with 40 kV and 15 mA. Typical parameters for XRPD are listed below.

| Parameters for Reflection Mode | |
|---|---|
| X-ray wavelength | Cu Kα1, 1.540598 Å, |
| X-ray tube setting | 40 kV, 15 mA |
| Slit condition | Variable + Fixed Slit System |
| Scan mode | Continuous |
| Scan range (°2 TH) | 4-30 |

| Parameters for Reflection Mode | |
|---|---|
| Step size (°2 TH) | 0.05 |
| Scan speed (°/min) | 5 |

Differential scanning calorimetry was done using a Mettler Toledo DSC$^{3+}$. The desired amount of sample is weighed directly in a hermetic aluminum pan with pin-hole. A typical sample mass for is 3-5 mg. A typical temperature range is 30° C. to 300° C. at a heating rate of 10° C. per minute (total time of 27 minutes). Typical parameters for DSC are listed below.

| Parameters | |
|---|---|
| Method | Ramp |
| Sample size | 3-5 mg |
| Heating rate | 10.0° C./min |
| Temperature range | 30 to 300° C. |
| Method gas | $N_2$ at 60.00 mL/min |

Thermogravimetric analysis and differential scanning calorimetry was done using a Mettler Toledo TGA/DSC$^{3+}$. The desired amount of sample is weighed directly in a hermetic aluminum pan with pin-hole. A typical sample mass for the measurement is 5-10 mg. A typical temperature range is 30° C. to 300° C. at a heating rate of 10° C. per minute (total time of 27 minutes). Protective and purge gasses are nitrogen (20-30 mL/min and 50-100 mL/min). Typical parameters for DSC/TGA are listed below.

| Parameters | |
|---|---|
| Method | Ramp |
| Sample size | 5-10 mg |
| Heating rate | 10.0° C./min |
| Temperature range | 30 to 300° C. |

Dynamic Vapor Sorption (DVS) was done using a DVS Intrinsic 1. The sample is loaded into a sample pan and suspended from a microbalance. A typical sample mass for DVS measurement is 25 mg. Nitrogen gas bubbled through distilled water provides the desired relative humidity. A typical measurement comprises the steps:
1. Equilibrate at 50% RH
2. 50% to 2%. (50%, 40%, 30%, 20%, 10% and 2%)
   a. Hold minimum of 5 mins and maximum of 60 minutes at each humidity. The pass criteria is less than 0.002% change
3. 2% to 95% (2%, 10%, 20%, 30%, 40%, 50%, 60%, 70%, 80%, 90%, 95%)
   b. Hold minimum of 5 mins and maximum of 60 minutes at each humidity. The pass criteria is less than 0.002% change
4. 95% to 2% (95%, 80%, 70%, 60%, 50%, 40%, 30%, 20%, 10%, 2%)
   c. Hold minimum of 5 mins and maximum of 60 minutes at each humidity. The pass criteria is less than 0.002% change
5. 2% to 50% (2%, 10%, 20%, 30%, 40%, 50%)
   d. Hold minimum of 5 mins and maximum of 60 minutes at each humidity. The pass criteria is less than 0.002% change Proton NMR was done on a Bruker Avance 300 MHz spectrometer. Solids are dissolved in 0.75 mL deuterated solvent in a 4 mL vial and transferred to an NMR tube (Wilmad 5 mm thin wall 8" 200 MHz, 506-PP-8). A typical measurement is usually 16 scans. Typical parameters for NMR are listed below.

| Parameters | |
|---|---|
| Instrument | Bruker Avance 300 MHz spectrometer |
| | Bruker Avance 500 MHz spectrometer |
| Temperature | 300 K |
| Probe | 5 mm PABBO BB-1H/DZ-GRD Z104275/0170 |
| Number of scans | 16 |
| Relaxation delay | 1.000 s |
| Pulse width | 14.2500 μs |
| Acquisition time | 2.9999 s |
| | 300 15 Hz |
| Spectrometer frequency | 500.13 Hz |
| Nucleus | 1H |

Karl Fischer titration for water determination was done using a 785 DMP Titrino and 703 Ti Stand equipped with 6.0338.100 double platinum wire electrodes. Samples are dissolved in HPLC grade or anhydrous methanol and titrated with Hydranal-Composite 5. A typical sample mass for the measurement is 0.03-0.10 g. Hydranal 1 wt. % water standard is used for calibration.

Compound 1, i.e., the non-crystalline free base, can be prepared following the procedures described below.

Preparation of ethyl-4-(quinoline-8-sulfonamido) benzoate

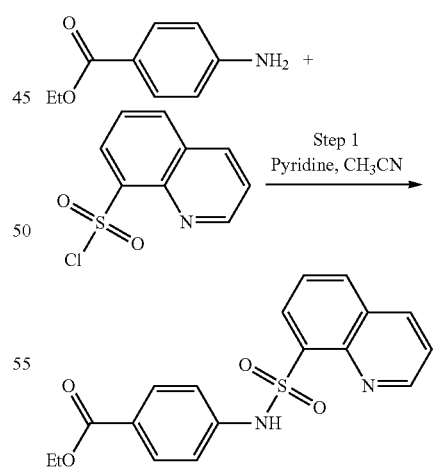

A solution containing ethyl-4-aminobenzoate (16.0 g, 97 mmol) and pyridine (14.0 g, 177 mmol) in acetonitrile (55 mL) was added over 1.2 hours to a stirred suspension of quinoline-8-sulfonyl chloride (20.0 g, 88 mmol) in anhydrous acetonitrile (100 mL) at 65° C. The mixture was stirred for 3.5 hours at 65° C., cooled to 20° C. over 1.5 hours and held until water (140 mL) was added over 1 hour.

Solids were recovered by filtration, washed 2 times (100 mL each) with acetonitrile/water (40/60 wt./wt.) and dried to constant weight in a vacuum oven at 85° C. Analyses of the white solid (30.8 g, 87 mmol) found (A) HPLC purity=99.4% ethyl-4-(quinoline-8-sulfonamido) benzoate, (B) LC-MS consistent with structure, (M+1)=357 (C18 column eluting 95-5, CH3CN/water, modified with formic acid, over 2 minutes), and (C)$^1$H NMR consistent with structure (400 MHz, DMSO-$d_6$)=δ 10.71 (s, 1H), 9.09 (dd, J=4.3, 1.6 Hz, 1H), 8.46 (ddt, J=15.1, 7.3, 1.5 Hz, 2H), 8.26 (dd, J=8.3, 1.4 Hz, 1H), 7.84-7.54 (m, 4H), 7.18 (dd, J=8.6, 1.3 Hz, 2H), 4.26-4.07 (m, 2H), 1.19 (td, J=7.1, 1.2 Hz, 3H).

Preparation of 4-(quinoline-8-sulfonamide) benzoic acid

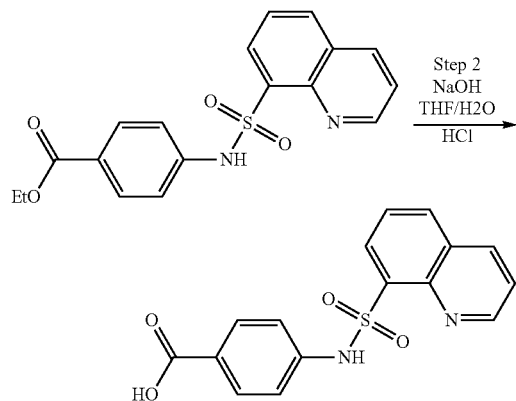

A NaOH solution (16.2 g, 122 mmol) was added over 30 minutes to a stirred suspension of ethyl-4-(quinoline-8-sulfonamido) benzoate (20.0 g, 56.2 mmol) in water (125 mL) at 75° C. The mixture was stirred at 75°-80° C. for 3 hours, cooled 20° C. and held until THF (150 mL) was added. Hydrochloric acid (11% HCL, 81 mL, 132 mmol) was added over >1 hour to the pH of 3.0. The solids were recovered by filtration at 5° C., washed with water (2×100 mL) and dried to constant weight in a vacuum oven at 85° C. Analysis of the white solid (16.7 g, 51 mmol) found (A) HPLC purity=>99.9% 4-(quinoline-8-sulfonamide)benzoic acid, LC-MS consistent with structure (M+1)=329 (C18 column eluting 95-5 CH3CN/water, modified with formic acid, over 2 minutes.) and $^1$H NMR consistent with structure (400 MHz, DMSO-$d_6$)=δ 12.60 (s, 1H), 10.67 (s, 1H), 9.09 (dd, J=4.2, 1.7 Hz, 1H), 8.46 (ddt, J=13.1, 7.3, 1.5 Hz, 2H), 8.26 (dd, J=8.2, 1.5 Hz, 1H), 7.77-7.62 (m, 3H), 7.64 (d, J=1.3 Hz, 1H), 7.16 (dd, J=8.7, 1.4 Hz, 2H).

Preparation of 1-(cyclopropylmethyl)piperazine dihydrochloride (4)

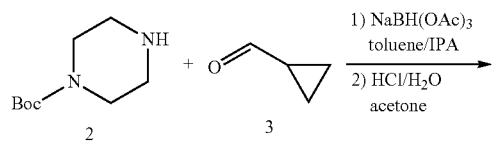

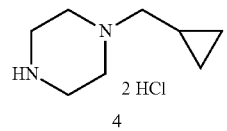

To a 1 L reactor under $N_2$ was charged tert-butyl piperazine-1-carboxylate (2) (100.0 g, 536.9 mmol), cyclopropanecarbaldehyde (3) (41.4 g, 590.7 mmol), toluene (500.0 mL) and 2-propanol (50.0 mL). To the obtained solution was added NaBH(OAc)$_3$ (136.6 g, 644.5 mmol) in portions at 25-35° C. and the mixture was stirred at 25° C. for 2 h. Water (300.0 mL) was added followed by NaOH solution (30%, 225.0 mL) to the pH of 12. The layers were separated and the organic layer was washed with water (100.0 mL×2). To the organic layer was added hydrochloric acid (37%, 135.0 mL, 1.62 mol) and the mixture was stirred at 25° C. for 6 h. The layers were separated and the aqueous layer was added to acetone (2.0 L) at 25° C. in 1 h. The resulted suspension was cooled to 0° C. The solid was filtered at 0° C., washed with acetone (100.0 mL×2) and dried to afford 4 (105.0 g) in 92% isolated yield. LC-MS (C18 column eluting 90-10 CH$_3$CN/water over 2 minutes) found (M+1)=141. $^1$H NMR (400 MHz, DMSO-$d_6$) δ 11.93 (br.s, 1H), 10.08 (br., 2H), 3.65 (br.s, 2H), 3.46 (br.s, 6H), 3.04 (d, J=7.3 Hz, 2H), 1.14-1.04 (m, 1H), 0.65-0.54 (m, 2H), 0.45-0.34 (m, 2H) ppm.

Preparation of N-(4-(4-(cyclopropylmethyl)piperazine-1-carbonyl)phenyl)quinoline-8-sulfonamide (1)

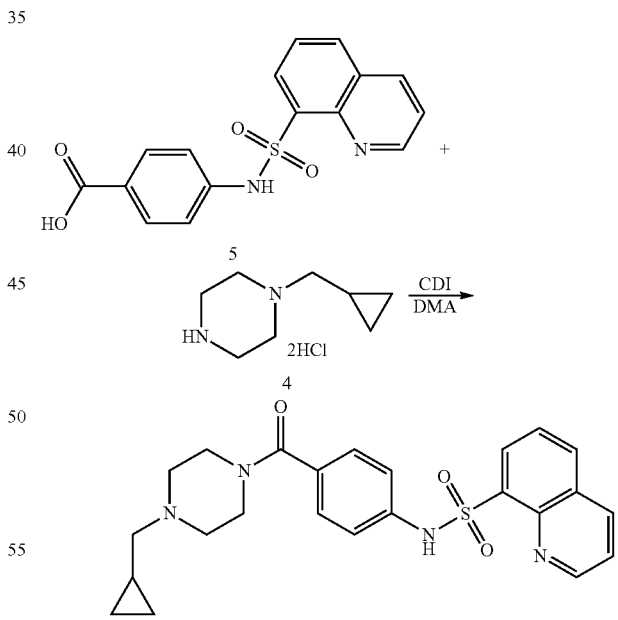

To a 2 L reactor under $N_2$ was charged 4-(quinoline-8-sulfonamido) benzoic acid (5) (100.0 g, 304.5 mmol) and DMA (500.0 mL). To the resulted suspension was added CDI (74.0 g, 456.4 mmol) in portions at 25° C. and the mixture was stirred at 25° C. for 2 h. To the resulted suspension was added 1-(cyclopropylmethyl)piperazine dihydrochloride (4) (97.4 g, 457.0 mmol) in one portion at 25° C. and the mixture was stirred at 25° C. for 4 h. Water (1.0 L) was added in 2 h. The solid was filtered at 25° C., washed with water and dried under vacuum at 65° C. to afford 1 (124.0 g) in 90% isolated yield. LC-MS (C18 column eluting 90-10 CH₃CN/water over 2 minutes) found (M+1)=451. ¹H NMR (400 MHz, DMSO-d₆) δ 10.40 (br.s, 1H), 9.11 (dd, J=4.3, 1.6 Hz, 1H), 8.48 (dd, J=8.4, 1.7 Hz, 1H), 8.40 (dt, J=7.4, 1.1 Hz, 1H), 8.25 (dd, J=8.3, 1.3 Hz, 1H), 7.76-7.63 (m, 2H), 7.17-7.05 (m, 4H), 3.57-3.06 (m, 4H), 2.44-2.23 (m, 4H), 2.13 (d, J=6.6 Hz, 2H), 0.79-0.72 (m, 1H), 0.45-0.34 (m, 2H), 0.07-0.01 (m, 2H) ppm.

Two impurities are also identified from this step of synthesis. The first impurity is Compound IM-1 (about 0.11% area percent based on representative HPLC) with the following structure:

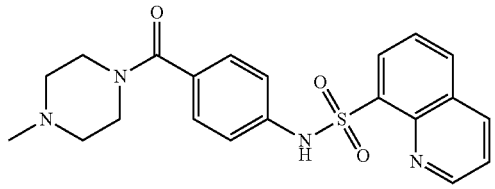

(Compound IM-1)

Compound IM-1 was generated due to the presence of N-methyl piperazine, an impurity in compound 2, and was carried along to react with compound 5. LC-MS found (M+1)=411.2; (M−1)=409.2. ¹H NMR (400 MHz, DMSO-d6) δ 10.43 (brs, 1H) 9.13-9.12 (m, 1H), 8.52-8.50 (m, 1H), 8.43-8.41 (m, 1H), 8.26 (d, J=4.0 Hz, 1H), 7.73-7.70 (m, 2H), 7.15-7.097.69 (m, 4H), 3.60-3.25 (brs, 4H), 2.21 (brs, 4H), 2.13 (s, 3H).

The second impurity is Compound IM-2 (about 0.07% area percent based on the representative HPLC) with the following structure:

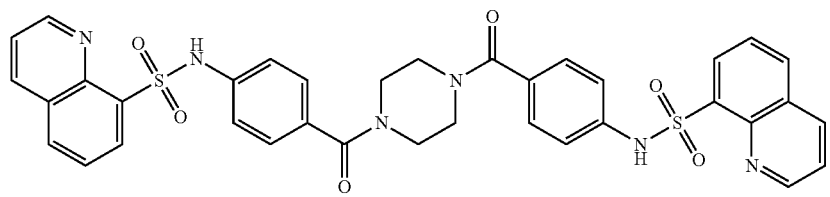

(Compound IM-2)

Compound IM-2 was due to the presence of piperazine, an impurity generated by deprotection of compound 2. The piperazine residue was carried along to react with two molecules of compound 5 to give Compound IM-2. LC-MS found (M+1)=707. ¹H NMR (400 MHz, CF₃COOD) δ 9.30-9.23 (m, 4H), 8.51 (s, 4H), 8.20-8.00 (m, 4H), 7.38-7.28 (m, 8H), 4.02-3.54 (m, 8H).

Solubility Experiments

Solubility measurements were done by gravimetric method in 20 different solvents at two temperatures (23° C. and 50° C.). About 20-30 mg of Form A, the synthesis of which is described below, was weighed and 0.75 mL solvent was added to form a slurry. The slurry was then stirred for two days at the specified temperature. The vial was centrifuged and the supernatant was collected for solubility measurement through gravimetric method. The saturated supernatant was transferred into pre-weighed 2 mL HPLC vials and weighed again (vial+liquid). The uncapped vial was then left on a 50° C. hot plate to slowly evaporate the solvent overnight. The vials were then left in the oven at 50° C. and under vacuum to remove the residual solvent so that only the dissolved solid remained. The vial was then weighed (vial+solid). From these three weights; vial, vial+liquid and vial+solid; the weight of dissolved solid and the solvent were calculated. Then using solvent density the solubility was calculated as mg solid/mL of solvent. Solubility data are summarized in Table 1.

TABLE 1

| Solvent (ratios are volumetric) | Solubility, mg solid/mL solvent | |
|---|---|---|
| | 23° C. | 50° C. |
| MeOH | 393 | >765 |
| EtOH | 0 | 1 |
| IPA | 0 | 2 |
| Acetone | 1 | 6 |
| MtBE | 1 | 3 |
| EtOAc | 0 | 2 |
| Acetonitrile | 4 | 6 |
| Cyclohexane | 1 | 1 |
| MEK:water (20:1) | 0 | 2 |
| Toluene:EtOH:water (10:5:1) | immiscible | immiscible |
| Toluene:EtOH:water (10:5:0.5) | 1 | 4 |
| Toluene | 0 | 2 |
| THF | 2 | 26 |
| IPAc | 0 | 1 |
| acetone:water (8:2) | 5 | 16 |
| THF:water (8:2) | 14 | 77 |
| IPA:DMSO (8:2) | 11 | 28 |
| IPA:DMSO:water (80:18:2) | 1 | 6 |
| IPA:DMSO:water (70:25:5) | 2 | 9 |

TABLE 1-continued

| Solvent (ratios are volumetric) | Solubility, mg solid/mL solvent | |
|---|---|---|
| | 23° C. | 50° C. |
| IPA:DMSO:water (70:20:10) | 1 | 8 |
| DCM | 2 | N/A |

Since the solubility in methanol was significantly high, the measurement was extended to more solvent systems mixed with methanol. Results are shown in Table 2. 20-30 mg of Form A was weighed into 2 mL vial and 500 μL MeOH solvent system as outlined in the table was added. If dissolved, more solids were added to form the slurry. The slurries were then stirred for two days. The vials were centrifuged and the supernatant was collected for solubility measurement through gravimetric method by evaporation at 50° C. XRPD analysis was conducted on the solid after filtration of the slurries.

Water had a significant impact on solubility of Form A. For example in MeOH:water (1:1) system, the room temperature solubility were 208 mg/mL, 118, 39 and 5 for 0 vol %, 1%, 2.5% and 5%, respectively. Therefore, just adding 5 vol % water decreased the solubility 42 fold. Three solvent compositions were used as MeOH:Water (99:1 vol), (98:2) and (95:5). About 25 mg of Form A was weighed into 2 mL vial and 6 volume solvent was added, then slowly heated to dissolve. For experiment with 5% water, an additional test was conducted with 8 vol solvents. See Table 3.

TABLE 2

| Solvent (ratios are volumetric) | Solubility, mg solid/mL solvent | |
|---|---|---|
| | 23° C. | 50° C. |
| MeOH:Water (1:1) | 7 | 27 |
| MeOH:water (8:2) | 10 | 59 |
| EtOAc:MeOH (1:1) | 21 | 240 |
| EtOAc:MeOH (9:1) | 0 | 9 |
| EtOAc:MeOH (1:9) | 359 | 531 |
| EtOH:MeOH (1:1) | 2 | 11 |
| EtOAc:MeOH (1:1) and 5 vol % water | 3 | 12 |
| MeOAc:MeOH (1:1) and 5 vol % water | 5 | 26 |
| MeOAc:MeOH (1:1) | 208 | 340 |
| MeOAc:MeOH (1:1) and 1_vol % water | 118 | 236 |
| MeOAc:MeOH (1:1) and 2.5_vol % water | 39 | 143 |

TABLE 3

| Solvent | Solvent vol | Temperature when dissolution, ° C. | Solubility, mg solid/mL solvent | Extra water | XRPD Pattern |
|---|---|---|---|---|---|
| MeOH:Water (99:1) | 6 vol | 23 | >167 | N/A | B + extra |
| MeOH:Water (98:2) | 6 vol | 35 | 167 | N/A | B |
| MeOH:Water (95:5) | 6 vol | 60 | 167 | 4 vol | A |
| MeOH:Water (95:5) | 8 vol | 50 | 125 | 4 vol | A |

For the sake of comparison, the solubility of Compound 1, i.e., the non-crystalline freebase, was also measured in two solvent systems to see the effect of water. 2.5 vol % water did not have any impact on the solubility of Compound 1. See Table 4.

TABLE 4

| Solvent | Solubility, mg solid/mL solvent | |
|---|---|---|
| | 23° C. | 50° C. |
| MeOAc:MeOH (1:1) | 15 | 34 |
| MeOAc:MeOH (1:1) and 2.5_vol % water | 15 | 36 |

Screening Experiments

1. Short-Term Slurries

Solids from the slurry of solubility measurement experiments were collected for XRPD analysis, shown in Table 5. Pattern A remained unchanged in most solvent systems over the course of two days slurry. In some cases, it lost its crystallinity indicating that stirring longer would possibly change the form. Three new patterns were observed: Pattern B in EtOH at RT and 50° C.; Pattern A+C in IPA at RT; Pattern D in IPA and acetonitrile at 50° C. Pattern D+crystalline free-base in IPA:DMSO (8:2) at 50° C.

In addition, 2 days slurry was performed in methanol solvent mixtures and the results are presented in Table 6. Where at least 2.5 vol % water was present, Pattern A remained unchanged. When only 1% water was present, Pattern A lost its crystallinity at 50° C. while remaining unchanged at room temperature over two days slurry. In anhydrous mixtures where there was substantial amount of methanol, Pattern A was not stable.

TABLE 5

| | XRPD pattern after 2 days slurry | |
|---|---|---|
| Solvent | 23° C. | 50° C. |
| MeOH | A | Low crystalline A |
| EtOH | B | B |
| IPA | A + C | D |
| Acetone | A | A (Extra peak at ~5.8) |
| MtBE | A | A |
| EtOAc | A | A |
| Acetonitrile | A | D |
| Cyclohexane | A | A |
| MEK:water (20:1) | A | A |
| Toluene:EtOH:water (10:5:0.5) | A | A |
| Toluene | A | A |
| THF | A | A |
| IPAc | A | A |
| acetone:water (8:2) | A | A |
| THF:water (8:2) | A | A |
| IPA:DMSO (8:2) | A | D + crystalline free-base |
| IPA:DMSO:water (80:18:12) | A | A |
| IPA:DMSO:water (70:25:5) | A | A |
| IPA:DMSO:water (70:20:10) | A | A |
| DCM | A | N/A |

TABLE 6

| | XPRD pattern after slurry | |
|---|---|---|
| Solvent | RT | 50° C. |
| MeOH:Water (1:1) | A | A |
| MeOH:water (8:2) | A | A |
| EtOAc:MeOH (1:1) | B | D |
| EtOAc:MeOH (9:1) | A | A |
| EtOAc:MeOH (1:9) | A | low crystalline A |
| EtOH:MeOH (1:1) | B | B |
| EtOAc:MeOH (1:1) and 5 vol % water | A | A |

TABLE 6-continued

|  | XPRD pattern after slurry | |
| --- | --- | --- |
| Solvent | RT | 50° C. |
| MeOAc:MeOH (1:1) and 5 vol % water | A | A |
| MeOAc:MeOH (1:1) | A | Lower crystalline A |
| MeOAc:MeOH (1:1) and 1 vol % water | A | Lower crystalline A |
| MeOAc:MeOH (1:1) and 2.5 vol % water | A | A |

2. Crystalline Freebase Slurry Experiments

Compound 1, i.e., the crystalline freebase, was also slurried in a few solvent systems in which the hemisulfate salt showed a different XRPD pattern for the sake of comparison. The freebase remained unchanged after two days slurry. Results are shown in Table 7.

TABLE 7

|  | XPRD pattern after slurry | |
| --- | --- | --- |
| Solvent | 23° C. | 50° C. |
| MeOAc:MeOH (1:1) | FB-A | FB-A |
| MeOAc:MeOH (1:1) and 2.5_vol % water | FB-A | FB-A |
| EtOH | Not performed | FB-A |
| ACN | Not performed | FB-A |
| IPA:water(8:2) | Not performed | FB-A |

FB-A refers to the crystalline free base form of Compound 1

3. Amorphous Generation Experiments

Lyophilization in ACN:water (2:1 vol) was performed to generate amorphous material. About 250 mg of Form A was weighed into 20 mL vial and 6 mL solvent mixture was added, then the mixture was heated to 40° C. and held for 0.5 hr, then put into the freezer (−20° C.). Part of the frozen mixture (about half) was scooped on a filter before melting to analyze. Another half was melted, then 1 mL ACN:water (2:1 vol) and 1 mL water were added, and put it into the freezer again. Finally this mixture was placed in the freeze dryer overnight. XRPD analysis was conducted on the resulting solids. See Table 8.

TABLE 8

| Solvent | XRPD pattern | Method |
| --- | --- | --- |
| 6 mL ACN:water (2:1) | Form E (wet, filter and XRD immediately, 57-1-wet) Form F (dry vacuum oven, 57-1-dry) Form E converted to Form A when the wet cake of Form E was left in the vial overnight | filter |
| 1 mL ACN:water (2:1) + 2 mL water | Form A | Freeze dry |

Based on evaporative crystallization result, amorphous material was observed for the sample in THF. This experiment was repeated, but Pattern D was observed instead. See Table 9.

TABLE 9

| Solvent | Solvent vol, μL | XRPD Pattern |
| --- | --- | --- |
| THF | 13380 | Form D |

The evaporative crystallization in MeOH solvent generated amorphous material. This experiment was repeated at 55° C. by adding 1.5 vol methanol to dissolve Form A. Then the solution was put in vacuum oven at 50° C. overnight. XPRD showed the resulting solid was amorphous. TGA/DSC also showed a small endothermic event accompanied by 2.7% gradual weight loss. See Table 10.

TABLE 10

| Solvent | Solvent vol, μL | XRPD Pattern |
| --- | --- | --- |
| MeOH | 70 | amorphous |

A method to form the free base amorphous form of Compound 1 was found and described as follows.

Figure 23:
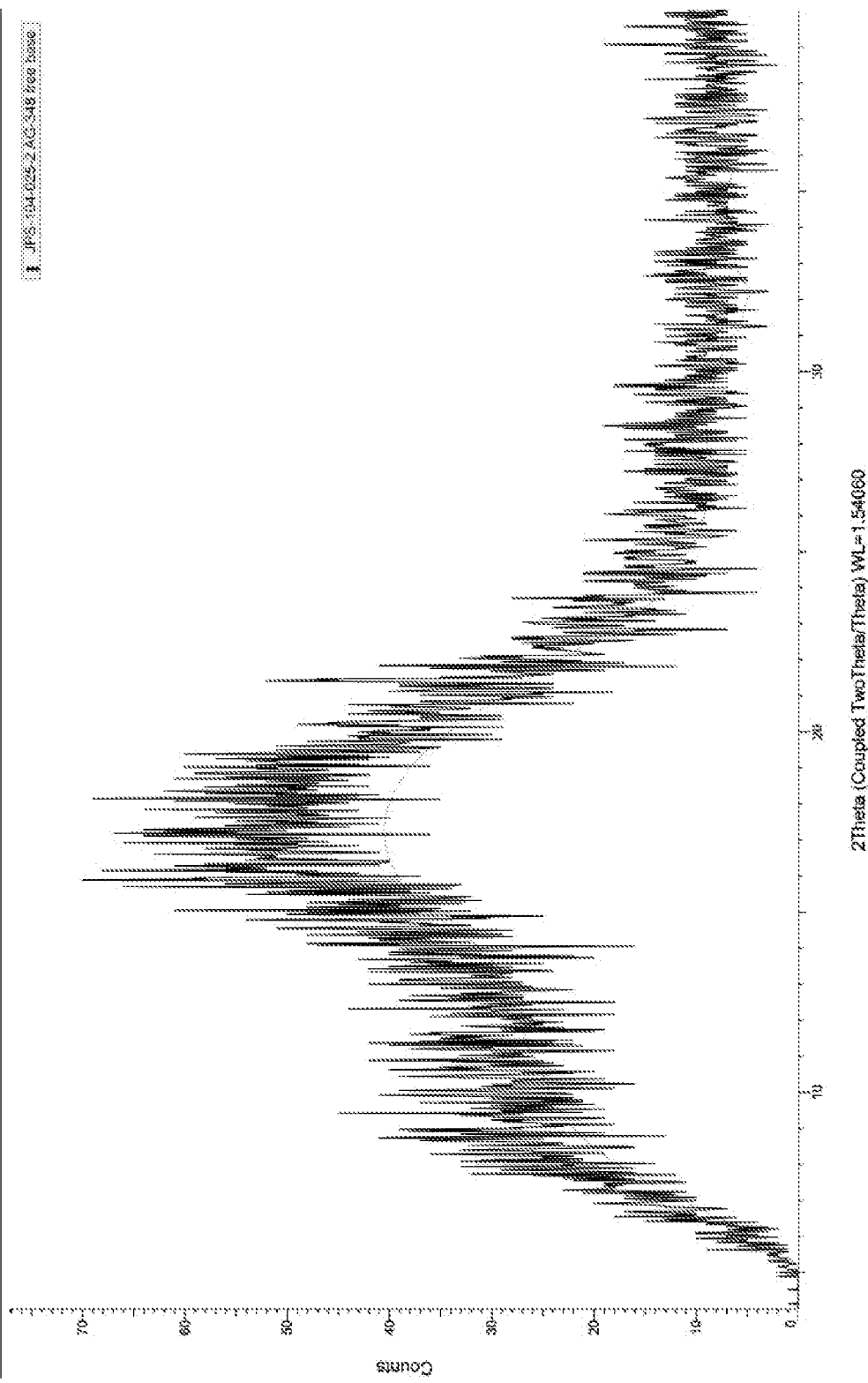
FIG. 23 depicts the X-ray powder diffraction pattern (XRPD) for amorphous free base form of Compound 1.
Figure 24:
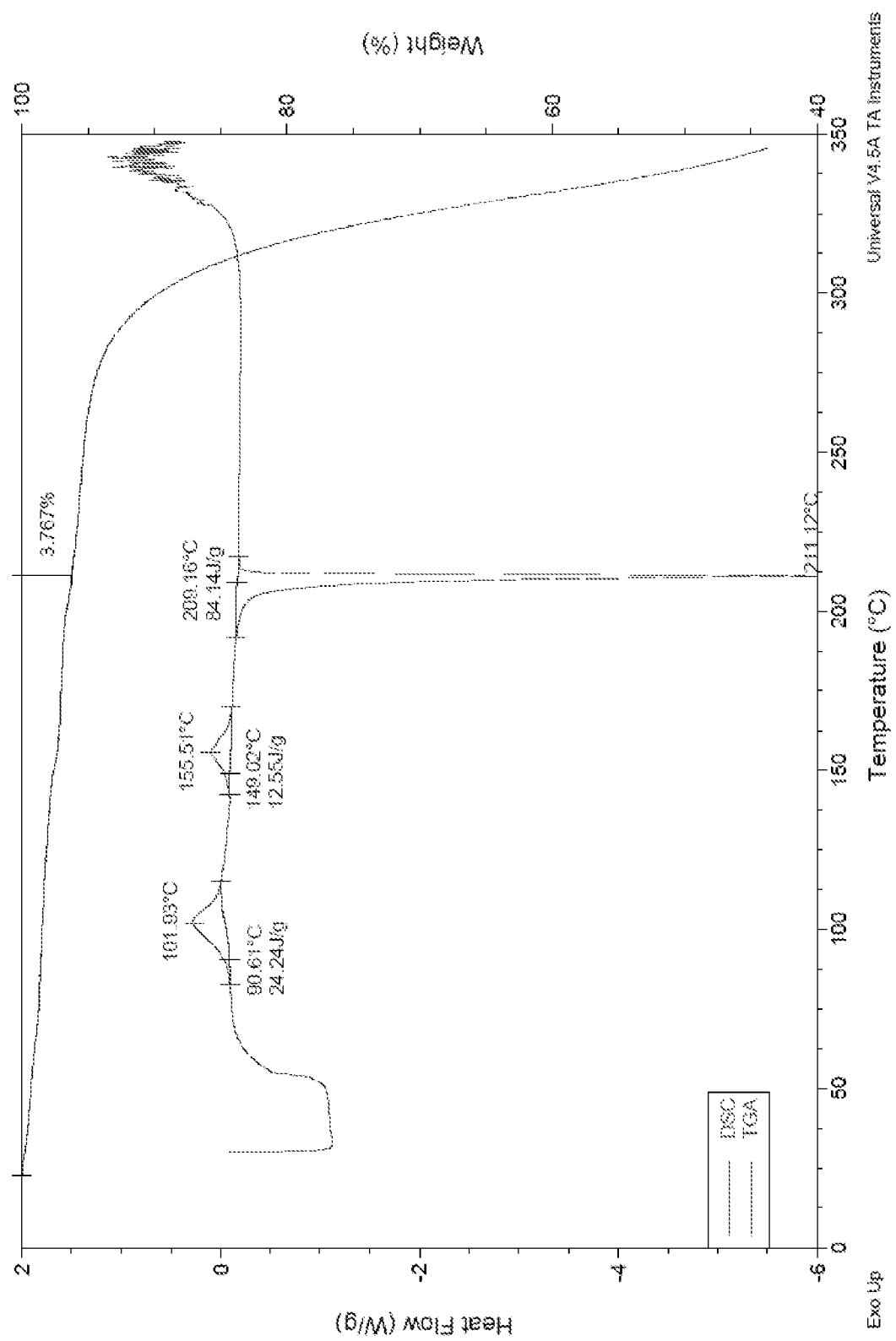
FIG. 24 depicts the TGA and DSC thermograms for amorphous free base form of Compound 1.

About 4 mL of acetonitrile was combined with 2 mL of water. In a 20 mL scintillation vial, excess solid of Compound 1 was suspended in the solvent mixture such that the solids were not completely dissolved. The scintillation vial was capped and the system was placed in room temperature sonication bath for 10-15 minutes. The suspension was filtered through 0.45 μm syringe filter into a 100 mL round bottom flask to obtain a clear solution. The solution was frozen using a dry ice/acetone bath and the frozen solution was placed in a lyophilizer for at least 18 h to obtain the amorphous form of compound 1. The XRPD of the obtained amorphous form is shown in FIG. 23. The TGA and DSC thermograms for the amorphous free base of Compound 1 are shown in FIG. 24.

4. Evaporative Crystallization

About 0.3 mL to 0.5 mL of saturated solution of Form A in various solvent systems were evaporated to dryness and XRPD analysis was performed were applicable. The evaporation was done at 50° C. and under atmospheric pressure (Table 11). The solid was very little for many cases due to low solubility. XPRD pattern remained Pattern A for the samples in MeOH at RT, acetone:water (8:2) at RT and 50° C.; low crystalline freebase was observed in ACN at RT and 50° C.; amorphous was generated in MeOH at 50° C. and in THF at 50° C.

TABLE 11

|  | XRPD pattern by evaporative crystallization | |
| --- | --- | --- |
| Solvent | Slurried at 23° C. | Slurried at 50° C. |
| MeOH | Form A | amorphous |
| EtOH | little solid | little solid |
| IPA | little solid | little solid |
| Acetone | little solid | little solid |
| MeBE | little solid | little solid |
| EtOAc | little solid | little solid |
| ACN | Low crystalline freebase | Low crystalline freebase |
| Cyclohexane | little solid | little solid |
| MEK:water(20:1) | little solid | little solid |
| Toluene:EtOH:water(10:5:1) | little solid | little solid |
| Toluene | little solid | little solid |

TABLE 11-continued

| Solvent | XRPD pattern by evaporative crystallization | |
|---|---|---|
| | Slurried at 23° C. | Slurried at 50° C. |
| THF | little solid | amorphous |
| IPAc | little solid | little solid |
| Acetone:water(8:2) | Form A | Form A |
| THF:water(8:2) | little solid | Low crystalline Form A |
| IPA:DMSO(8:2) | little solid | little solid |
| IPA:DMSO:water(80:18:12) | little solid | little solid |
| IPA:DMSO:water(70:25:5) | little solid | little solid |
| IPA:DMSO:water(70:20:10) | little solid | little solid |
| DCM | little solid | N/A |

Evaporative crystallization was performed in MeOH solvent system after solubility measurement. The results are shown in Table 12. The solid was very little for some cases due to low solubility. XRPD pattern remained Pattern A for the samples in MeOH:Water (1:1) at 50° C., MeOH:water (8:2) at RT and 50° C., and EtOAc:MeOH:water (1:1:0.05) at 50° C.; Pattern B was found in EtOH:MeOH (1:1) at 50° C.; Pattern F was observed in MeOAc:MeOH (1:1:0.05) at 50° C.; Amorphous was generated in EtOAc:MeOH (1:1) at 50° C. and MeOAc:MeOH (1:9) at RT and 50° C.

TABLE 12

| Solvent | XRPD pattern by evaporative crystallization | |
|---|---|---|
| | Slurried at 23° C. | Slurried at 50° C. |
| MeOH:Water (1:1) | Little solid | Form A |
| MeOH:water (8:2) | Form A | Form A |
| EtOAc:MeOH (1:1) | Little solid | Amorphous |
| EtOAc:MeOH (9:1) | Little solid | Little solid |
| EtOAc:MeOH (1:9) | Amorphous | Amorphous |
| EtOH:MeOH (1:1) | Little solid | Form B |
| EtOAc:MeOH (1:1) and 5 vol % water | Little solid | Form A |
| MeOAc:MeOH (1:1) and 5 vol % water | Little solid | Form F |

5. Slow and Fast Cooling Crystallization

Slow and fast cooling experiments were conducted to study the polymorphic behavior of Form A. In the slow cooling experiments, about 20-35 mg Form A was dissolved at 55° C. in various solvent systems and then cooled to RT (23° C.) over 5 hours, and if no precipitation was observed, samples were cooled to 5° C. over 1 hour. In the fast cooling experiments, Form A solutions at 55° C. were cooled quickly to 0° C. by placing the vial in an ice water bath and if no precipitation, samples were placed in −20° C. freezer without mixing to cool down further.

In both fast and slow cooling experiments, no precipitation was observed in IPA:DMSO (7:3) and in IPA:DMSO:water (65:30:5). Form A did not dissolve in 77 volume MeOH:EtOH (3:7). The slurry in MeOH:EtOH (3:7) was filtered and analyzed, which showed conversion to Pattern B. In the fast cooling experiment, two new patterns were obtained: Pattern G in Acetone:water (8:2) and Pattern H in MeOH:EtOAc (1:1). In the slow cooling experiments, resulting solid pattern was Pattern A in Acetone:water (8:2), and Pattern B in MeOH:EtOAc (1:1). See Table 13.

TABLE 13

| Solvent | Solvent vol | XRPD pattern by cooling crystallization | |
|---|---|---|---|
| | | Fast | Slow |
| Acetone:Water (8:2) | 72 | Form G | Form A |
| IPA:DMSO (7:3) | 14 | Not precipitated | Not precipitated |
| MeOH:EtOAc (1:1) | 17 | Form H | Form B |
| IPA:DMSO:water (65:30:5) | 196 | Not precipitated | Not precipitated |
| MeOH:EtOH (3:7) | 77 | undissolved | Undissolved (slurry was Pattern B) |

6. Anti-Solvent Crystallization

Anti-solvent experiments were conducted to further study the polymorphic behavior of the Form A. In direct anti-solvent experiments, the Anti-solvent was added to a solution of 20-25 mg Form A dissolved in 3 volume MeOH with 25 μL increments every time. In reverse addition experiments, the solution was added to 6 volume anti-solvent at once. The experiments were performed at RT. The results are shown in Table 14. Only in MeOH/EtOH system solids were generated during the course of experiments.

TABLE 14

| Solvent (3 vol) | Anti-solvent (6 vol) | Anti-solvent crystallization | | XRPD pattern | |
|---|---|---|---|---|---|
| | | Direct | Reverse | Direct | Reverse |
| MeOH | EtOAc | Precipitated and dissolved quick (no solid) | Precipitated and dissolved quick (no solid) | N/A | N/A |
| MeOH | IPAc | Precipitated and thin slurry, little solid after filtration | Precipitated and gummed | N/A | N/A |
| MeOH | Acetone | Not precipitated | Not precipitated | N/A | N/A |
| MeOH | Ethanol | Precipitated | Gummed | Form B | low crystallinity Form B |
| MeOH | Water | Not precipitated | Not precipitated | N/A | N/A |

7. Solvent Drop Milling Experiment of Salt Pattern A

Solvent drop milling experiments were performed to evaluate the polymorphic behavior of Form A. About 25 mg Form A was weighed in the ball mill capsule, then 25 μL solvent was added. The solid was milled three times, 30 s each time. The solid was scraped off the capsule wall each time to prevent caking. Besides, dry milling of Form A without solvent was designed as reference. XRPD showed that resulting solids remained unchanged after solvent drop milling process except the dry milling sample, which led to a low crystallinity of Form A, almost amorphous. See Table 15.

TABLE 15

| Solvent | Solvent vol, μL | XRPD pattern |
|---|---|---|
| MeOH:water (95:5) | 25 | Form A |

TABLE 15-continued

| Solvent | Solvent vol, μL | XRPD pattern |
|---|---|---|
| Actone:water (8:2) | 25 | Form A |
| MeOH:MeOAc (1:1) | 25 | Form A |
| IPAc | 25 | Low crystalline Form A |
| Anisole | 25 | Form A |
| dry solid | no solvent | Almost amorphous |

8. Hemisulfate Salt Formation

Salt formation was conducted by slurrying Compound 1, i.e., the non-crystalline free base in various solvents followed by adding sulfuric acid solution in EtOAc. First, a sulfuric solution in EtOAc was prepared (concentration approximately 24 wt. %). Then 25 to 30 mg of non-crystalline free base of Compound 1 was weighed in a 2 mL vial, followed by adding 15 vol solvent. The desired number of equivalents of sulfuric acid were then added. The slurries were heated to 45° C. and held for 1 hour and then cooled down to RT over 2 hours, then held overnight. The slurry was filtered and then analyzed by XRPD. The results was shown in Table 16.

TABLE 16

| | observation | | XRPD pattern | |
|---|---|---|---|---|
| Solvent | 0.5 eq. Sulfuric acid | 1.0 eq. sulfuric acid | 0.5 eq. Sulfuric acid | 1.0 eq. sulfuric acid |
| IPA | thin slurry and slight gum | thin slurry and slight gum | low crystallinity FB-A | low crystallinity FB-A |
| Acetonitrile | thin slurry and slight gum | Solution to slurry | Low crystallinity Form A | Form D |
| MeOAc:MeOH (1:1) | Solution* | Solution* | Amorphous | Amorphous |
| EtOAc:MeOH (1:1) | Solution* | Solution* | Amorphous | Amorphous |
| MeOAc:MeOH (1:1); 5% water | Solution* | Solution* | Low crystallinity Form A | Amorphous |
| EtOAc:MeOH (1:1); 5% water | solution to slurry | Solution* | Form A | Amorphous |
| MeOAc:MeOH (1:1); 10% water | Solution* | Solution* | Form A | Amorphous |
| Acetone | Slurry | thin slurry and slight gum | low crystallinity FB-A | Form D |
| THF | Slurry | Slurry | low crystallinity FB-A | low crystallinity FB-A |
| Ethanol | Slurry | solution to slurry | Form I | Form D |
| IPAc | thin slurry and slight gum | thin slurry and slight gum | FB-A | low crystallinity FB-A |
| MeOAc:MeOH (1:1); 1% water | Solution* | Solution* | low crystallinity FB-A | Amorphous |

*No precipitation after 3-4 hrs of stirring, then the solvent was evaporated. FB-A refers to the crystalline free-base form of Compound 1

The hemisulfate was also formed in MeOAc:MeOH (1:1) mixture with and without water. A sulfuric acid solution in water of 43 wt % (density: 1.3072 g/mL) was prepared and used for hemisalt formation. See Table 17.

TABLE 17

Salt formation in MeOAc:MeOH solvent system with 0.52eq sulfuric acid solution in water (40 to 50 wt %)

| sulfuric acid, eq | sulfuric acid solution in water, μL | Solvent, μL | Experiment description | XPRD Pattern-wet solid |
|---|---|---|---|---|
| 0.52 | 19.4 | 578.4 | Added 6 volume MeOAc:MeOH (1:1) at RT; Added 0.52 eq. acid; solution achieved with some specs of solid Added Pattern A as seed. Added Pattern B as seed Held 1 hr. became thick. Sampled for XRPD. Heated to 50° C. | Form J |
| 0.52 | 18.6 | 555 | Added 6 volume MeOAc:MeOH (1:1) at RT Added 0.52 eq. acid; solution achieved with some specs of solid Added 0.4 vol water dropwise Hold 2 hrs. became thick. Filtered for XRPD | Form A |
| 0.52 | 19.8 | 591 | Added 6 volume MeOAc:MeOH (1:1) at RT Heated to 45 C. Added 0.52 eq. acid; solution achieved with some specs of solid Added 0.4 vol water dropwise Held for 30 mins and cool to RT over 1 hr Held 1 hr. became thick. Filtered for XRPD | Form A |
| 0.52 | 18.6 | 555.6 | Added 6 volume MeOAc:MeOH (1:1) at RT Added 0.52 eq. acid; solution achieved with some specs of solid Added 1 vol water over 2 hrs Held 1 hr. became thick. Filtered for XRPD | Form A |

Hemisulfate salt formation was also conducted by slurrying Compound 1 in methanol followed by adding sulfuric acid solution in water (43 wt % aq.). About 100 mg Compound 1, the non-crystalline free base, was weighed in a 4 mL vial, followed by adding 6 vol solvent. 0.52 equivalents of sulfuric acid solution in water (concentration approximately 43 wt. %) was then added which resulted in complete dissolution at room temperature. For experiment 1, one volume water was added dropwise first, tiny amount of Pattern A was added as seeds, then 5 volume water was added over 1 hour; for experiment 2, no water was added, both Patterns A and B were added as seeds; for experiment 3, six volume water was added over 2 hours, no seed. All vials were stirred overnight (O/N). The slurry was filtered and then analyzed by XRPD. Yield was about 80% for the experiment with adding water and about 60% for the experiment without adding water, refer to Table 18.

TABLE 18

| Solvent | Solvent vol, μL | Sulfuric add in Water μL | Water Added μL | Final composition | Seeds added | XRPD pattern | Yield |
|---|---|---|---|---|---|---|---|
| MeOH | 572 | 19.2 | 595 | MeOH:water (50:50) | Form A | Form A | 84% |
| MeOH | 552 | 18.4 | no water | MeOH:water (98.5:1.5) | Form A + B | Form B | 63% |
| MeOH | 577 | 19.4 | 600 | MeOH:water (50:50) | no seed | Form A | 82% |

Hemisulfate salt formation was also performed in methanol:water (95:5) by using freebase and sulfuric acid. About 150 mg of Compound 1 was weighed into 4 mL vial and 8 volume solvent was added. The mixture was stirred at 500 rpm and then 0.52 eq. sulfuric acid solution in water (concentration approximately 43 wt. %) was added. This mixture was heated to 45° C. which resulted in complete dissolution followed by adding 0.5 volume water, then cooled to RT and held O/N. This resulted in a flowable slurry. 3.5 vol water was then added and filtered. XRPD analysis showed Pattern A. Yield was about 84%. Refer to Table 19.

TABLE 19

| Solvent | Solvent μL | Sulfuric add in Water μL | Temperature (heated to), ° C. | Final composition | XRPD pattern | yield |
|---|---|---|---|---|---|---|
| MeOH:water (95:5) | 1200 | 30.2 | 45 | MeOH:water (63:37) | Form A | 84% |

A scale-up experiment for Form A proceeded as follows.

About 1.0253 g of Compound 1 was added to a 100 mL flask. 8 vol MeOH:water (95:5 vol) solvent (8.2 mL) was then added and the mixture was stirred at 300 rpm using a 4-pitch blade turbine (4-PBT) impeller with diameter of 3.5 cm. 0.52 eq. sulfuric acid in water (~43 wt. %) (206 μL) was manually added and the mixture was heated from 23° C. to 45° C. over 10 min, which resulted in complete dissolution. 0.5 vol water (0.512 mL) was added and the solution was held for 10 mins, cooled to 23° C. over 1 hr and held while stirring overnight. No precipitation was observed. 4 vol water was then over 1 hr and the solution remained clear throughout water addition at room temperature. Precipitation started shortly (15-30 mins) after completion of water. A sample was analyzed via XRPD which showed Pattern A. The mixture was then cooled down to 15° C. over 1 hour, held for 3 hrs while stirring, and then filtered and washed by 2 vol MeOH:water (1:1). XRPD of the wet cake showed Pattern A. The product was dried overnight in a vacuum oven at 50° C. Yield 1.1143 g salt Pattern A by XRPD. Residual methanol was 0.18 wt % by NMR. pH of the filtrate was measured using pH meter and showed a value of 2.63.

9. Hemisulfate Salt Scale-Up

Hemisulfate salt was produced at 2 gram scale as detailed below. The resulting solid was hemisulfate salt Form A. The yield was about 88%.

About 1.9581 g Compound 1 was added to a 100 mL flask. 8 vol MeOH:water (95:5 vol) solvent (15.9 mL) was added and the mixture was stirred at 300 rpm using a 4-PBT impeller with diameter of 3.5 cm. 0.52 eq. of sulfuric acid in water (~43 wt. %) (399 μL) was manually added. The mixture was heated from 23° C. to 45° C. over 10 min which resulted in complete dissolution. 0.5 vol water (0.993 mL) was added, and the solution was held for 10 mins and cooled to 23° C. over 1 hr. 4 vol water was added over 1 hour and nucleation was observed after about 45 mins of hold while stirring. The mixture was cooled down to 15° C. over 1 hour, held for about 30 mins while stirring, and filtered and washed by 2 vol MeOH:water (1:1). XRPD of the wet cake showed Pattern A. The product was dried overnight in the vacuum oven at 50° C. This Yielded in 2.04 g (88%) salt Pattern A by XRPD. The residual methanol was 0.16 wt % by NMR.

10. Optimized Crystalline Form A Hemisulfate Salt Scale-Up Procedure

An optimized preparation of Form A as a hemisulfate sesquihydrate salt with and without seeding is provided below.

Preparation of 1-(cyclopropylmethyl)-4-(4-(quinoline-8-sulfonamido)benzoyl)piperazin-1-ium sulfate trihydrate (Form A) with seeding

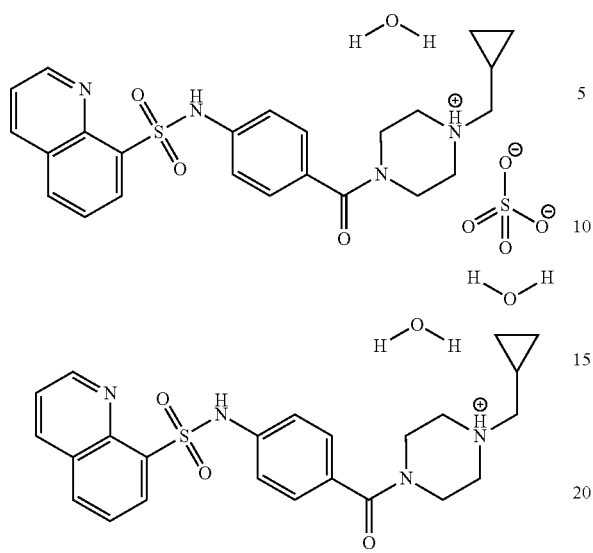

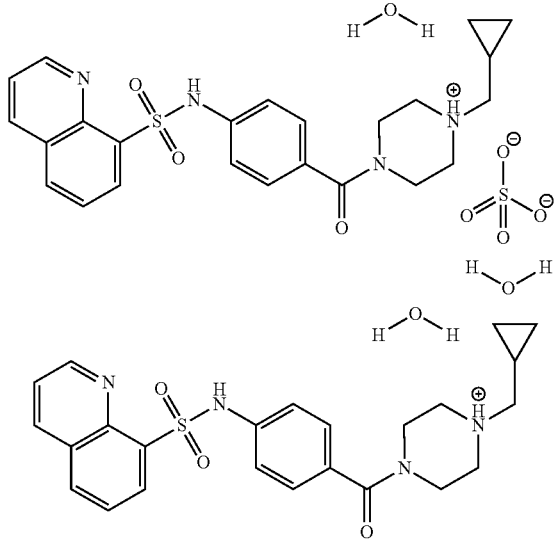

To a 2 L reactor under N₂ was charged N-(4-(4-(cyclopropylmethyl)piperazine-1-carbonyl)phenyl)quinoline-8-sulfonamide (5) (111.0 g, 246.4 mmol), and a pre-mixed process solvent of ethanol (638.6 g), toluene (266.1 g) and water (159.6 g). The suspension was stirred and heated above 60° C. to dissolve the solids, and then the resulting solution was cooled to 50° C. To the solution was added an aqueous solution of H₂SO₄ (2.4 M, 14.1 mL, 33.8 mmol), followed by 1-(cyclopropylmethyl)-4-(4-(quinoline-8-sulfonamido)benzoyl)piperazin-1-ium sulfate trihydrate (6) (1.1 g, 2.1 mmol). After 1 h stirring, to the suspension was added an aqueous solution of H₂SO₄ (2.4 M, 42.3 mL, 101.5 mmol) over 5 h. The suspension was cooled to 22° C. and stirred for 8 h. The solids were filtered at 22° C., washed with fresh process solvent (2×175 g) and dried to give the product (121.6 g) in 94% isolated yield. LC-MS (C18 column eluting 90-10 CH₃CN/water over 2 minutes) found (M+1)=451. ¹H NMR (400 MHz, DMSO-d₆) δ 10.45 (s, 1H), 9.11 (dd, J=4.2, 1.7 Hz, 1H), 8.50 (dd, J=8.4, 1.7 Hz, 1H), 8.41 (dd, J=7.3, 1.5 Hz, 1H), 8.27 (dd, J=8.2, 1.5 Hz, 1H), 7.79-7.60 (m, 2H), 7.17 (d, J=8.4 Hz, 2H), 7.11 (d, J=8.4 Hz, 2H), 3.44 (d, J=8.9 Hz, 5H), 3.03-2.50 (m, 6H), 0.88 (p, J=6.3 Hz, 1H), 0.50 (d, J=7.6 Hz, 2H), 0.17 (d, J=4.9 Hz, 2H).

Preparation of 1-(cyclopropylmethyl)-4-(4-(quinoline-8-sulfonamido)benzoyl)piperazin-1-ium sulfate trihydrate (Form A) without seeding

To a 50 L reactor was charged N-(4-(4-(cyclopropylmethyl)piperazine-1-carbonyl)phenyl)quinoline-8-sulfonamide (5) (1.20 kg, 2.66 mol) and water (23.23 L) at 28° C. While stirring the suspension, an aqueous solution of H2SO4 (1.0 M, 261 g) was added dropwise over 2 h. The reaction was stirred at 25-30° C. for 24 h. The solids were filtered and dried under vacuum below 30° C. for 96 h to give the product (1.26 kg) in 90% isolated yield.

11. Reproduction and Preparation of Various Patterns

The patterns observed during the previous experiments were reproduced for characterization. Patterns B, D, E, F were reproducible. Pattern G was reproduced at lower crystallinity. Pattern I was reproduced, although, it was missing a few peaks. Refer to Table 20.

TABLE 20

| Target Pattern | Actual Pattern | Solvent | Method | Description |
|---|---|---|---|---|
| Form B | Form B | EtOH | slurry at RT | Holds methanol or ethanol. Upon drying loses crystallinity |
| Form C + A | Form A | IPA | slurry at RT | Pattern C was not reproducible as it might be so unstable and converts to Pattern A |
| Form D | Form A + D | ACN | slurry at 50 ° C. | Pattern D is Anhydrous |
| Form B | Form B | EtOH:MeOH (3:7) | Slurry at 55 ° C. | Pattern B obtained |
| Form E | Form E | ACN:water (2:1) | −20° C. cooling crystallization | Very low yield (5%) Unstable upon drying and converts to F |
| Form F | Form F | N/A | Obtained by drying Pattern E at 50° C. and vacuum | About 8 wt % loss in TGA which should be water based on NMR |
| Form G | Low crystalline Form G | ACN:water (8:2) | Fast cooling crystallization & −20° C. | About 5 wt % loss in TGA which should be water based on |

TABLE 20-continued

| Target Pattern | Actual Pattern | Solvent | Method | Description |
|---|---|---|---|---|
| Form H | Almost amorphous solid. Most peaks are missing | MeOH:EtOAc (1:1) | Fast cooling crystallization & −20° C. | NMR Possible solvate very low crystalline |
| Form B | Form B | MeOH:water (99:1) | Dissolved at RT and seed with pattern A and B | Pattern B obtained. |
| Form I | Form I - missing a few peaks | EtOH | Salt formation with freebase and sulfuric in EtOAc | Contained 8.5 wt % EtOH. Possible solvate |
| Form D | Form D | ACN | Salt formation with freebase and sulfuric acid in EtOAc | Pattern D is Anhydrous |

Form B

Form B can be prepared by slurrying Form A in about 10 volumes ethanol at room temperature for a number of days until Form B is obtained. Form B is typically dried Drying at 50° C. under vacuum. Other methods of forming Form B are described above, e.g., in Tables 5, 6, 12-14, 18, and 20.

Form C

Form C is formed as a mixture with Form A after slurrying Form A in IPA for 2 days at about 23° C. See e.g., Table 5. XRPD peaks for Form C are obtained from subtracting the Form A peaks.

Form D

Form D is formed by adding 15 vol acetonitrile and then 0.52 eq. sulfuric acid to compound 1 and heating the mixture to 50° C. The mixture is then held at 50° C. for 30 mins and cooled to RT. The resulting product, Form D, is then Filtered and dried. In an alternative, Form A can be slurried in IPA or acetonitrile at more than 50° C. for at least 2 days to convert to Form D. The latter method was not as robust as the first procedure in which freebase is used. Additional methods are described above, e.g., in Tables 5, 6, 9, 16, and 20.

Form E

Form E can be prepared by adding 24 volume acetonitrile:water (2:1) to Form A and heating the mixture to 50° C. to dissolve the material. The solution is then cooled to −20° C. and left overnight. The resulting product, Form E, is then filtered. See e.g., Table 8 and 20.

Form F

Form F can be prepared by drying Form E at 50° C. under vacuum. See e.g., Table 20. Additional methods are described above, e.g., in Tables 8 and 12.

Form G

Form G can be prepared by adding 72 volume acetonitrile:water (8:2) to Form A and then heating the mixture to 50° C. to dissolve the solids. The solution is then rapidly cooled to −20° C. and left overnight to produce Form G. See e.g., Table 20. Additional methods are described above, e.g., in Table 13.

Form H

Form H can be prepared by dissolved Form A in 40 volume MeOH:EtOAc (1:1) at 50° C., and then placing the solution in ice to crash cool the solution and then cooling the solution to −20° C. The resulting precipitate, Form H, is then filtered and analyzed as wet cake. See e.g., Table 20. Reproducing Pattern H resulted in an amorphous like solid which does not have peaks of Form H. Additional methods are described above, e.g., in Tables 13.

Form I

Form I is a possible solvate that can be prepared by adding 15 volumes of ethanol to compound 1 and heating the mixture to 45° C. to obtain a slurry. 0.52 eq. sulfuric acid in EtOAc is then added and the mixture is held for 1 hr then cooled to room temperature over 2 hours, held for 1 hr and filtered. The product, Form I, is then dried at 50° C. and vacuum. See e.g., Tables 16 and 20.

Form J

Form J can be formed by adding compound 1 and 6 volume MeOAc:MeOH (1:1) at room temperature. 0.52 eq. of sulfuric acid diluted to 43 wt % in water is then added. The slurry is then heated to 60° C. to dissolve the mixture, and the solution is cooled to RT and filtered. Form J is was obtained as wet cake, which converts to Form A upon drying. See e.g., Table 17.

Crystalline Free Base Form of Compound 1

The crystalline free-base form of Compound 1 can be prepared via the following method.

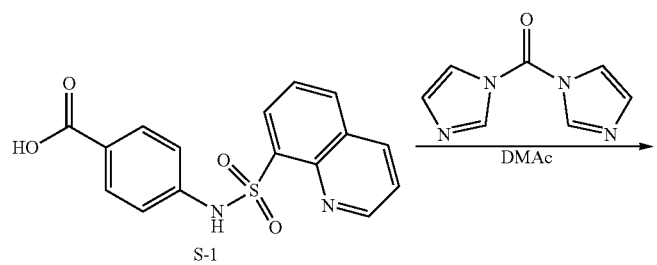

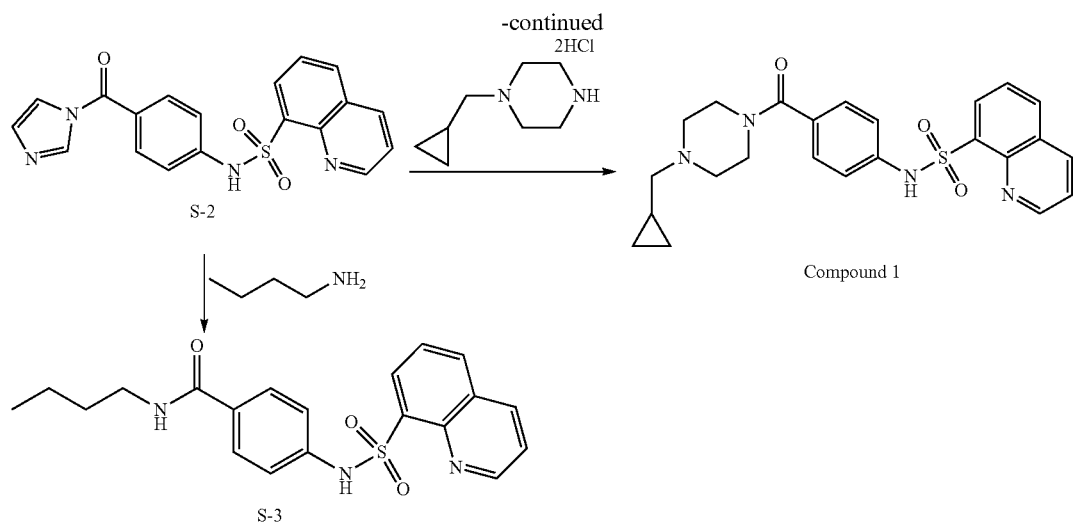

Compound 1

14.8 kg S-1 and 120 kg DMAc are charged into a round bottom under N2 protection and the reaction is stirred at 30° C. under N2 protection for 40 min, to obtain a clear yellow solution. 7.5 kg CDI (1.02 eq.) is added and the reaction is stirred at 30° C. for 2.5 h under N2 protection. 0.6 kg of CDI (0.08 eq.) at 30° C. was added and the mixture was stirred at 30° C. for 2 h under N2 protection. The reaction was tested again for material consumption. 11.0 kg (1.14 eq.) 1-(cyclopropylmethyl)piperazine chloride was charged in the round bottom at 30° C. and the reaction was stirred under N2 protection for 6 h (clear solution). 7.5×$H_2O$ was added dropwise over 2 h, some solid formed and the reaction was stirred for 1 h at 30° C. 16.8×$H_2O$ was added over 2.5 h and the reaction was stirred stir for 2.5 h. 3.8 kg (0.25×) NaOH (30%, w/w, 0.6 eq.) was added and the reaction was stirred for 3 h at 30° C. The reaction was filtered and the wet cake was rinsed with $H_2O$/DMAc=44 kg/15 kg. 23.35 kg wet cake was obtained (KF: 4%). The sample was re-crystallized by adding 10.0×DMAc and stirred for 1 h at 70° C., clear solution; 4.7×$H_2O$ was added over 2 h at 70° C. and the reaction was stirred 2 h at 70° C.; 12.8×$H_2O$ was added dropwise over 3 h and stirred for 2 h at 70° C.; the reaction was adjusted to 30° C. over 5 h and stirred for 2 h at 30° C.; the reaction was filtered and the wet cake was rinsed with DMAc/H2O=15 kg/29 kg and 150 kg H2O. 19.2 kg wet cake was obtained. The material was recrystallized again as follows. To the wet cake was added 10.0×DMAc and the reaction was stirred for 1 h at 70° C., clear solution. 16.4×$H_2O$ was added dropwise at 70° C. and the reaction was stirred for 2 h at 70° C. The reaction was adjusted to 30° C. over 5.5 h and stirred for 2 h at 30° C. The reaction was centrifuged and 21.75 kg wet cake was obtained. The material was dried under vacuum at 70° C. for 25 h. 16.55 kg of the crystalline free base form of compound 1 was obtained. Purity of 99.6%.

12. Solubility in Water and Simulated Fluid

Solubility of Patterns A, B and D were measured in water. The solids were slurried in the fluids for two days and at 37° C. The supernatant was syringe filtered and used for HPLC analysis. For Patterns A and D the solubility measurement was repeated and the sample was taken after 1 hr slurry. A calibration curve was developed using Pattern A. This was not assay corrected and therefore the solubility values are based on the hemi-sulfate, sesqui-hydrate salt.

Both Patterns B and D converted to Pattern A after two days slurry. Pattern D also converted to Pattern A within 1 hour slurry in Fasted state simulated gastric fluid (FaSSGF) or water. Only in Fasted State Simulated Intestinal Fluid (FaSSIF), Patterns A and B disproportionated to crystalline free base after two days slurry and showed lower solubility. Pattern D, however, did not disproportionate in FaSSIF and instead converted to Pattern D. The solubility in water and the simulated fluid of the three patterns were not significantly different. This could be because of the conversion of Patterns B and D to Pattern A. The solubility data and the resulting XRPD Pattern after the measurement are reported in Table 21.

TABLE 21

Solubility in simulated fluids at 37° C.

| | Pattern | Solubility mg Solid/mL solvent | Pattern | Slurry time |
|---|---|---|---|---|
| Water | A | 2.69 | A | 2 days |
| Water | B | 3.02 | A | 2 days |
| Water | D | 2.71 | A | 2 days |
| FaSSIF | A | 0.24 | FB | 2 days |
| FaSSIF | B | 0.20 | FB | 2 days |
| FaSSIF | D | 3.49 | A | 2 days |
| FaSSGF | A | 6.80 | Not enough solid to do XRPD | 2 days |
| FaSSGF | B | 6.53 | A | 2 days |
| FaSSGF | D | 5.94 | A | 2 days |
| Water | A | 3.05 | A | 1 hr |
| FaSSGF | A | 7.07 | A | 1 hr |
| Water | D | 2.62 | A | 1 hr |
| FaSSGF | D | 5.43 | A | 1 hr |

FB means crystalline free base of compound 1.

13. Competitive Slurry

Four different solvents were used for competitive slurry experiments. Four solvent systems were selected for competitive slurry at two different temperatures. The solvents were acetone, acetone:water (9:1), IPA and MeOH:water (95:5) and the temperatures were 23° C. and 50° C. All the solvents were initially saturated by slurrying Pattern A at the target temperatures for about 2 hours then the stir bars were removed and kept the vial at the target temperature allowing the solid to settle. Then the saturated supernatant was transferred into new empty vials which were already heated to the target temperatures on hot plate. Then 5-10 mg each of Patterns A, B and D was added to these saturated solutions. The solid mixture was slurried using stir bar and the first sample was taken after 2 days of slurry. The second sample was taken after 1 week. Pattern A was stable in the solvents that contained water. Pattern D was stable in anhydrous systems especially at higher temperatures. It appears that Pattern D which is anhydrous solid is the most stable solid when anhydrous organic solvents are used. See Table 22.

TABLE 22

| Solvent | Initial Pattern | XPRD pattern - 2 days | | XPRD pattern - 1 week | |
|---|---|---|---|---|---|
| | | RT | 50° C. | RT | 50° C. |
| Acetone | A + B + D | A + D | D | A + D | D |
| Acetone:water (9:1) | A + B + D | A | A | A | A |
| IPA | A + B + D | D | D | D | D |
| MeOH:water (95:5) | A + B + D | A | Not enough sample for XRPD | A | — |

14. Stability Study

No degradation was observed in the stability study of Form A in the following three conditions: one month under 40±2° C./75±5% RH, three months under 25±2° C./60±5% RH, three months at 30±2° C./65±5% RH, three months under 40±2° C./75% RH, twelve months under 25±2° C./60±5% RH.

15. Exemplified Tablet Composition

Form A has been formulated into a tablet either through direct compression of the direct blend formulation or via a dry granulation or wet granulation process. Other excipients can be added, such as binders, and/or surfactants, and coating films to aid tablet integrity, taste masking and aesthetics. An exemplified tablet composition is as follows:

| Component | % w/w of Component |
|---|---|
| Form A | 11.70% |
| Microcrystalline Cellulose NF | 60.18% |
| Mannitol | 23.12% |
| Croscarmellose Sodium | 3.00% |
| Sodium Stearyl Fumarate | 2.00% |
| % Total | 100.00% |

15. Characterization Summary i). Form A

The XRPD for Form A is shown by FIG. 1 and the peak listings are shown in Table 23.

TABLE 23

| Angle, 2-θ | d spacing (A°) | Height (counts) | Rel. Int. |
|---|---|---|---|
| 4.9 | 17.8305 | 40 | 0.28% |
| 9.9 | 8.9545 | 9363 | 66.02% |
| 11.0 | 8.02613 | 2418 | 17.05% |

TABLE 23-continued

| Angle, 2-θ | d spacing (A°) | Height (counts) | Rel. Int. |
|---|---|---|---|
| 11.4 | 7.7313 | 4177 | 29.45% |
| 11.7 | 7.56421 | 3209 | 22.63% |
| 12.3 | 7.16163 | 635 | 4.48% |
| 12.8 | 6.93632 | 2500 | 17.63% |
| 13.6 | 6.51539 | 2286 | 16.12% |
| 13.9 | 6.38771 | 1644 | 11.59% |
| 14.2 | 6.23136 | 3520 | 24.82% |
| 15.0 | 5.88897 | 5689 | 40.11% |
| 15.3 | 5.78752 | 4085 | 28.80% |
| 15.8 | 5.60806 | 12313 | 86.82% |
| 17.1 | 5.17018 | 7400 | 52.18% |
| 17.4 | 5.07818 | 2144 | 15.12% |
| 17.7 | 4.99463 | 4146 | 29.23% |
| 18.8 | 4.71113 | 2437 | 17.18% |
| 19.1 | 4.63884 | 1177 | 8.30% |
| 19.8 | 4.49007 | 3657 | 25.79% |
| 21.3 | 4.17694 | 6577 | 46.38% |
| 21.9 | 4.04794 | 6503 | 45.85% |
| 22.6 | 3.92853 | 14182 | 100.00% |
| 23.0 | 3.86945 | 1915 | 13.50% |
| 23.2 | 3.82274 | 2764 | 19.49% |
| 23.5 | 3.78695 | 4288 | 30.24% |
| 23.8 | 3.73813 | 2177 | 15.35% |
| 24.1 | 3.68699 | 1723 | 12.15% |
| 24.5 | 3.63374 | 2387 | 16.83% |
| 25.3 | 3.51767 | 3957 | 27.90% |
| 25.6 | 3.47637 | 2258 | 15.92% |
| 26.1 | 3.41137 | 1463 | 10.32% |
| 27.1 | 3.28258 | 3975 | 28.03% |
| 28.1 | 3.17265 | 2581 | 18.20% |
| 29.8 | 3.00049 | 2969 | 20.93% |

Figure 4:
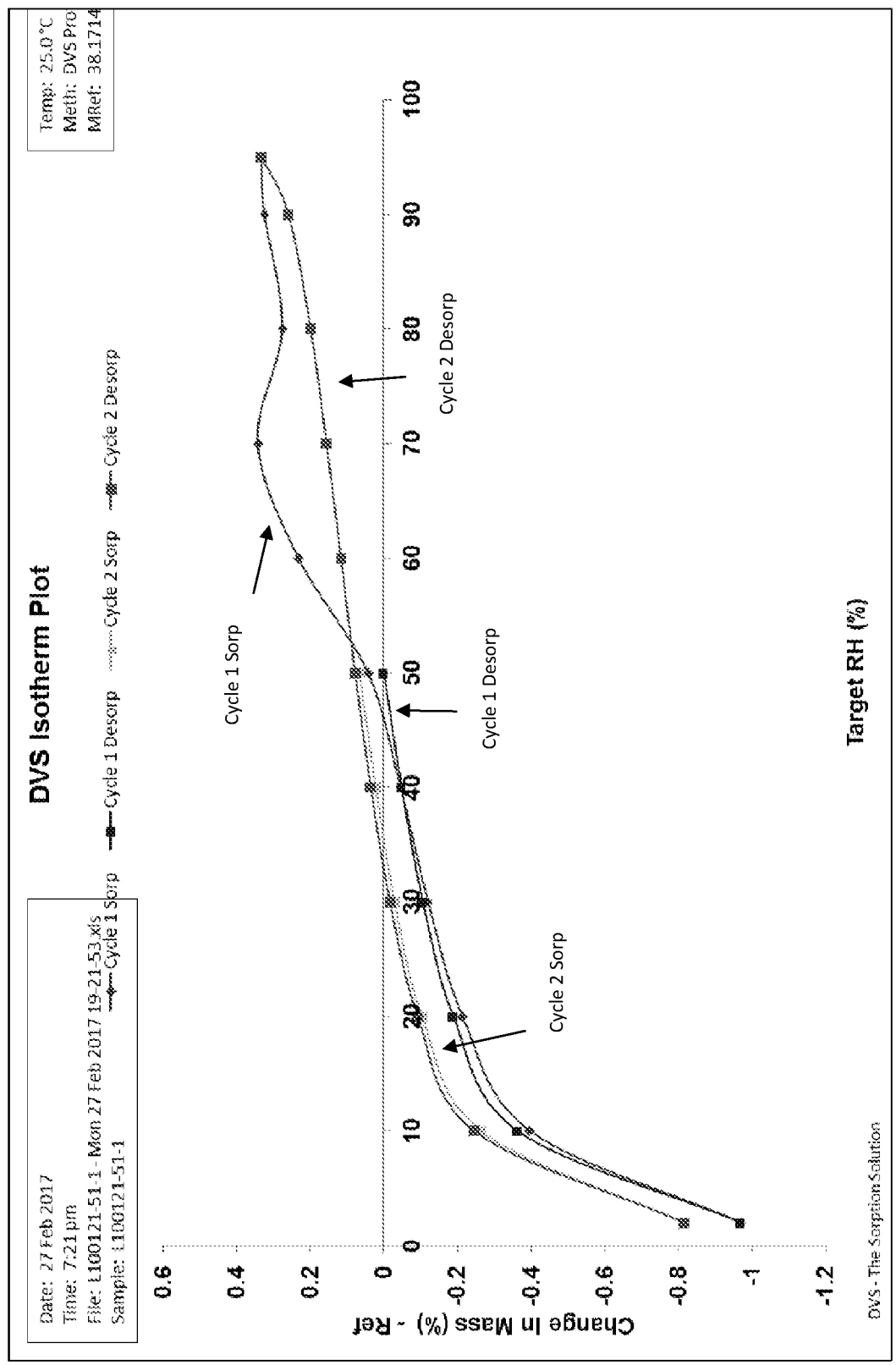
FIG. 4 depicts the dynamic vapor sorption (DVS) isotherm for crystalline hemisulfate salt Form A.
Figure 5I:
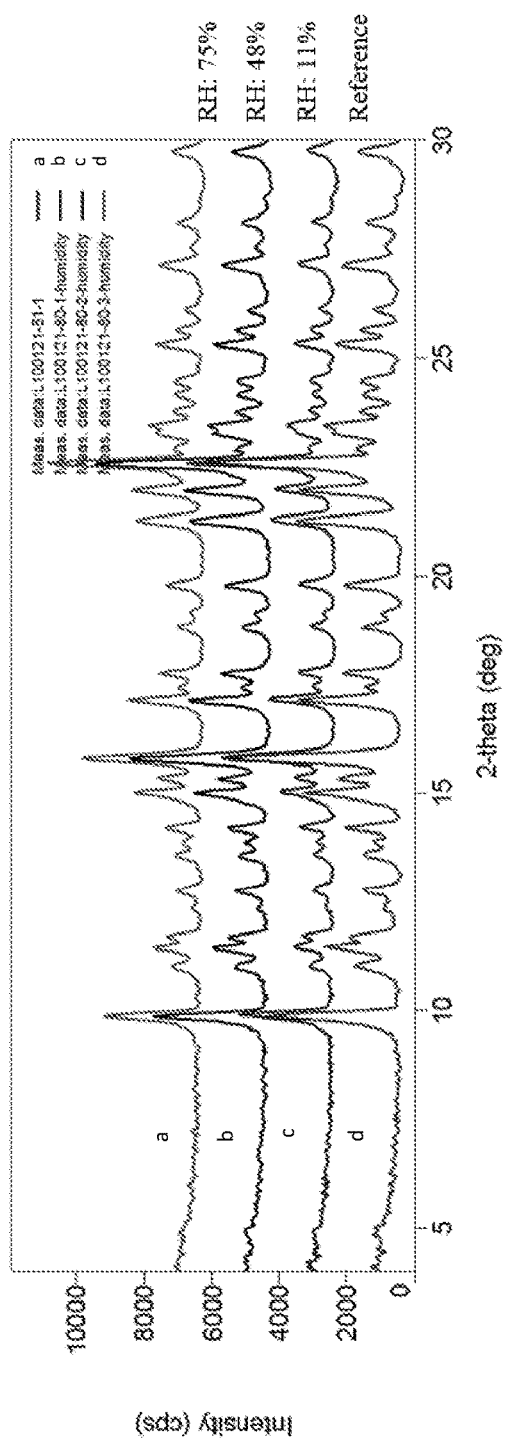
FIG. 5 (*i*) depicts X-ray powder diffraction pattern (XRPD) overlay for crystalline hemisulfate salt Form A and after exposure to 11%, 48%, and 75% relative humidity and 40° C. for two weeks. The XRPD remained unchanged after two-week test under these three humidity conditions.
Figure 5:
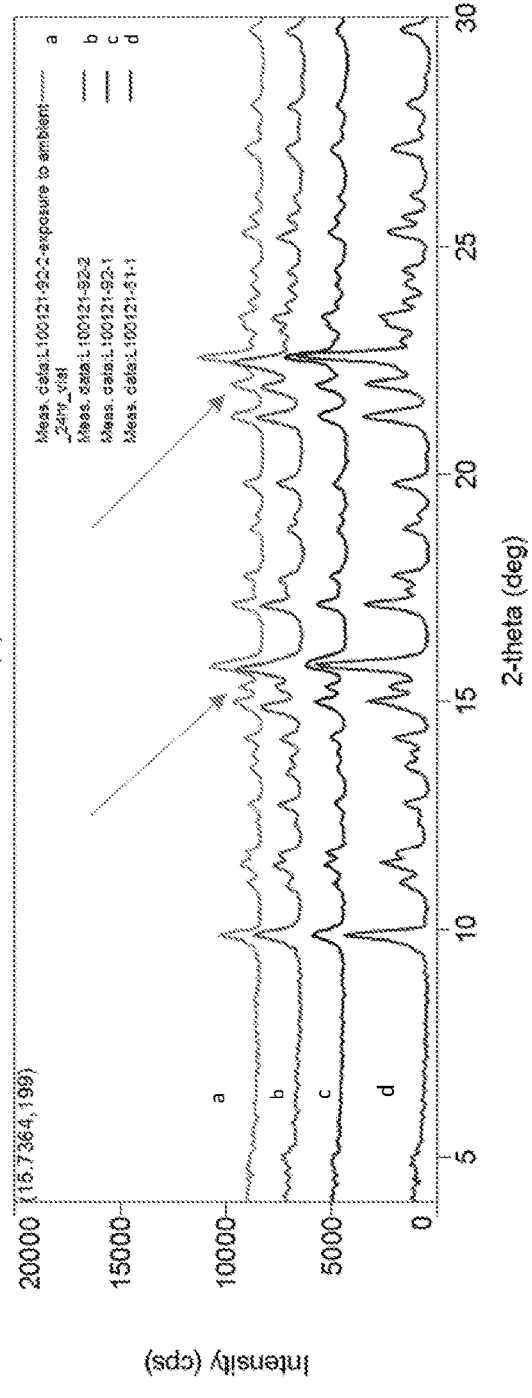

TGA of Form A showed about 4.5% weight loss up to 180° C. See FIG. 2. The water content by Karl Fisher was about 5.3%. Two thermal events were observed in DSC thermogram with the first peak at 159.9° C. and the second peak at 199.1° C. See FIG. 3. The first peak also showed a shoulder. Dynamic vapor sorption of salt Form A at 25° C. showed that the solid picks up about 1.3% moisture from 2% to 95% relative humidity. See FIG. 4. The DVS showed a rapid weight loss at humidity of less than 10% which was reversible upon sorption cycle. A DVS isotherm taken at 40° C. was essentially the same as the one at 25° C. The XRPD remained unchanged after DVS at both temperatures. Humidity test was conducted on Form A with exposure to 11%, 48%, and 75% relative humidity at 40° C. for 2 weeks followed by XRPD analysis. The XRPD remained unchanged after two week test. See FIG. 5. Crystallographic data for Form A is as follows:

Empirical formula: $C_{48}H_6N_8O_{13}S_3$
Formula weight: 1053.22
Temperature: 173(2) K
Wavelength: 1.54178 Å
Crystal system, space group: Monoclinic, C 2/c
Unit cell dimensions:
a=3.0748(5) Å
b=10.2638(4) Å
c=36.1371(12) Å
α=90 deg.
β=97.340(3) deg.
γ=90 deg.
Volume: 4809.8(3) Å$^3$
Z=4
Calculated density: 1.454 Mg/m$^3$
Absorption coefficient: 2.046 mm$^{-1}$
F(000): 2224
Crystal size: 0.171×0.156×0.061 mm$^3$
Theta range for data collection: 2.47 to 72.03°. deg.

Limiting indices:
 −15≤h≤16
 −12≤k≤12
 −43≤l≤44
Reflections collected/unique: 16676/4532 [R(int)=0.0767] Completeness: 95.6%
Refinement method: Full-matrix least-squares on $F^2$
Data/restraints/parameters: 4532/0/336
Goodness-of-fit on $F^2$: 1.096 ii). Form B

Figure 6:
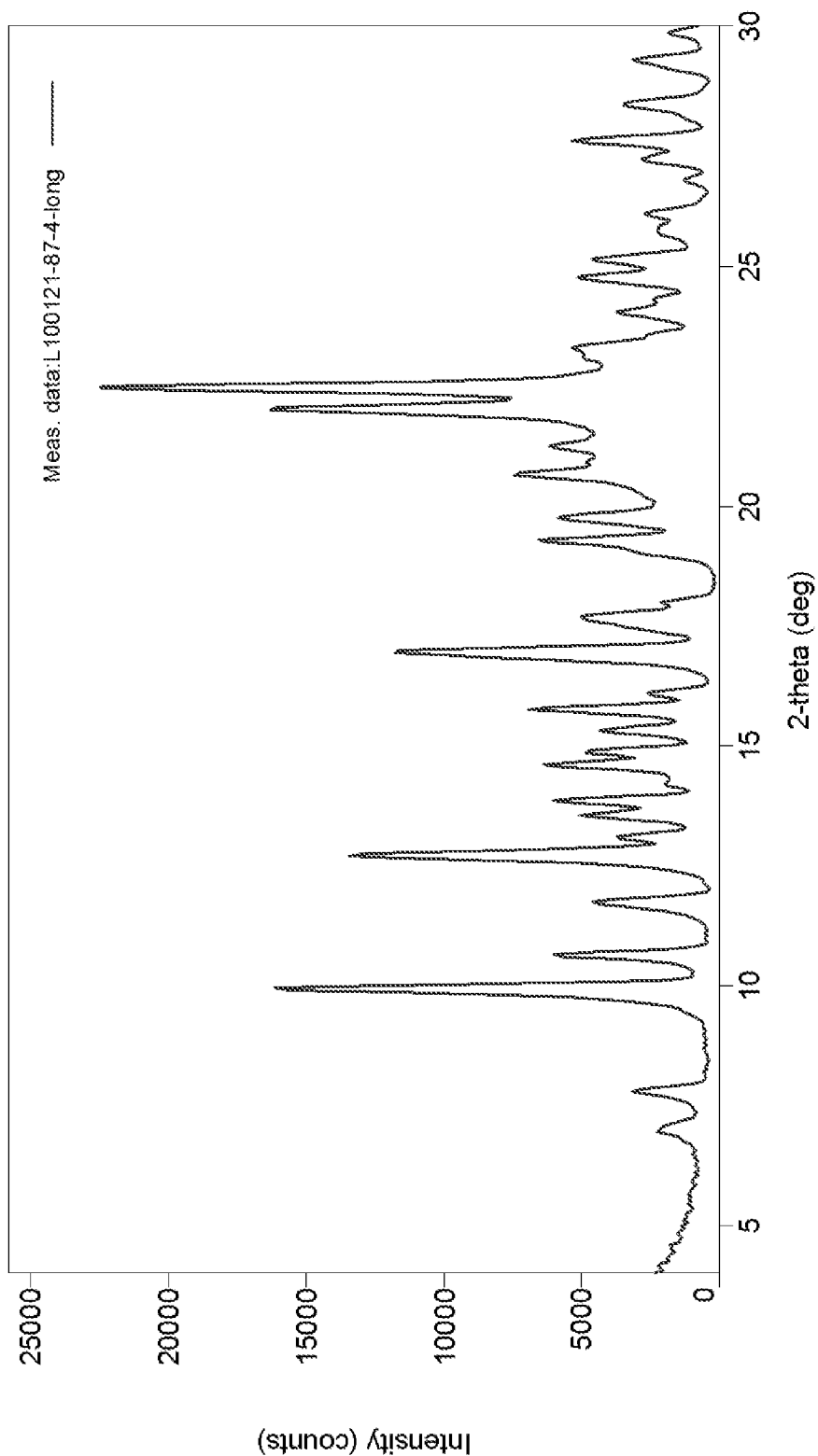
FIG. 6 depicts an X-ray powder diffraction pattern (XRPD) for crystalline hemisulfate salt Form B obtained in MeOH:EtOH (3:7).
Figure 7I:
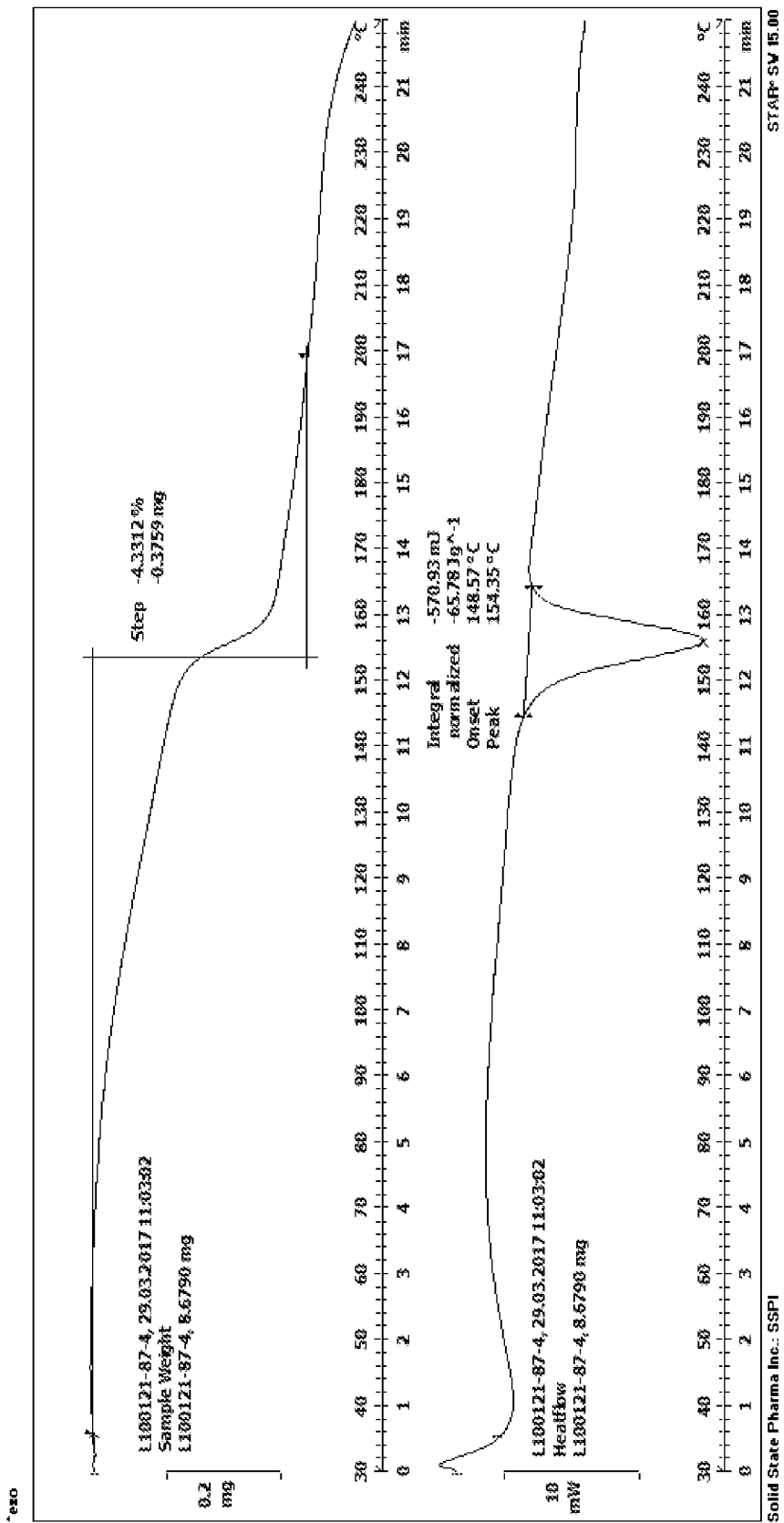
FIG. 7(*i*) depicts the combined thermogravimetric analysis (TGA) thermogram and differential scanning calorimetry (DSC) thermogram for crystalline hemisulfate salt Form B.
Figure 7I:
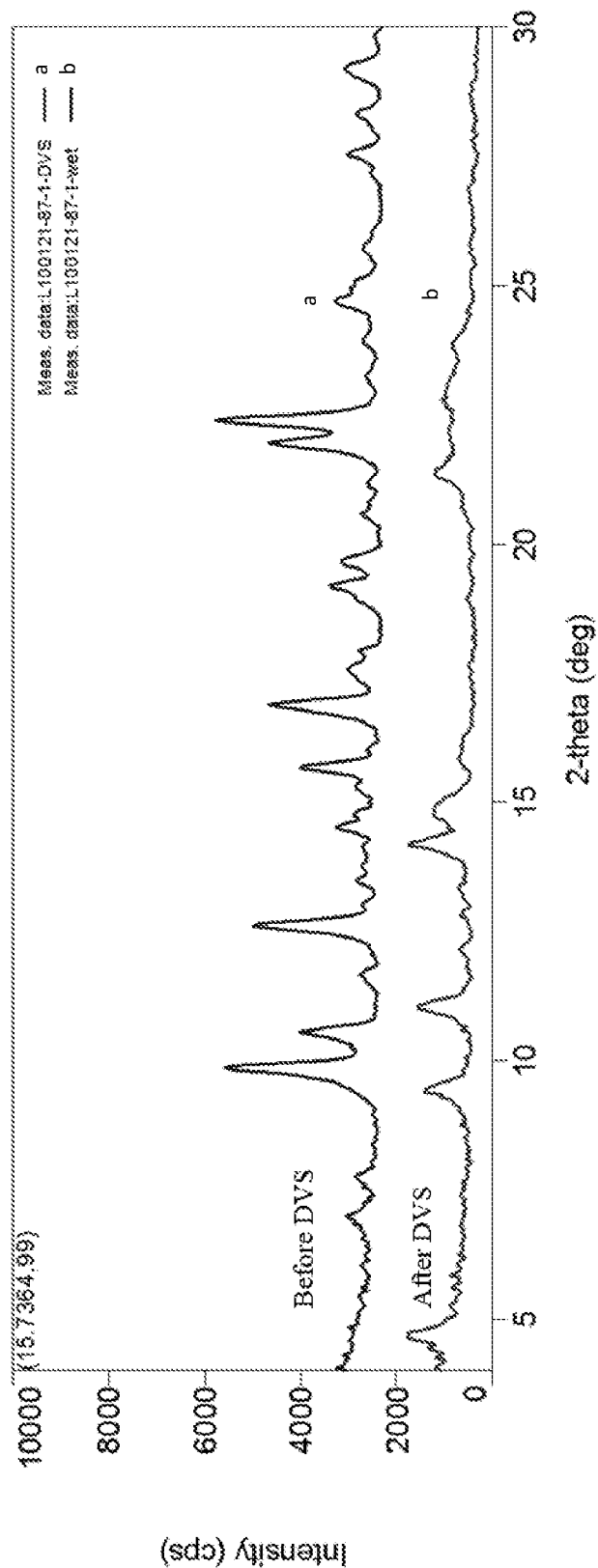

The XRPD for Form B is shown by FIG. 6 and the peak listings are shown in Table 24.

TABLE 24

| Angle, 2-θ | d spacing (A°) | Height (counts) | Rel. Int. |
|---|---|---|---|
| 7.0 | 12.57535 | 1083 | 8.57% |
| 7.8 | 11.27583 | 1748 | 13.83% |
| 9.9 | 8.89921 | 10912 | 86.36% |
| 10.6 | 8.33283 | 3619 | 28.64% |
| 11.7 | 7.55341 | 2313 | 18.31% |
| 12.7 | 6.95632 | 7739 | 61.25% |
| 13.1 | 6.7694 | 1609 | 12.73% |
| 13.5 | 6.53423 | 2490 | 19.71% |
| 13.9 | 6.38636 | 3216 | 25.45% |
| 14.6 | 6.06413 | 3446 | 27.27% |
| 14.9 | 5.94981 | 2751 | 21.77% |
| 15.3 | 5.79313 | 2471 | 19.56% |
| 15.7 | 5.62485 | 4393 | 34.77% |
| 16.1 | 5.51086 | 1536 | 12.16% |
| 16.9 | 5.2332 | 7462 | 59.06% |
| 17.6 | 5.02985 | 2722 | 21.54% |
| 19.3 | 4.60381 | 2787 | 22.06% |
| 19.7 | 4.50087 | 2503 | 19.81% |
| 20.7 | 4.29561 | 2454 | 19.42% |
| 21.2 | 4.18049 | 1540 | 12.19% |
| 22.0 | 4.03572 | 8193 | 64.84% |
| 22.5 | 3.95619 | 12635 | 100.00% |
| 23.3 | 3.81776 | 1530 | 12.11% |
| 24.0 | 3.70488 | 985 | 7.80% |
| 24.7 | 3.60111 | 2053 | 16.25% |
| 25.1 | 3.54205 | 2015 | 15.95% |
| 25.7 | 3.46451 | 521 | 4.12% |
| 26.1 | 3.41725 | 1020 | 8.07% |
| 27.2 | 3.27757 | 1417 | 11.21% |
| 27.6 | 3.23088 | 3271 | 25.89% |
| 28.4 | 3.1406 | 1887 | 14.93% |
| 29.3 | 3.04578 | 1720 | 13.61% |
| 29.8 | 2.99111 | 750 | 5.94% |

Form B tends to hold substantial amount of solvent. However, the TGA data did not correspond to the NMR data for organic solvent, which could be due to hygroscopic nature of Form B. See e.g., FIG. 7. The DVS of Form B showed the solid picks up about 14% moisture between 2% and 95% relative humidity.

iv). Form D

Figure 9:
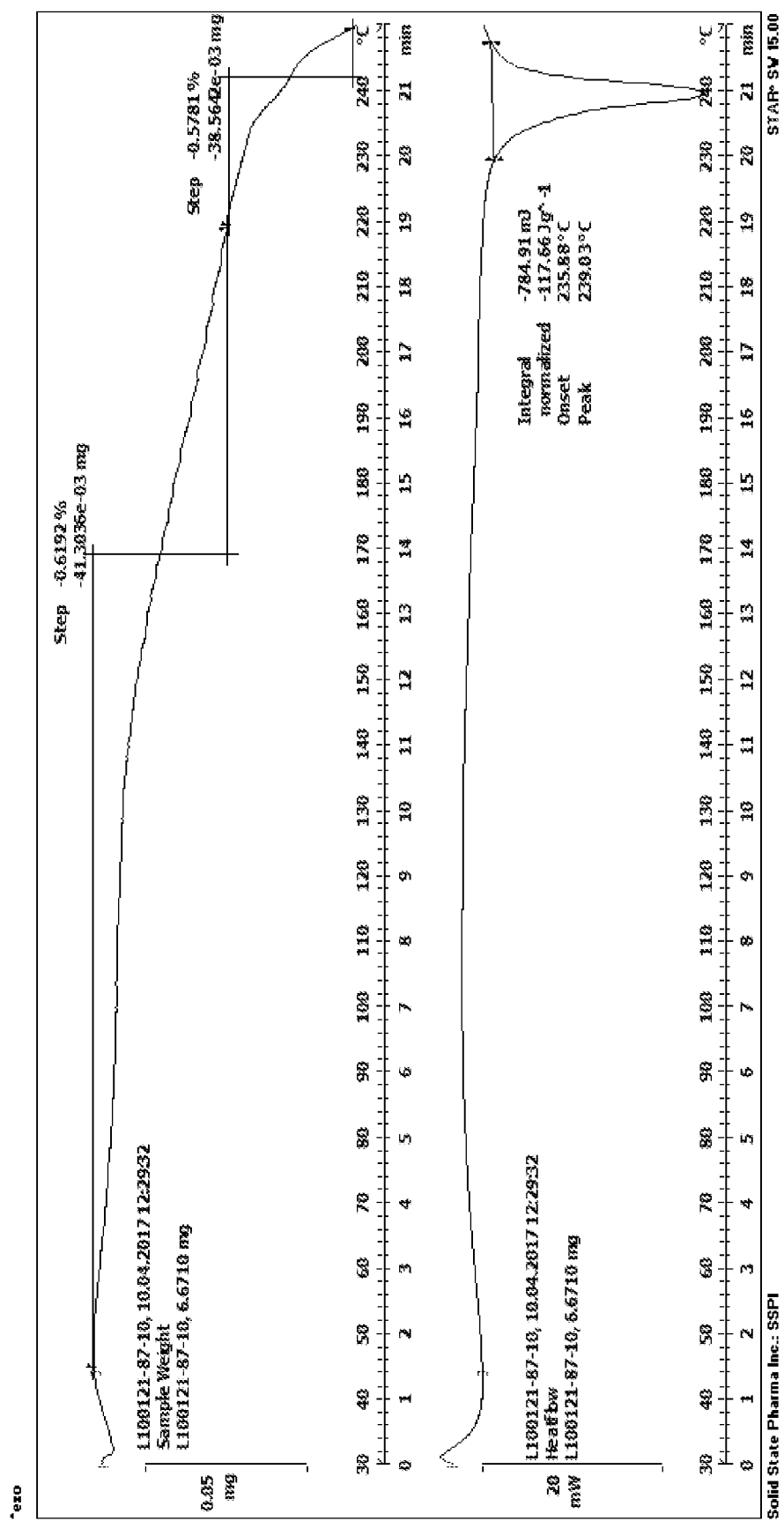
FIG. 9 depicts the thermogravimetric analysis (TGA) thermogram and differential scanning calorimetry (DSC) thermogram for crystalline hemisulfate salt Form D.

The XRPD for Form D is shown by FIG. 9 and the peak listings are shown in Table 26.

TABLE 26

| Angle, 2-θ | d spacing (A°) | Height (counts) | Rel. Int. |
|---|---|---|---|
| 5.8 | 15.28058 | 4971 | 70.74% |
| 10.0 | 8.87509 | 4389 | 62.46% |
| 10.2 | 8.65751 | 6043 | 86.00% |
| 11.3 | 7.82263 | 2566 | 36.52% |
| 11.5 | 7.66971 | 749 | 10.66% |
| 12.2 | 7.27684 | 3233 | 46.01% |
| 13.6 | 6.51388 | 2448 | 34.84% |
| 14.1 | 6.28225 | 1365 | 19.43% |

TABLE 26-continued

| Angle, 2-θ | d spacing (A°) | Height (counts) | Rel. Int. |
|---|---|---|---|
| 14.7 | 6.01924 | 2881 | 41.00% |
| 15.4 | 5.74733 | 250 | 3.56% |
| 16.0 | 5.52579 | 1652 | 23.51% |
| 17.3 | 5.13037 | 3250 | 46.25% |
| 17.6 | 5.03792 | 3136 | 44.63% |
| 19.3 | 4.59918 | 5083 | 72.34% |
| 20.0 | 4.42807 | 1495 | 21.28% |
| 20.8 | 4.26377 | 1928 | 27.44% |
| 22.1 | 4.01598 | 1363 | 19.40% |
| 22.9 | 3.88059 | 4961 | 70.60% |
| 23.3 | 3.81849 | 7027 | 100.00% |
| 23.6 | 3.76707 | 3176 | 45.20% |
| 24.4 | 3.6518 | 1755 | 24.98% |
| 25.2 | 3.52644 | 4136 | 58.86% |
| 26.4 | 3.37296 | 1305 | 18.57% |
| 27.4 | 3.25211 | 610 | 8.68% |
| 28.3 | 3.15078 | 553 | 7.87% |
| 29.6 | 3.01482 | 615 | 8.75% |

Figure 10:
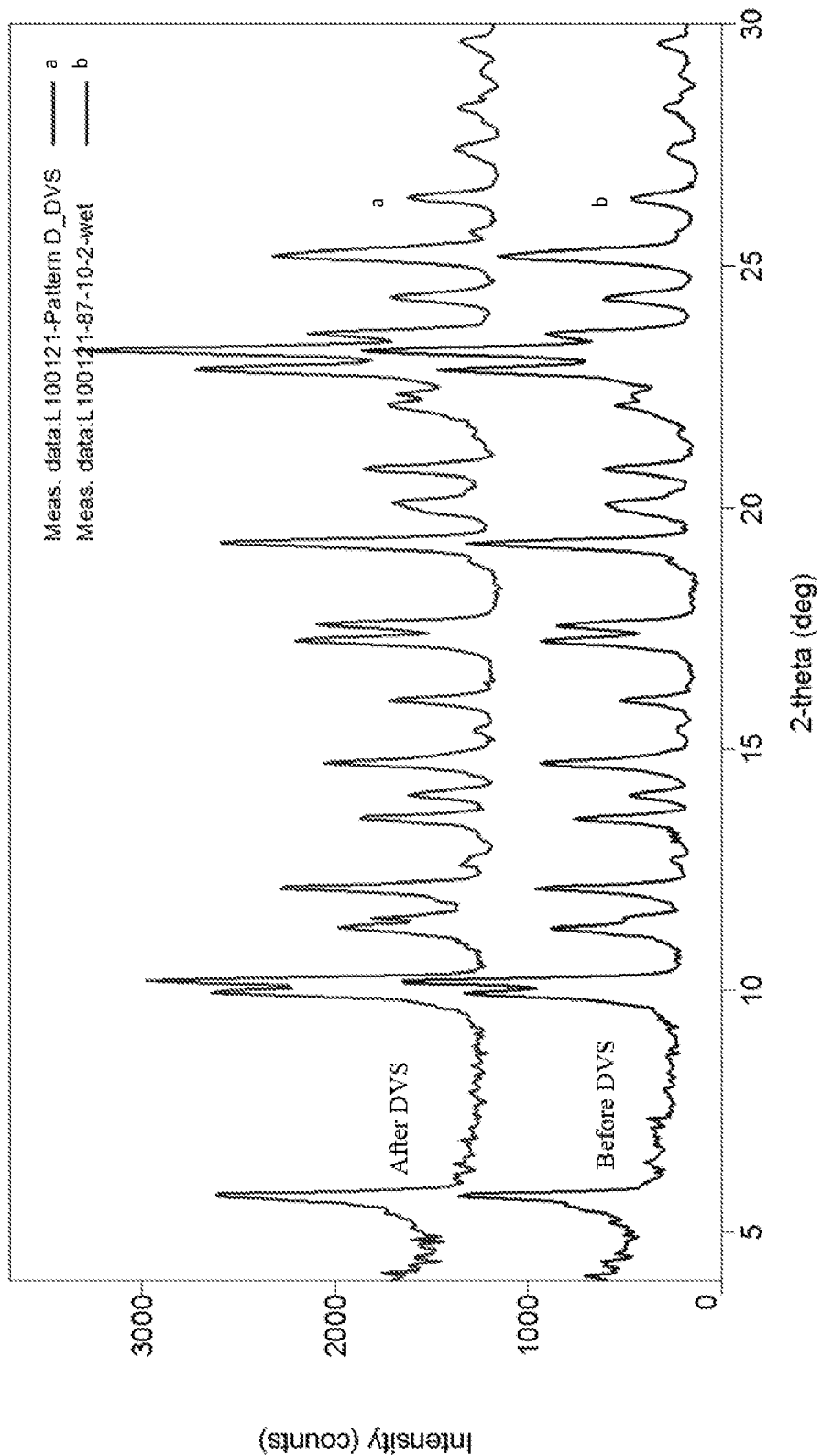
FIG. 10 depicts the X-ray powder diffraction pattern (XRPD) for crystalline hemisulfate salt Form D before and after dynamic vapor sorption (DVS).

Form D was determined to be anhydrous with a melting peak at 239° C. See e.g., FIG. 9. DVS of Pattern D was performed and solid picked up about 2% moisture from 2% to 95% relative humidity. See FIG. 10. The XRPD pattern remained unchanged after DVS and one week exposure to 75% relative humidity at 40° C. also did not change the form.

v). Form E

Figure 11:
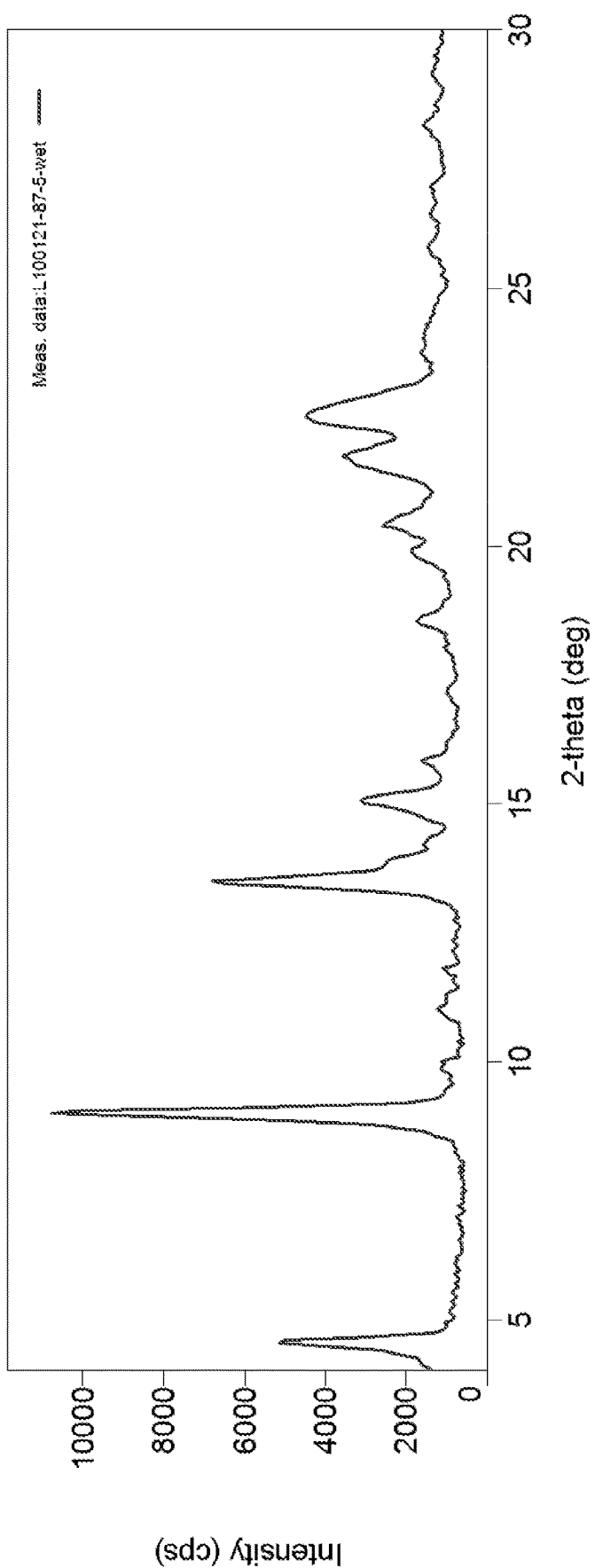
FIG. 11 depicts an X-ray powder diffraction pattern (XRPD) for crystalline hemisulfate salt Form E.

The XRPD for Form E is shown by FIG. 11 and the peak listings are shown in Table 27.

TABLE 27

| Angle, 2-θ | d spacing (A°) | Height (counts) | Rel. Int. |
|---|---|---|---|
| 4.6 | 19.33569 | 1738.68 | 42.25% |
| 9.0 | 9.8034 | 4115.26 | 100.00% |
| 9.9 | 8.90634 | 170.17 | 4.14% |
| 11.0 | 8.05091 | 182.67 | 4.44% |
| 13.5 | 6.56847 | 2221.93 | 53.99% |
| 15.1 | 5.86939 | 909.83 | 22.11% |
| 15.8 | 5.59154 | 280.55 | 6.82% |
| 18.5 | 4.78855 | 309.99 | 7.53% |
| 19.8 | 4.48316 | 260.12 | 6.32% |
| 20.4 | 4.34963 | 461.71 | 11.22% |
| 21.7 | 4.09107 | 862.85 | 20.97% |
| 22.5 | 3.94718 | 1259.97 | 30.62% |
| 28.1 | 3.1714 | 143.14 | 3.48% | vi). Form F

Figure 12:
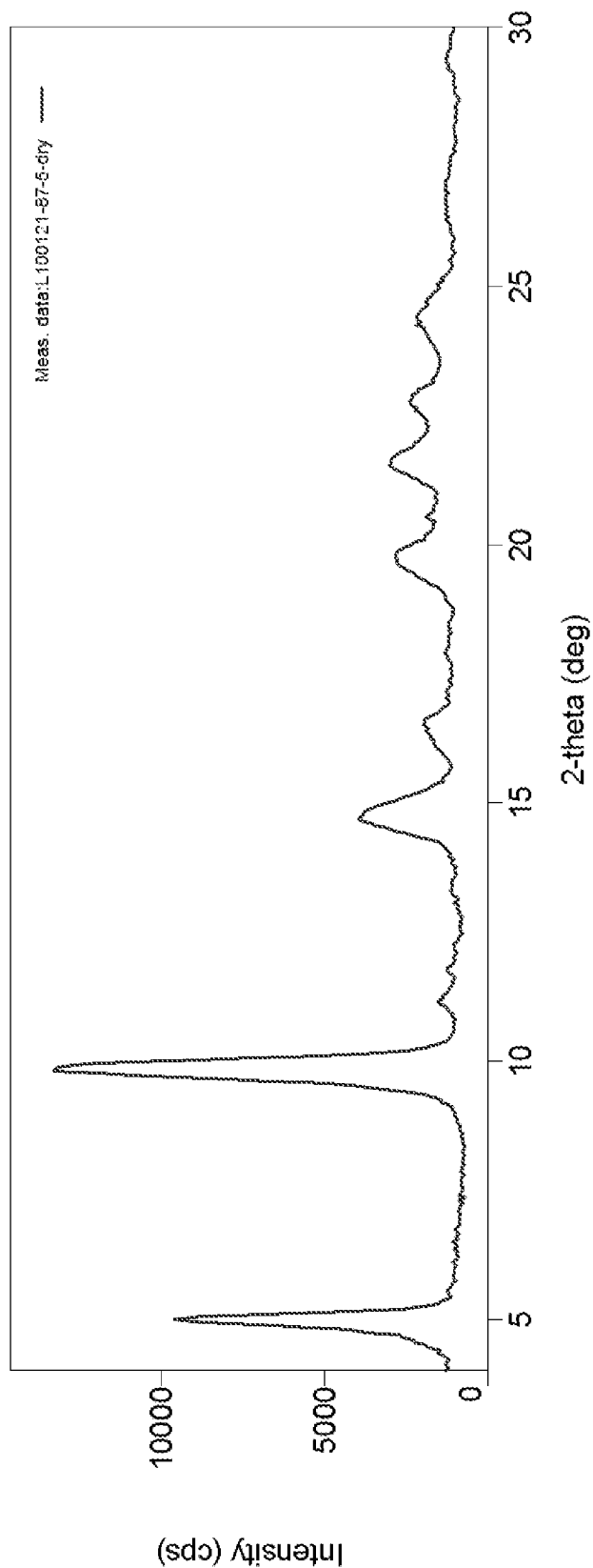
FIG. 12 depicts an X-ray powder diffraction pattern (XRPD) for crystalline hemisulfate salt Form F.
Figure 13:
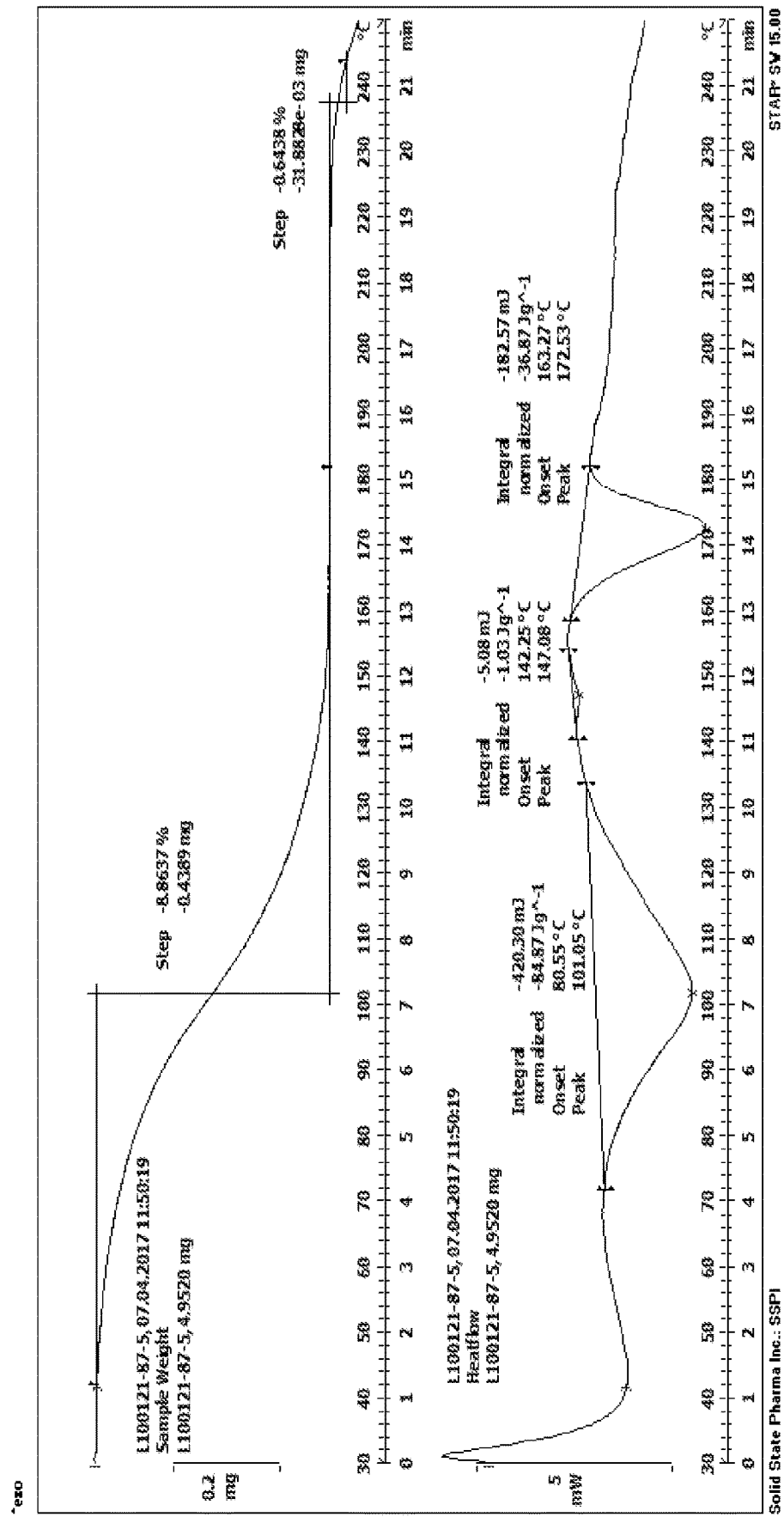
FIG. 13 depicts the thermogravimetric analysis (TGA) thermogram and differential scanning calorimetry (DSC) thermogram for crystalline hemisulfate salt Form F.

The XRPD for Form F is shown by FIG. 12 and the peak listings are shown in Table 28. A combined TGA and DSC is shown by FIG. 13.

TABLE 28

| Angle, 2-θ | d spacing (A°) | Height (counts) | Rel. Int. |
|---|---|---|---|
| 5.0 | 17.63127 | 3501.15 | 68.88% |
| 9.9 | 8.953 | 5083.17 | 100.00% |
| 11.1 | 7.95783 | 175.54 | 3.45% |
| 14.7 | 6.02129 | 1144.71 | 22.52% |
| 16.5 | 5.3774 | 319.64 | 6.29% |
| 19.6 | 4.52559 | 557.84 | 10.97% |

TABLE 28-continued

| Angle, 2-θ | d spacing (A°) | Height (counts) | Rel. Int. |
|---|---|---|---|
| 21.6 | 4.11341 | 625.78 | 12.31% |
| 22.8 | 3.89996 | 383.12 | 7.54% |
| 24.4 | 3.64257 | 313.08 | 6.16% | vii). Form G

Figure 14:
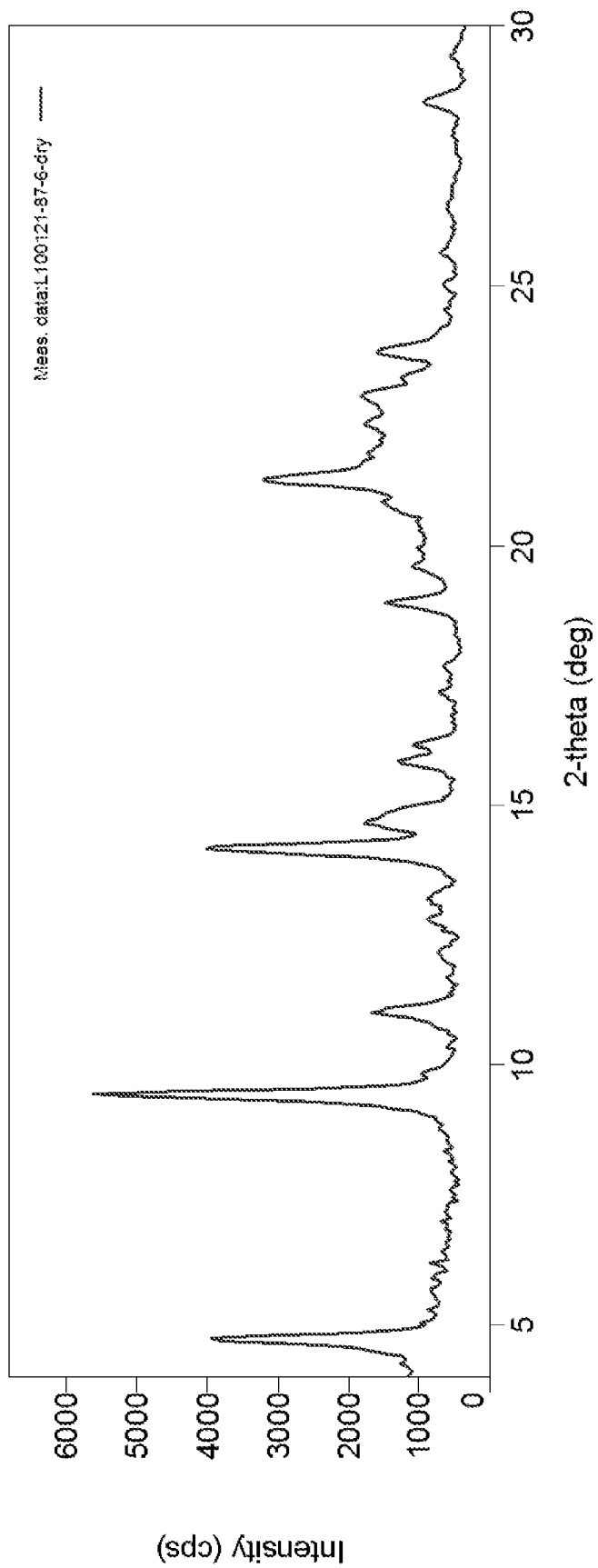
FIG. 14 depicts an X-ray powder diffraction pattern (XRPD) for crystalline hemisulfate salt Form G.
Figure 15:
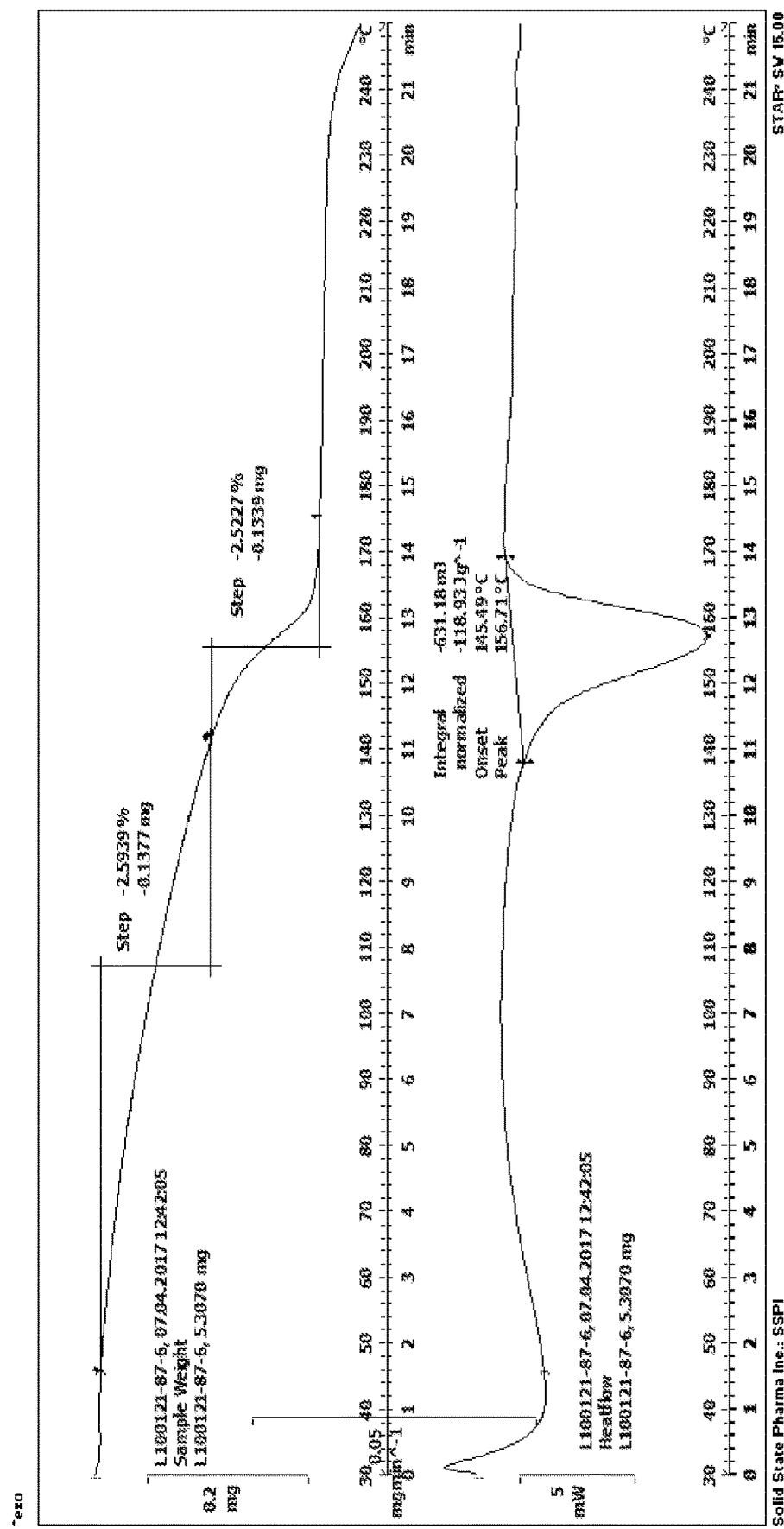
FIG. 15 depicts the thermogravimetric analysis (TGA) thermogram and differential scanning calorimetry (DSC) thermogram for crystalline hemisulfate salt Form G.

The XRPD for Form G is shown by FIG. 14 and the peak listings are shown in Table 29. A combined TGA and DSC is shown by FIG. 15.

TABLE 29

| Angle, 2-θ | d spacing (A°) | Height (counts) | Rel. Int. |
|---|---|---|---|
| 4.7 | 18.70556 | 1242.62 | 59.33% |
| 9.4 | 9.36302 | 2094.33 | 100.00% |
| 11.0 | 8.02324 | 393.11 | 18.77% |
| 13.3 | 6.67148 | 95.37 | 4.55% |
| 14.1 | 6.2664 | 1061.57 | 50.69% |
| 15.9 | 5.58681 | 287.25 | 13.72% |
| 16.2 | 5.46454 | 135.26 | 6.46% |
| 18.9 | 4.69155 | 302.27 | 14.43% |
| 21.1 | 4.20095 | 210.62 | 10.06% |
| 21.2 | 4.17959 | 623.95 | 29.79% |
| 22.8 | 3.89083 | 287.75 | 13.74% |
| 23.8 | 3.74261 | 339.41 | 16.21% |
| 26.7 | 3.3332 | 36.96 | 1.76% |
| 28.5 | 3.12882 | 200.93 | 9.59% | viii). Form H

Figure 16:
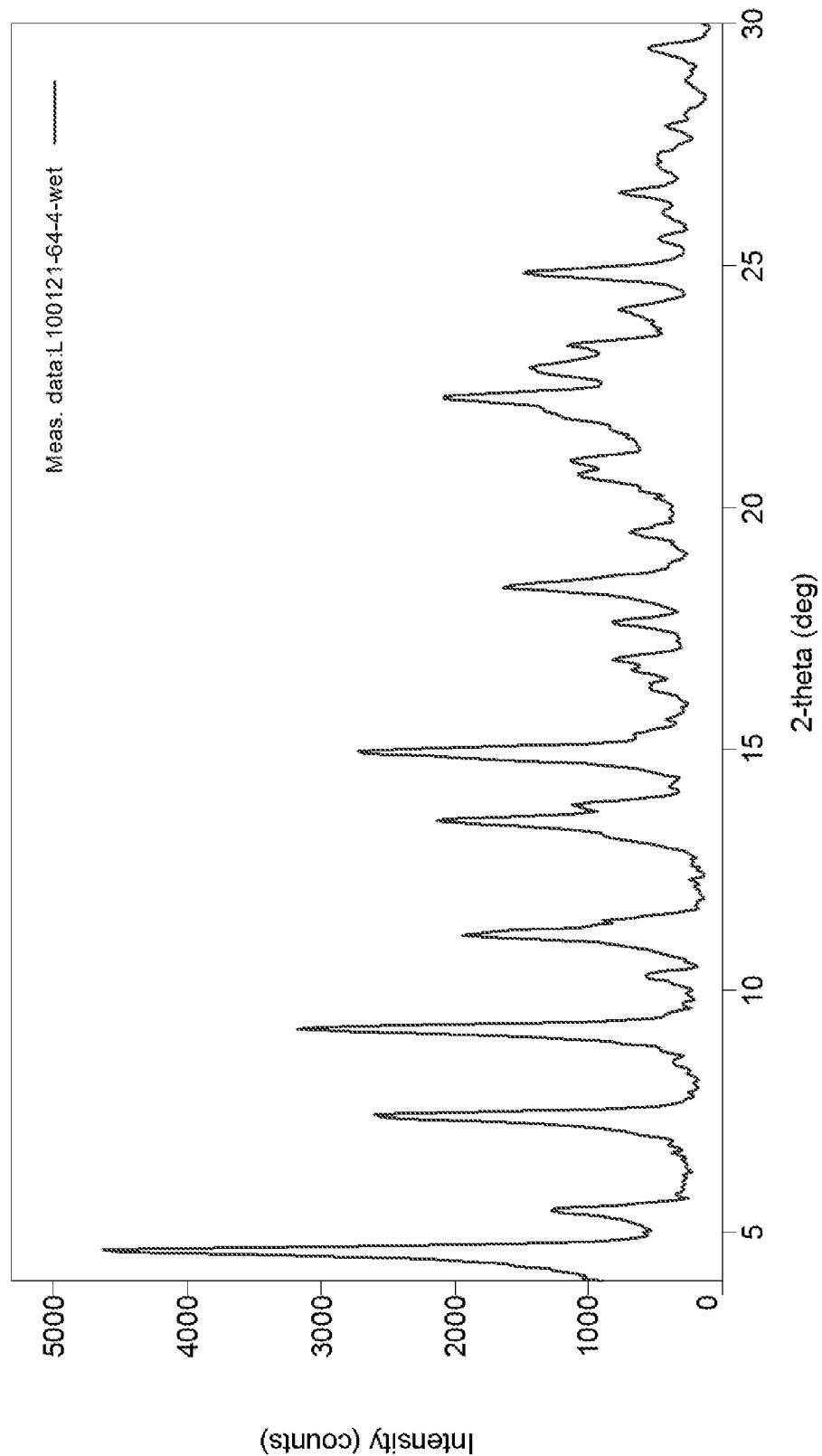
FIG. 16 depicts an X-ray powder diffraction pattern (XRPD) for crystalline hemisulfate salt Form H.

The XRPD for Form H is shown by FIG. 16 and the peak listings are shown in Table 30.

TABLE 30

| Angle, 2-θ | d spacing (A°) | Height (counts) | Rel. Int. |
|---|---|---|---|
| 4.6 | 19.00577 | 2892.58 | 100.00% |
| 5.4 | 16.21955 | 656.39 | 22.69% |
| 7.4 | 11.92606 | 1637.2 | 56.60% |
| 9.2 | 9.58199 | 2031.32 | 70.23% |
| 10.3 | 8.60629 | 244.93 | 8.47% |
| 11.1 | 7.96834 | 1041.86 | 36.02% |
| 13.5 | 6.53326 | 1064.3 | 36.79% |
| 13.8 | 6.3908 | 495.71 | 17.14% |
| 14.9 | 5.92137 | 1640.91 | 56.73% |
| 16.9 | 5.24557 | 238.8 | 8.26% |
| 17.6 | 5.03079 | 330.16 | 11.41% |
| 18.4 | 4.82818 | 764.47 | 26.43% |
| 19.5 | 4.55426 | 201.62 | 6.97% |
| 20.7 | 4.28199 | 421.57 | 14.57% |
| 22.3 | 3.98173 | 914.58 | 31.62% |
| 22.9 | 3.88793 | 641.59 | 22.18% |
| 23.4 | 3.80422 | 445.25 | 15.39% |
| 24.1 | 3.68517 | 219.37 | 7.58% |
| 24.8 | 3.58024 | 766.52 | 26.50% |
| 26.5 | 3.36223 | 292.29 | 10.10% |
| 27.2 | 3.27175 | 129.95 | 4.49% |
| 29.5 | 3.0237 | 272.48 | 9.42% | ix). Form I

Figure 17:
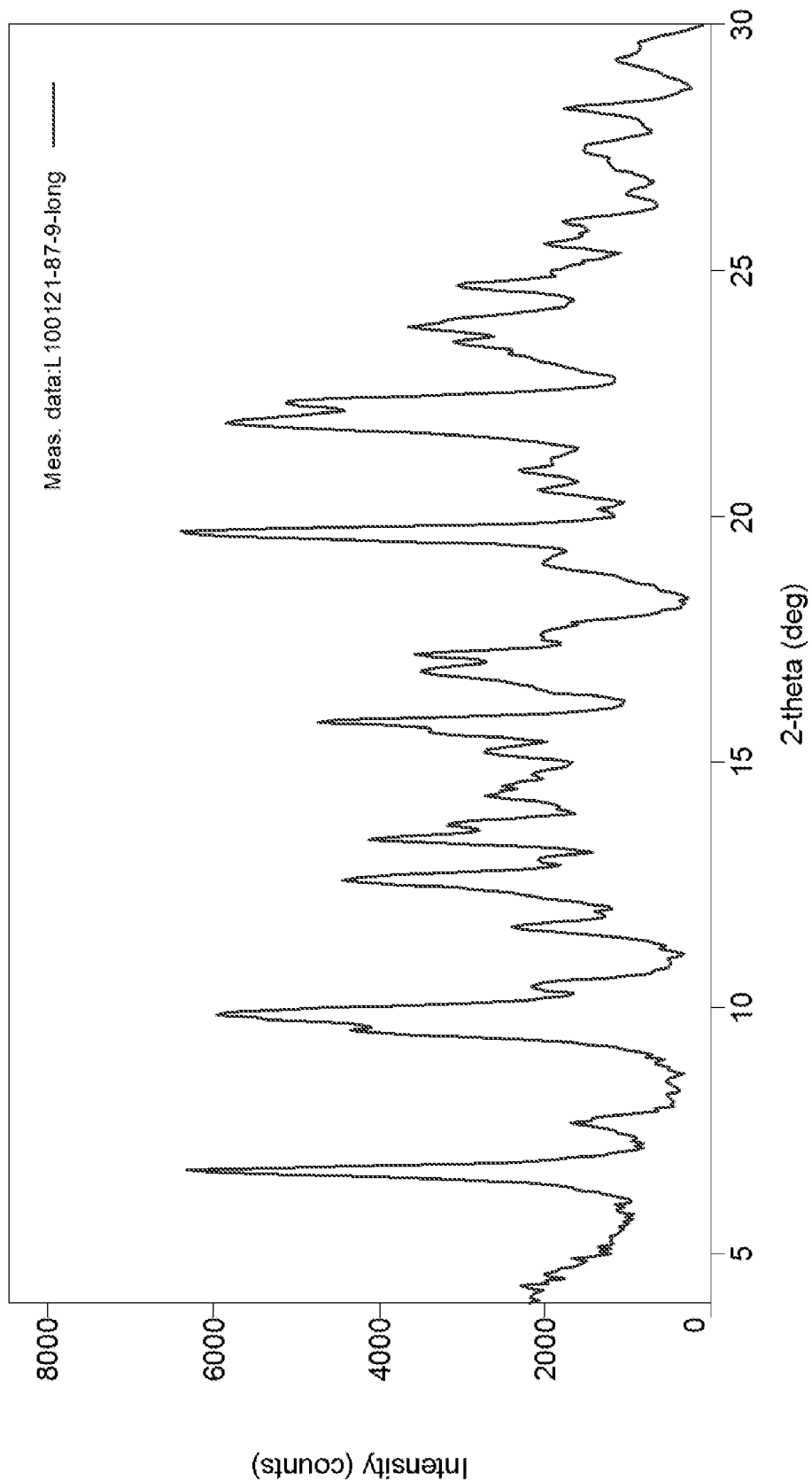
FIG. 17 depicts an X-ray powder diffraction pattern (XRPD) for crystalline hemisulfate salt Form I.
Figure 18:
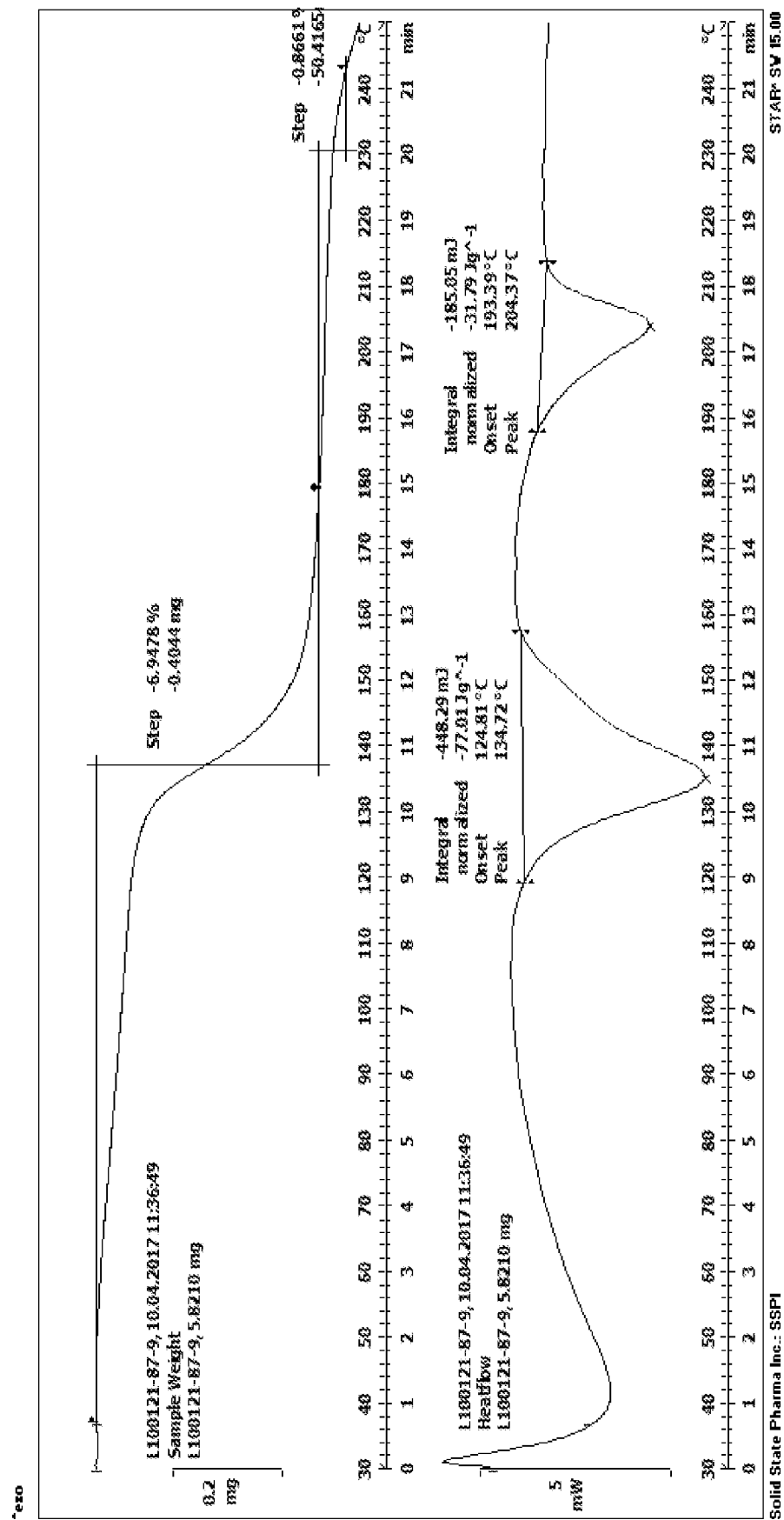
FIG. 18 depicts the thermogravimetric analysis (TGA) thermogram and differential scanning calorimetry (DSC) thermogram for crystalline hemisulfate salt Form I.

The XRPD for Form I is shown by FIG. 17 and the peak listings are shown in Table 31. A combined TGA and DSC is shown by FIG. 18. NMR analysis revealed the present of about 4.6% EtOH, indicating a possible solvate.

TABLE 31

| Angle, 2-θ | d spacing (A°) | Height (counts) | Rel. Int. |
|---|---|---|---|
| 6.7 | 13.16055 | 3581.49 | 96.93% |
| 7.7 | 11.44901 | 740.16 | 20.03% |
| 9.5 | 9.319 | 1710.55 | 46.29% |
| 9.9 | 8.97128 | 3519.19 | 95.24% |
| 10.5 | 8.45555 | 1052.24 | 28.48% |
| 11.6 | 7.61244 | 855.25 | 23.15% |
| 12.6 | 7.01279 | 1799.14 | 48.69% |
| 13.4 | 6.60237 | 1385.62 | 37.50% |
| 13.8 | 6.43395 | 850.03 | 23.00% |
| 14.3 | 6.19667 | 516.23 | 13.97% |
| 15.2 | 5.8277 | 722.04 | 19.54% |
| 15.8 | 5.59406 | 1926.11 | 52.13% |
| 16.8 | 5.26642 | 1316.92 | 35.64% |
| 17.2 | 5.1627 | 745.55 | 20.18% |
| 19.0 | 4.65907 | 716.28 | 19.39% |
| 19.7 | 4.50851 | 3694.98 | 100.00% |
| 20.5 | 4.32796 | 526.56 | 14.25% |
| 20.9 | 4.25526 | 540.88 | 14.64% |
| 21.9 | 4.05301 | 2830.08 | 76.59% |
| 22.3 | 3.97817 | 2205.69 | 59.69% |
| 23.9 | 3.71963 | 1226.09 | 33.18% |
| 24.6 | 3.61051 | 976.08 | 26.42% |
| 25.5 | 3.48946 | 531.17 | 14.38% |
| 26.0 | 3.42073 | 440.36 | 11.92% |
| 27.5 | 3.24167 | 511.68 | 13.85% |
| 28.3 | 3.15203 | 747.77 | 20.24% |
| 29.3 | 3.0427 | 455.27 | 12.32% | x). Form J

Figure 19:
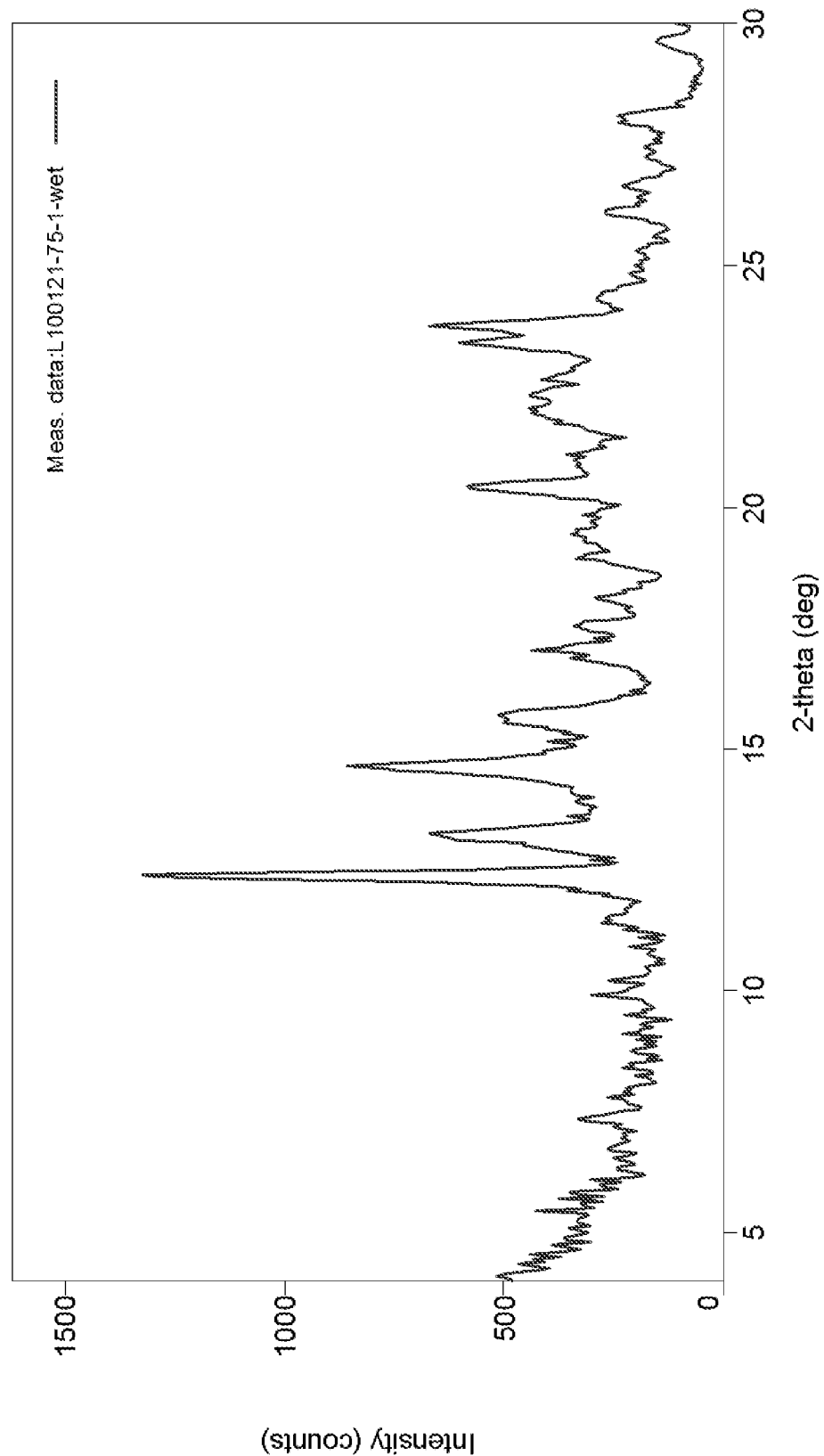
FIG. 19 depicts an X-ray powder diffraction pattern (XRPD) for crystalline hemisulfate salt Form J.
Figure 20:
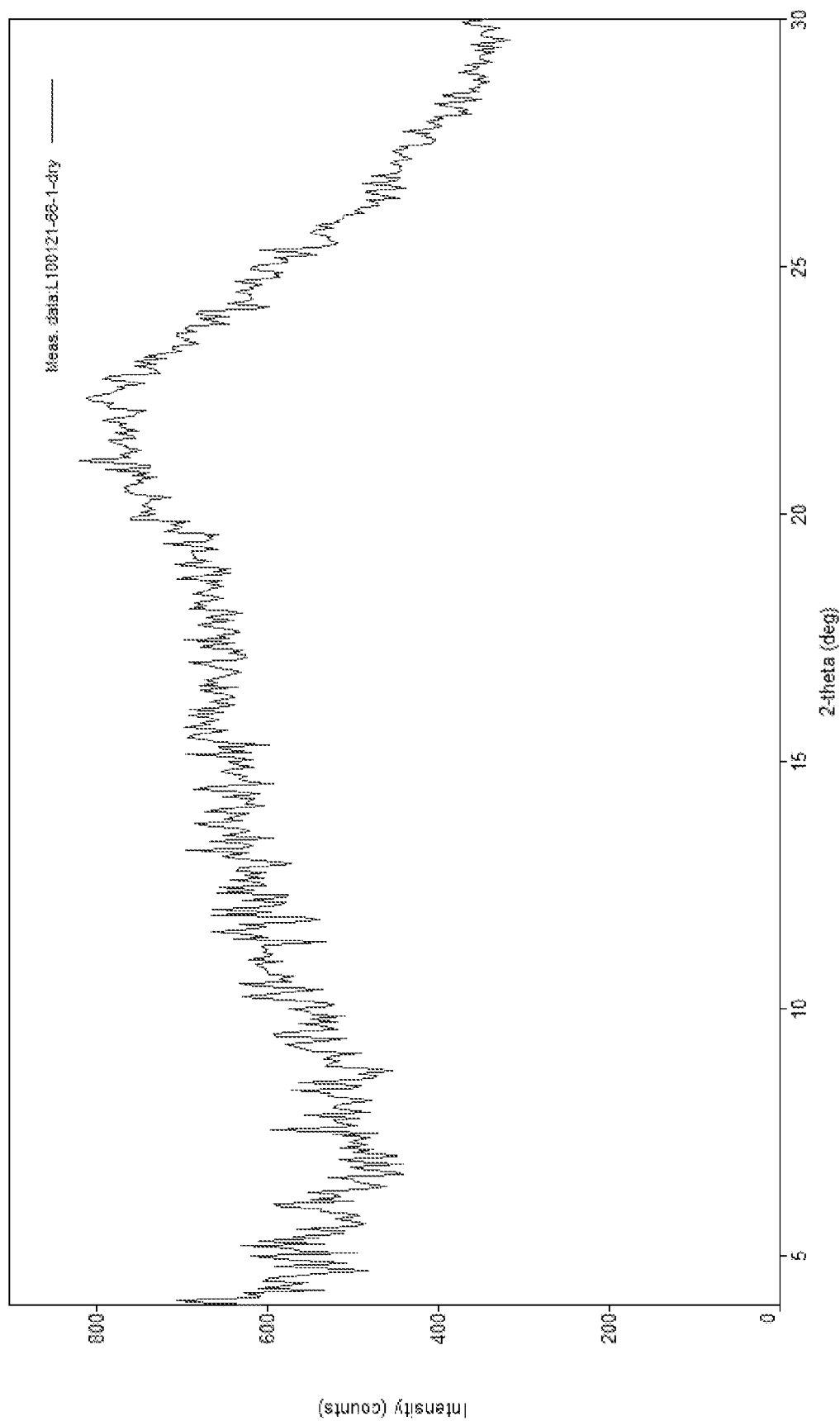
FIG. 20 depicts the X-ray powder diffraction pattern (XRPD) for amorphous hemisulfate salt form of Compound 1.
Figure 21:
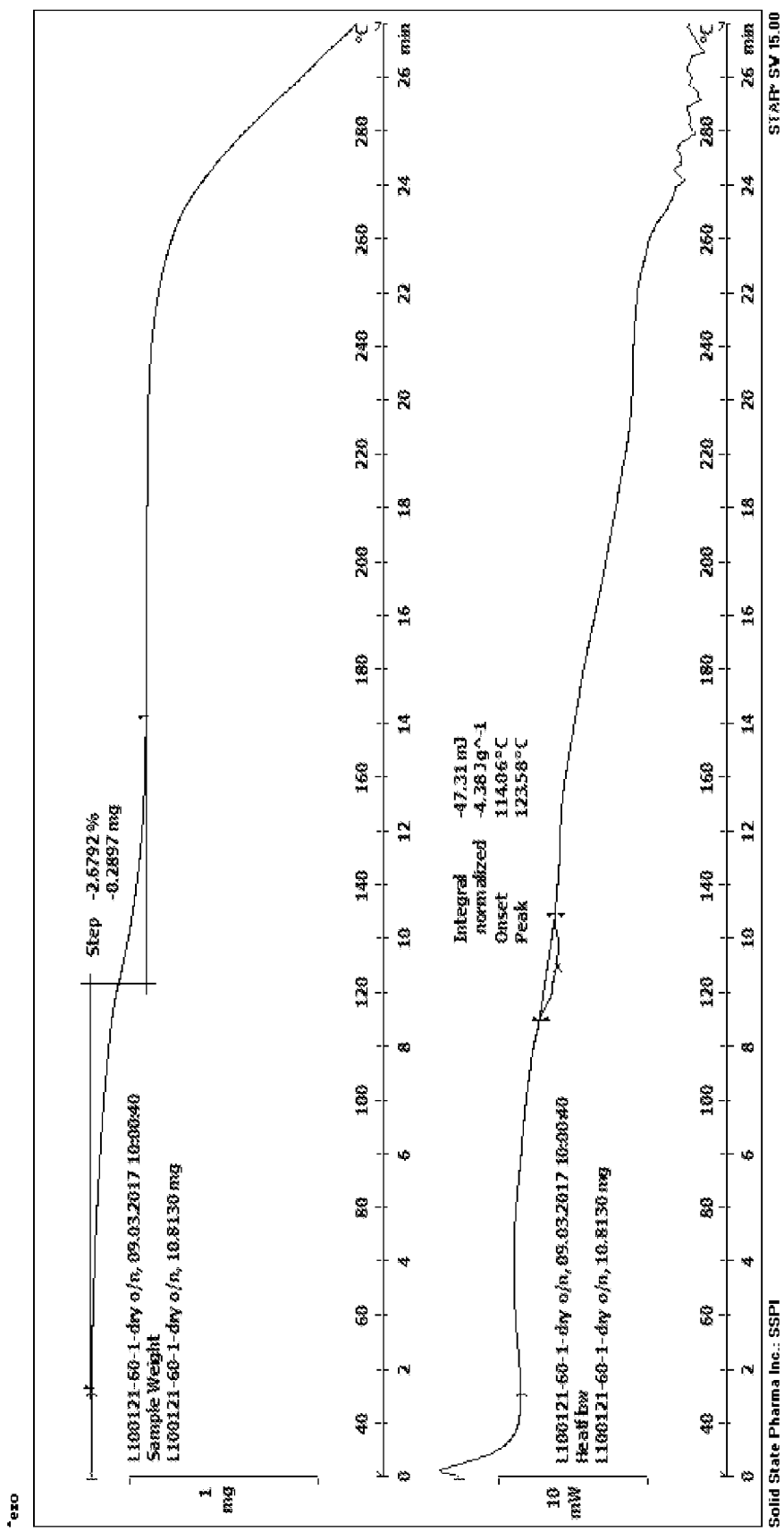
FIG. 21 depicts the thermogravimetric analysis (TGA) thermogram and differential scanning calorimetry (DSC) thermogram for amorphous hemisulfate salt of Compound 1 dried in vacuum oven at 50° C. for overnight.

The XRPD for Form J is shown by FIG. 19 and the peak listings are shown in Table 32.

TABLE 32

| Angle, 2-θ | d spacing (A°) | Height (counts) | Rel. Int. |
|---|---|---|---|
| 12.4 | 7.14209 | 722.37 | 100.00% |
| 13.2 | 6.69075 | 254.54 | 35.24% |
| 14.6 | 6.06522 | 348.12 | 48.19% |
| 15.7 | 5.64077 | 168.89 | 23.38% |
| 20.4 | 4.34313 | 213.59 | 29.57% |
| 22.0 | 4.0429 | 79.01 | 10.94% |
| 23.3 | 3.8076 | 179.4 | 24.83% |
| 23.7 | 3.74601 | 213.97 | 29.62% |
| 28.0 | 3.18475 | 87.25 | 12.08% | xi). Crystalline Free Base of Compound 1

Figure 25:
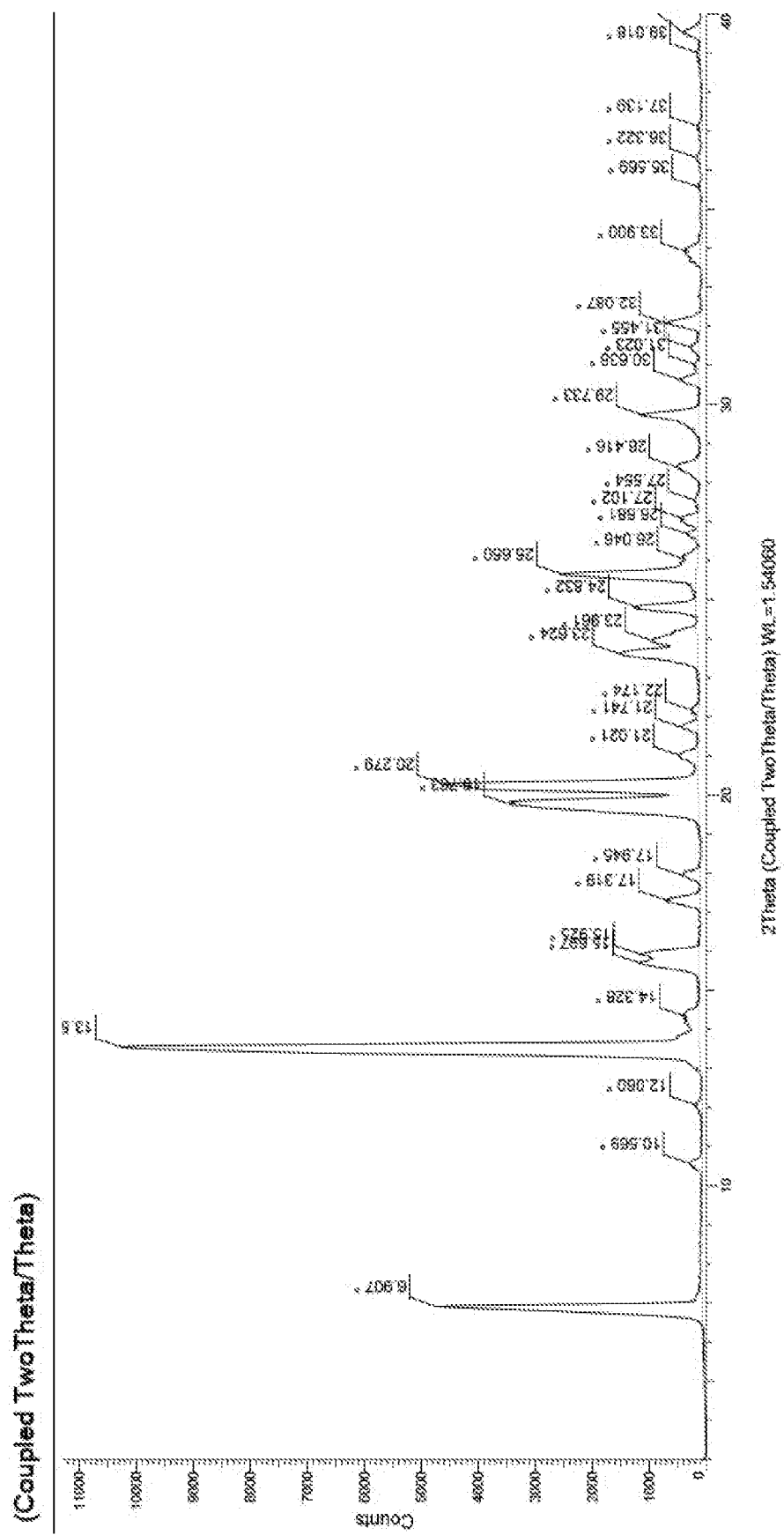
FIG. 25 depicts the X-ray powder diffraction pattern (XRPD) for crystalline free base form of Compound 1.

The XRPD for the crystalline free base form of Compound 1 is shown by FIG. 25 and the peak listings are shown in Table 33.

TABLE 33

| Angle, 2-θ | d spacing (A°) | Rel. Intensity (%) |
|---|---|---|
| 6.9 | 12.8 | 46.1 |
| 10.6 | 8.4 | 1.9 |
| 12.1 | 7.3 | 0.8 |
| 13.5 | 6.5 | 100 |
| 14.3 | 6.2 | 2.2 |
| 15.7 | 5.6 | 10.3 |
| 15.9 | 5.6 | 10.1 |
| 17.3 | 5.1 | 5.9 |
| 17.9 | 4.9 | 2.9 |
| 19.3 | 4.5 | 32.6 |
| 20.3 | 4.4 | 44.0 |
| 21.0 | 4.2 | 3.0 |
| 21.7 | 4.1 | 2.8 |
| 22.2 | 4.0 | 1.0 |
| 23.6 | 3.8 | 13.5 |

TABLE 33-continued

| Angle, 2-θ | d spacing (A°) | Rel. Intensity (%) |
|---|---|---|
| 24.0 | 3.7 | 7.8 |
| 24.8 | 3.6 | 10.6 |
| 25.7 | 3.5 | 23.1 |
| 26.0 | 3.4 | 2.2 |
| 26.7 | 3.3 | 1.7 |
| 27.1 | 3.3 | 2.9 |
| 27.6 | 3.2 | 0.6 |
| 28.4 | 3.1 | 4.0 |
| 29.7 | 3.0 | 9.7 |
| 30.6 | 2.9 | 3.3 |
| 31.0 | 2.9 | 0.7 |
| 31.5 | 2.8 | 1.4 |
| 32.1 | 2.8 | 5.8 |
| 33.9 | 2.6 | 2.2 |
| 35.6 | 2.5 | 0.4 |
| 36.3 | 2.5 | 0.7 |
| 37.1 | 2.4 | 0.8 |
| 39.0 | 2.3 | 0.6 |
| 39.5 | 2.3 | 2.9 |

Pharmacokinetic Evaluation

Methods:

Single dose in suspension using Crystalline Form A micronized and unmicronized, and crystalline free base of Compound 1 were administered to male Sprague-Dawley rat at 200 mg/kg. Blood samples were collected in the presence of $K_2EDTA$, and were centrifuged to obtain plasma. The plasma was then analyzed for these compounds by LC/MS.

Preparation of Test Article for Suspension Dosing in Rats:

All animals involved in the dosing schedule were weighted and assigned numbers. All suspension formulations were freshly made prior use. Each solution was prepared at 40 mg/mL in 0.5% methyl-cellulose solution in water. The tubes were vortex for 2 min and sonicate for 30 min to achieve a white homogenous suspension.

All animals (n=6/group) were dosed orally in a volume of 5 mL/kg. Following dosing, each rat was bled at each of the designated time points. Blood samples were collected from the tail vain. Blood aliquots (150 µl) were collected in tubes coated with $K_2EDTA$, mixed gently then kept on ice and centrifuged at 2,000 g for 5 minutes at 4° C., within 15 min of collection. The plasma layer was collected and maintained frozen at −70° C. until further processing.

Bioanalytical Methods

Bioanalytical quantitation using HPLC/triple quadruple mass spectrometry (HPLC-MS) was performed. Plasma concentrations and T½ were calculated and reported.

Plasma Assay:

A 1 mg/mL standard solution in DMSO:methanol (20:80, v/v) was diluted in 50 fold and subsequently serial diluted in 50% methanol water. Aliquots (10 µl) of the serial dilutions were mixed with 190 ul of control plasma for use as a standard curve. Plasma samples (50 µl) and standard samples (non-diluted) were diluted 10× with ice cold acetonitrile containing 40 ng/ml dexamethasone as internal standard. Acetonitrile precipitated samples and standards were vortexed at 5 g for 2 min (IKA vortex), then centrifuged at 5000 g for 10 min.

For 10-fold dilution standard samples: an aliquot of 5 µL sample was added with 45 µL control plasma to obtain the diluted samples. If a 50-fold dilution standard sample was required: an aliquot of 10 µL 10-fold diluted sample was added with 40 µL blank plasma to obtain the final diluted samples. Then, the exaction procedure for diluted samples was same as those for non-diluted samples.

Samples and standards (10 µl) were injected into the LC-MS system, as described below. Concentrations of dose solutions were reported in mg/mL.

LC-MS Analysis:

LC: 7.5 µl of each sample and standard were injected onto a Waters BEH C18 (2.1×50 mm, 1.7 µm, maintained at 60° C.) column at 0.6 mL/min by an UPLC. The column was equilibrated at 10% acetonitrile. Compounds were eluted with a gradient to 95% acetonitrile. All mobile phase contained 0.025% (v/v) formic acid with 1 mM ammonium acetate.

TABLE 34

Chromatographic elution conditions.

| Time (min) | Mobile Phase B (%) |
|---|---|
| Initial | 10 |
| 0.20 | 10 |
| 0.60 | 95 |
| 1.10 | 95 |
| 1.15 | 10 |
| 1.50 | 10 |

MS: Column eluent was analyzed by electrospray ionization into a triple quadruple mass spectrometer system. Eluent composition was analyzed for ion pair specifics to the internal standard and the analyte respectively.

Pharmacokinetic Analyses

Experimental samples were compared with standard curve samples to determine compound concentrations. Average compound concentrations (in ng/mL±standard deviation) were reported for each time-point. Limit of detection (LLOQ) was reported as the lowest standard curve sample demonstrating a deviation of less than 20% of nominal concentration. PK analysis was performed in Phoenix Winnonlin; $C_{max}$ were determined as the maximum average concentration observed at a given point, the area under the curve (AUC) was reported for $t_0$ to $t_{last}$ ours.

Figure 22:
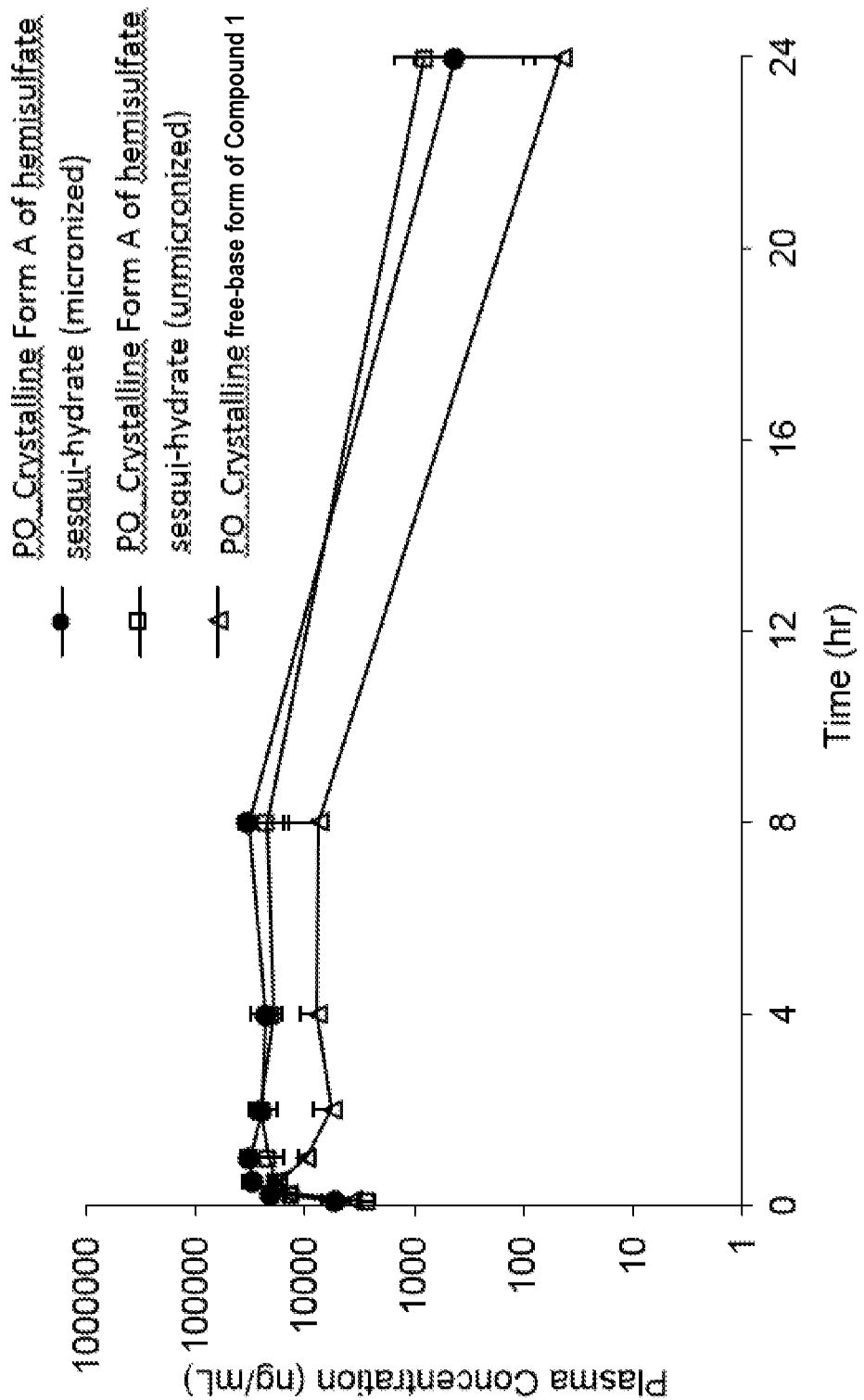
FIG. 22 depicts Mean plasma concentration-time profiles of crystalline Form A after a PO dose in different forms at 200 mg/kg in SD rats (N=6). The dose of crystalline Form A is calculated based on the equivalence to 200 mg/kg of compound 1.

As shown in FIG. 22 and Table 35, crystalline Form A (micronized) and crystalline Form A (unmicronized) were shown to be more soluble in phosphate buffer pH7.4 compared to crystalline free-base of Compound 1. When the plasma concentration-time profiles and pharmacokinetic parameters of crystalline Form A (micronized and unmicronized) were compared to the crystalline free-base of Compound 1 following oral dosing as suspension to fasted male Sprague-Dawley rats, AUC and Cmax were significantly different. The micronized and unmicronized of crystalline Form A showed AUCs 3.8 and 2.7 fold higher compared to crystalline free-base of Compound 1 respectively. Similarly, the micronized and unmicronized of crystalline Form A showed Cmax 2 and 1.6 fold higher compared to crystalline free-base of Compound 1 respectively. In contrast, no significant differences could be observed between the micronized and unmicronized forms of crystalline Form A.

TABLE 35

Characterization summary of compounds used in Pharmacokinetic Study

| Materials | PSD |
|---|---|
| Crystalline Form A (micronized) | D90: 10/D50 = 4.6/ D10 = 1 |
| Crystalline Form A (unmicronized) | D90 = 71/D50 = 32.6/ D10 = 11.55 |
| Crystalline free-base of Compound 1 | D90 = 521/D50 = 206/ D10 = 32 |

TABLE 36

Pharmacokinetic Parameters after PO administration to Sprague-Dawley Rats

| Compound Form | Crystalline Form A (micronized) | Crystalline Form A (unmicronized) | Crystalline free-base of Compound 1 |
|---|---|---|---|
| Oral Dose (mg/kg)* | 200 | 200 | 200 |
| Cmax (ng/mL) | 36700 ± 6800 | 29800 ± 5300 | 17900 ± 3600 |
| AUC 0-last (ng/h/mL) | 478000 ± 87900 | 355900 ± 82900 | 124800 ± 85800 |

*Dose shows the equivalence to the free base form of compound 1.

While a number of embodiments have been described, the scope of this disclosure is to be defined by the appended claims, and not by the specific embodiments that have been represented by way of example. The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:

1. A crystalline form of a compound having the formula:

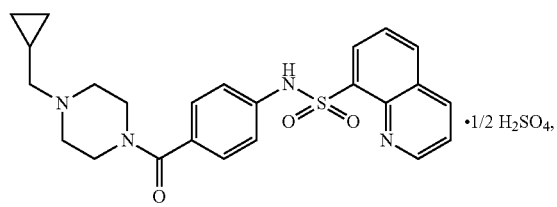 [SMILES: O=C(c1ccc(NS(=O)(=O)c2cccc3cccnc23)cc1)N1CCN(CC2CC2)CC1]

·1/2 $H_2SO_4$, wherein the crystalline form is crystalline Form A characterized by x-ray powder diffraction peaks at 2Θ angles (±0.2°) 9.9°, 15.8°, and 22.6°.

2. The crystalline form of claim 1, wherein the compound is a solvate.

3. The crystalline Form A of claim 1, wherein the crystalline form is characterized by x-ray powder diffraction peaks at 2Θ angles (±0.2°) 9.9°, 15.8°, and 22.6°; and at least one, at least two, or at least three additional x-ray powder diffraction peak at 2Θ angles (±0.2°) selected from 15.0°, 17.1°, 21.3°, and 21.9°.

4. The crystalline Form A of claim 3, wherein the crystalline form is characterized by x-ray powder diffraction peaks at 2Θ angles (±0.2°) 9.9°, 11.4°, 15.0°, 15.3°, 15.8°, 17.1°, 17.7°, 21.3°, 21.9°, 22.6°, and 23.5°.

5. The crystalline Form A of claim 4, wherein the crystalline form is characterized by x-ray powder diffraction peaks at 2Θ angles (±0.2°) 4.9°, 9.9°, 11.0°, 11.4°, 11.7°, 12.3°, 12.8°, 13.6°, 13.9°, 14.2°, 15.0°, 15.3°, 15.8°, 17.1°, 17.4°, 17.7°, 18.8°, 19.1°, 19.8°, 21.3°, 21.9°, 22.6°, 23.0°, 23.2°, 23.5°, 23.8°, 24.1°, 24.5°, 25.3°, 25.6°, 26.1°, 27.1°, 28.1°, and 29.8°.

6. A pharmaceutical composition comprising the crystalline form of claim 1; and a pharmaceutically acceptable carrier.

7. A tablet composition comprising the crystalline form of claim 1; and a pharmaceutically acceptable carrier.

8. A method of forming crystalline Form A of claim 1, the method comprising reacting a compound of Formula 1:

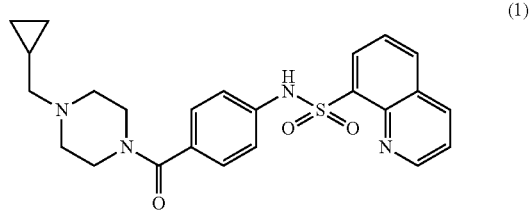 [SMILES: O=C(c1ccc(NS(=O)(=O)c2cccc3cccnc23)cc1)N1CCN(CC2CC2)CC1]

with $H_2SO_4$ in an alcoholic solution.

* * * * *

UNITED STATES PATENT AND TRADEMARK OFFICE
CERTIFICATE OF CORRECTION

PATENT NO. : 11,254,652 B2
APPLICATION NO. : 16/765456
DATED : February 22, 2022
INVENTOR(S) : Jacob P. Sizemore et al.

Page 1 of 1

It is certified that error appears in the above-identified patent and that said Letters Patent is hereby corrected as shown below:

On the Title Page

At Item (72) Inventors, add the following inventors:
--Eric Simone, West Newbury, MA (US);
Shijie Zhang, Cambridge, MA (US);
Jeffrey D. Wilson, Ipswich, MA (US);
Jose Luis Rios Lizarraga, Cambridge, MA (US)--.

Signed and Sealed this
First Day of July, 2025

Coke Morgan Stewart
*Acting Director of the United States Patent and Trademark Office*